US012331333B2

United States Patent
Karamyan et al.

(10) Patent No.: US 12,331,333 B2
(45) Date of Patent: Jun. 17, 2025

(54) ENHANCERS OF NEUROLYSIN ACTIVITY

(71) Applicants: Texas Tech University System, Lubbock, TX (US); University of Florida Research Foundation, Incorporated, Gainesville, FL (US)

(72) Inventors: Vardan T. Karamyan, Amarillo, TX (US); Paul Trippier, Papillion, NE (US); David A. Ostrov, Gainesville, FL (US); Tom Abbruscato, Amarillo, TX (US); Srinidhi Jayaraman, Amarillo, TX (US)

(73) Assignees: TEXAS TECH UNIVERSITY SYSTEM, Lubbock, TX (US); UNIVERSITY OF FLORIDA RESEARCH FOUNDATION, INCORPORATED, Gainesville (FI)

( * ) Notice: Subject to any disclaimer, the term of this patent is extended or adjusted under 35 U.S.C. 154(b) by 1046 days.

(21) Appl. No.: 17/186,489

(22) Filed: Feb. 26, 2021

(65) Prior Publication Data

US 2021/0198647 A1 Jul. 1, 2021

Related U.S. Application Data

(63) Continuation-in-part of application No. PCT/US2019/048702, filed on Aug. 29, 2019.

(60) Provisional application No. 62/725,444, filed on Aug. 31, 2018.

(51) Int. Cl.
*C07K 5/078* (2006.01)
*C12N 9/64* (2006.01)

(52) U.S. Cl.
CPC ........ *C12N 9/6416* (2013.01); *C07K 5/06147* (2013.01); *C12Y 304/24016* (2013.01)

(58) Field of Classification Search
None
See application file for complete search history.

(56) References Cited

U.S. PATENT DOCUMENTS

| | | | |
|---|---|---|---|
| 4,611,076 | A | 9/1986 | Dong et al. |
| 7,863,272 | B2 | 1/2011 | Oksenberg et al. |
| 8,933,056 | B2 | 1/2015 | Bachovchin et al. |
| 2005/0020483 | A1 | 1/2005 | Oksenberg et al. |
| 2017/0196908 | A1 | 7/2017 | Palczewski et al. |

FOREIGN PATENT DOCUMENTS

WO WO-2004089354 A2 * 10/2004 ............ A61K 38/05

OTHER PUBLICATIONS

Olias, G. et al. (2004) Regulation and function of somatostatin receptors. Journal of neurochemistry 89, 1057-1091.

(Continued)

*Primary Examiner* — Thomas S Heard
(74) *Attorney, Agent, or Firm* — Edwin S. Flores; Daniel J. Chalker; Chalker Flores, LLP

(57) ABSTRACT

The present invention includes a composition and method of allosterically potentiating the activity of neurolysin comprising contacting the neurolysin with an amount of a histidine-containing dipeptide that is an allosteric that increases the activity of neurolysin.

5 Claims, 14 Drawing Sheets

Specification includes a Sequence Listing.

(56) References Cited

OTHER PUBLICATIONS

Oliveira, V. et al. (2002) Temperature and salts effects on the peptidase activities of the recombinant metallooligopeptidases neurolysin and thimet oligopeptidase. European journal of biochemistry / FEBS 269, 4326-4334.
Pacholec, M. et al. (2010) SRT1720, SRT2183, SRT1460, and resveratrol are not direct activators of SIRT1. The Journal of biological chemistry 285, 8340-8351.
Qiu, W. Q. et al. (1998) Insulin-degrading enzyme regulates extracellular levels of amyloid beta-protein by degradation. The Journal of biological chemistry 273, 32730-32738.
Rashid, M. et al. (2010) Association of the novel non-AT1, non-AT2 angiotensin binding site with neuronal cell death. J Pharmacol Exp Ther 335, 754-761.
Rashid, M. et al. (2014) Functional upregulation of endopeptidase neurolysin during post-acute and early recovery phases of experimental stroke in mouse brain. Journal of neurochemistry 129, 179-189.
Ray, K. et al. (2004) Crystal structure of human thimet oligopeptidase provides insight into substrate recognition, regulation, and localization. J Biol Chem 279, 20480-20489.
Rioli, V. et al. (1998) Neuropeptide specificity and inhibition of recombinant isoforms of the endopeptidase 3.4.24.16 family: comparison with the related recombinant endopeptidase 3.4.24.15. Biochem Biophys Res Commun 250, 5-11.
Rioli, V. et al. (2003) Novel natural peptide substrates for endopeptidase 24.15, neurolysin, and angiotensin-converting enzyme. J Biol Chem 278, 8547-8555.
Rohnert, P. et al. (2012) Dipeptidyl peptidase IV, aminopeptidase N and DPIV/APN-like proteases in cerebral schemia. J Neuroinflammation 9, 44.
Sargeant, T. J. et al. (2008) Opioidergic regulation of astroglial/neuronal proliferation: where are we now? Journal of neurochemistry 107, 883-897.
Savolainen, M. H. et al. (2015) Prolyl oligopeptidase enhances alpha-synuclein dimerization via direct protein-protein interaction. The Journal of biological chemistry 290, 5117-5126.
Shen, A. (2010) Allosteric regulation of protease activity by small molecules. Mol Biosyst 6, 1431-1443.
Shrimpton, C. N. et al. (1997) Thiol activation of endopeptidase EC 3.4.24.15. A novel mechanism for the regulation of catalytic activity. J Biol Chem 272, 17395-17399.
Shrimpton, C. N. et al. (2002) Soluble metalloendopeptidases and neuroendocrine signaling. Endocrine reviews 23, 647-664.
Simoes, P. S. et al. (2014) Expression and activity of thimet oligopeptidase (TOP) are modified in the hippocampus of subjects with temporal lobe epilepsy (TLE). Epilepsia 55, 754-762.
Song, E. S. et al. (2004) ATP effects on insulin-degrading enzyme are mediated primarily through its triphosphate moiety. The Journal of biological chemistry 279, 54216-54220.
Spencer, B. et al. (2014) A neuroprotective brain-penetrating endopeptidase fusion protein ameliorates Alzheimer disease pathology and restores neurogenesis. The Journal of biological chemistry 289, 17917-17931.
Sumners, C. et al. (2013) Protective arms of the renin-angiotensin-system in neurological disease. Clin Exp Pharmacol Physiol 40, 580-588.
Timmermans, P. B. et al. (1995) Discovery of losartan, the first angiotensin II receptor antagonist. Journal of human hypertension 9 Suppl 5, S3-18.
Towler, P. et al. (2004) ACE2 X-ray structures reveal a large hinge-bending motion important for inhibitor binding and catalysis. The Journal of biological chemistry 279, 17996-18007.
Turner, R. et al. (2007) Inhibition of neurogenic inflammation as a novel treatment for ischemic stroke. Drug News Perspect 20, 221-226.
Tyler-McMahon, B. M. et al. (2000) Neurotensin: peptide for the next millennium. Regulatory peptides 93, 125-136.
Vickers, C. et al. (2002) Hydrolysis of biological peptides by human angiotensin-converting enzyme-related carboxypeptidase. J Biol Chem 277, 14838-14843.
Vincent, B. et al. (1997) Contribution of endopeptidase 3.4.24.15 to central neurotensin inactivation. Eur J Pharmacol 334, 49-53.
Walker, K. et al. (1995) Kinins and kinin receptors in the nervous system. Neurochemistry international 26, 1-16.
Wangler, N. J. et al. (2012) Identification of Membrane-bound Variant of Metalloendopeptidase Neurolysin (EC 3.4.24.16) as the Non-angiotensin Type 1 (Non-AT1), Non-AT2 Angiotensin Binding Site. J Biol Chem 287, 114-122.
Xia, H. et al. (2008) Angiotensin-converting enzyme 2 in the brain: properties and future directions. Journal of neurochemistry 107, 1482-1494.
Albert-Weissenberger, C. et al. (2013) Ischemic stroke and traumatic brain injury: the role of the kallikrein-kinin system. Progress in neurobiology 101-102, 65-82.
Basurto-Islas, G. et al. (2013) Activation of asparaginyl endopeptidase leads to Tau hyperphosphorylation in Alzheimer disease. The Journal of biological chemistry 288, 17495-17507.
Bennion, D. M. et al. (2015) Activation of the Neuroprotective Angiotensin-Converting Enzyme 2 in Rat Ischemic Stroke. Hypertension 66, 141-148.
Bisogno, T. et al. (2010) Cannabinoid receptors and endocannabinoids: role in neuroinflammatory and neurodegenerative disorders. CNS Neurol Disord Drug Targets 9, 564-573.
Brown, C. K. et al. (2001) Structure of neurolysin reveals a deep channel that limits substrate access. Proc Natl Acad Sci U S A 98, 3127-3132.
Burbach, J. P. (2010) Neuropeptides from concept to online database www.neuropeptides.nl. European journal of pharmacology 626, 27-48.
Burbach, J. P. (2011) What are neuropeptides? Methods in molecular biology 789, 1-36.
Caceda, R. et al. (2006) Neurotensin: role in psychiatric and neurological diseases. Peptides 27, 2385-2404.
Chen, J. et al. (2014) Neuronal over-expression of ACE2 protects brain from ischemia-induced damage. Neuropharmacology 79, 550-558.
Cushman, D. W. et al. (1991) History of the design of captopril and related inhibitors of angiotensin converting enzyme. Hypertension 17, 589-592.
Dahms, P. et al. (1992) Purification of the main somatostatin-degrading proteases from rat and pig brains, their action on other neuropeptides, and their identification as endopeptidases 24.15 and 24.16. Eur J Biochem 208, 145-154.
Dauch, P. (1991) Specific inhibition of endopeptidase 24.16 by dipeptides. Eur J Biochem 202, 269-276.
Dauch, P. et al. (1991) Fluorimetric assay of the neurotensin-degrading metalloendopeptidase, endopeptidase 24.16. The Biochemical journal 280 ( Pt 2), 421-426.
Dauch, P. et al. (1995) Molecular cloning and expression of rat brain endopeptidase 3.4.24.16. J Biol Chem 270, 27266-27271.
Davis, T. P. et al. (1993) Peptidases in the CNS: formation of biologically active, receptor-specific peptide fragments. Crit Rev Neurobiol 7, 163-174.
Deu, E. et al. (2012) New approaches for dissecting protease functions to improve probe development and drug discovery. Nat Struct Mol Biol 19, 9-16.
Drag, M. et al. (2010) Emerging principles in protease-based drug discovery. Nat Rev Drug Discov 9, 690-701.
Dundas, J. et al. (2006) CASTp: computed atlas of surface topography of proteins with structural and topographical mapping of functionally annotated residues. Nucleic acids research 34, W116-118.
Eckman, E. A. et al. (2001) Degradation of the Alzheimer's amyloid beta peptide by endothelin-converting enzyme. The Journal of biological chemistry 276, 24540-24548.
Feng, B. Y. et al. (2005) High-throughput assays for promiscuous inhibitors. Nat Chem Biol 1, 146-148.
Feng, B. Y. et al. (2007) A high-throughput screen for aggregation-based inhibition in a large compound library. J Med Chem 50, 2385-2390.

(56) References Cited

OTHER PUBLICATIONS

Feng, Y. et al. (2012) Current research on opioid receptor function. Curr Drug Targets 13, 230-246.
Fontes, R. (2000) Inhibition and activation of enzymes. The effect of a modifier on the reaction rate and on kinetic parameters. Acta Biochim Pol 47, 233-257.
Goode, D. R. et al. (2008) Identification of promiscuous small molecule activators in high-throughput enzyme activation screens. J Med Chem 51, 2346-2349.
Heimann, A. S. et al. (2007) Hemopressin is an inverse agonist of CB1 cannabinoid receptors. Proceedings of the National Academy of Sciences of the United States of America 104, 20588-20593.
Hernandez Prada, J. A. et al. (2008) Structure-based identification of small-molecule angiotensin-converting enzyme 2 activators as novel antihypertensive agents. Hypertension 51, 1312-1317.
Hines, C. S. et al. (2014) Allosteric inhibition of the neuropeptidase neurolysin. The Journal of biological chemistry 289, 35605-35619.
Hokfelt, T., et al. (2003) Neuropeptides: opportunities for drug discovery. TheLancet. Neurology 2, 463-472.
Huang, S. M. et al. (2006) Neprilysin-sensitive synapse-associated amyloid-beta peptide oligomers impair neuronal plasticity and cognitive function. The Journal of biological chemistry 281, 17941-17951.
International Search Report [ISA/US] PCT/US2019/048702 dated Jan. 10, 2020.
Jayaraman et al. "Allosteric Potentiation of Peptidase Neurolysin by Small Molecules," Biophysical Journal, Feb. 16, 2016 (Feb. 16, 2016), vol. 110, Iss. 3, Suppl. 1, pp. 396A-397A.
Joyner, J. C. et al. (2012) Targeted catalytic inactivation of angiotensin converting enzyme by lisinopril-coupled transition-metal chelates. J Am Chem Soc 134, 3396-3410.
Kabsch, W. et al. (1983) Dictionary of protein secondary structure: pattern recognition of hydrogen-bonded and geometrical features. Biopolymers 22, 2577-2637.
Karamyan, V. T. et al. (2007) Enzymatic pathways of the brain renin-angiotensin system: unsolved problems and continuing challenges. Regul Pept 143, 15-27.
Kim, M. et al. (2007) Decreased catalytic activity of the insulin-degrading enzyme in chromosome 10-linked Alzheimer disease families. The Journal of biological chemistry 282, 7825-7832.
Kulemina, L. V. et al. (2011) Prediction of off-target effects on angiotensin-converting enzyme 2. J Biomol Screen 16, 878-885.
Leissring, M. A. (2008) The AbetaCs of Abeta-cleaving proteases. The Journal of biological chemistry 283, 29645-29649.
Lian, W. et al. (2000) Crystallization and preliminary analysis of neurolysin. Acta Crystallogr D Biol Crystallogr 56, 1644-1646.
Lim, E. J. et al. (2007) Swapping the substrate specificities of the neuropeptidases neurolysin and thimet oligopeptidase. The Journal of biological chemistry 282, 9722-9732.
Lipinski, C. A. et al. (2001) Experimental and computational approaches to estimate solubility and permeability in drug discovery and development settings. Adv Drug Deliv Rev 46, 3-26.
Lopez-Otin, C., et al. (2008) Proteases: multifunctional enzymes in life and disease. The Journal of biological chemistry 283, 30433-30437.
Miners, J. S. et al. (2008) Immunocapture-based fluorometric assay for the measurement of neprilysin-specific enzyme activity in brain tissue homogenates and cerebrospinal fluid. Journal of neuroscience methods 167, 229-236.
Monod, J. (1965) On the Nature of Allosteric Transitions: A Plausible Model. Journal of molecular biology 12, 88-118.
Novinec, M. et al. (2014) A novel allosteric mechanism in the cysteine peptidase cathepsin K discovered by computational methods. Nat Commun 5, 3287.
European Search Report, EP 19854587 dated Jul. 8, 2022.
Hart Bradley R. et al: "Molecular Imprinting for the Recognition of N-Terminal Histidine Peptides in Aqueous Solution", Macromolecules, vol. 35, No. 16, Jun. 26, 2002 (Jun. 26, 2002), pp. 6192-6201.
Jayaraman Srinidhi et al: "Allosteric Potentiation of Peptidase Neurolysin by Small Molecules", Biophysical Journal, vol. 110, No. 3, 2016.
Shen Weilin et al: "Current knowledge of intestinal absorption of bioactive peptides", Food & Function, vol. 8, No. 12, Oct. 25, 2017 (Oct. 25, 2017), pp. 4306-4314.
Smith, Michele C et al: "The Journal of Biological Chemistry 8 1988 by The American Society for Biochemistry and Molecular Biology, Inc. Chelating Peptide-immobilized Metal Ion Affinity Chromatography A New Concept in Affinitychromatography for Recombinant Proteins*", Mar. 25, 1988 (Mar. 25, 1988), pp. 7211-7215.
Vogler Raphael et al: Full Paper Dipeptides Made up Solely from Histidine: Solution Behaviour and Zinc Complexation, Eur. J. Inorg. Chem, Jan. 1, 2002 (Jan. 1, 2002), pp. 761-766.

* cited by examiner

FIG. 7A
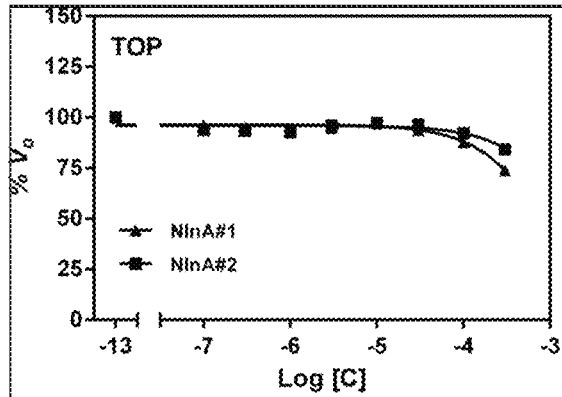
FIG. 7B
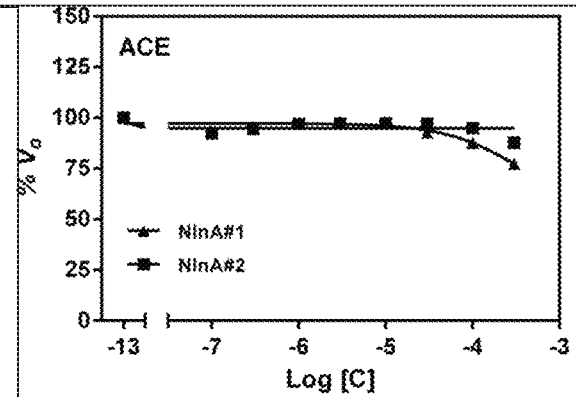
FIG. 7C
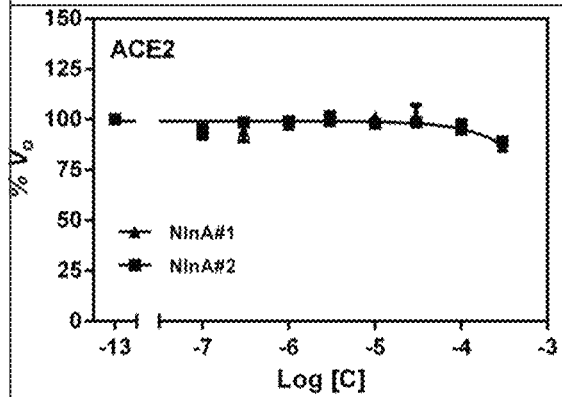
FIG. 7D
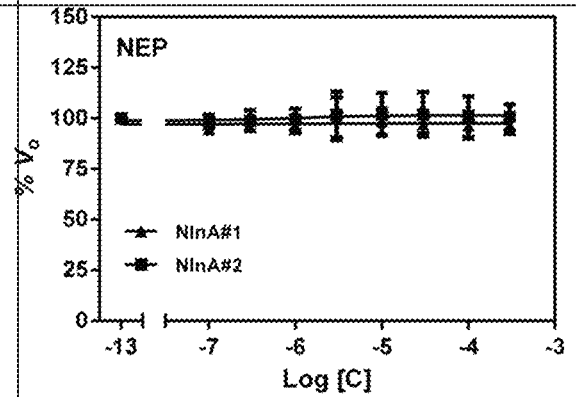
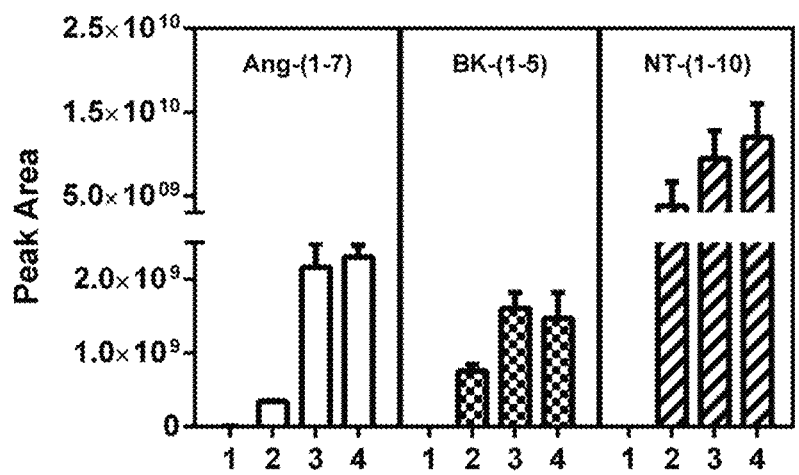
FIG. 8

FROM FIG. 12

[DRVYIHP+3H]³⁺

FRAGMENT ION TABLE, MONOISOTROPIC MASSES

| Seq | # | B | Y | #(+1) |
|---|---|---|---|---|
| D | 1 | 116.03481 | 899.47397 | 7 |
| R | 2 | 272.13592 | 784.44703 | 6 |
| V | 3 | 371.20434 | 628.34592 | 5 |
| Y | 4 | 534.26767 | 529.27750 | 4 |
| I | 5 | 647.35173 | 366.21417 | 3 |
| H | 6 | 784.41064 | 253.13011 | 2 |
| P | 7 | 881.46340 | 116.07120 | 1 |

Sample_3_1pmol #608 RT: 16.02 AV: 1 NL: 4.05E4
F: ITMS + c NSI d Full ms2 300.50@cid35.00 [70.00-915.00]

ENHANCERS OF NEUROLYSIN ACTIVITY

CROSS-REFERENCE TO RELATED APPLICATIONS

This application is a continuation-in-part application of National Stage of International Application No. of PCT/US2019/48702, filed on Aug. 29, 2019 claiming the priority of U.S. Provisional Application No. 62/725,444, filed on Aug. 31, 2018, the content of each of which is incorporated by reference herein.

STATEMENT OF FEDERALLY FUNDED RESEARCH

This invention was made with U.S. Government support awarded by the NIH NINDS grant number 1R01NS106879. The government has certain rights in this invention.

INCORPORATION-BY-REFERENCE OF MATERIALS FILED ON COMPACT DISC

The present application includes a Sequence Listing, which has been submitted in ASCII format via EFS-Web and is hereby incorporated by reference in its entirety. Said ASCII copy, created on Aug. 23, 2019, is named TECH2129WO_SeqList and is 1 kilobytes in size.

TECHNICAL FIELD OF THE INVENTION

The present invention relates in general to the field of molecules that act as neurolysin enhancers, which can be used as therapeutic agents.

BACKGROUND OF THE INVENTION

Without limiting the scope of the invention, its background is described in connection with stroke and neurolysin.

Stroke is a condition where blood flow to the brain is severely reduced or interrupted. Approximately 795,000 people in the United States suffer from a stroke each year, making stroke the fifth leading cause of death in the United States. Stroke is divided into two categories: ischemic and hemorrhagic. Ischemic stroke makes up about 87% of stroke, making it the most common type of stroke. Ischemic stroke occurs by either narrowed or blocked arteries in the brain, causing severely reduced blood flow to brain cells. The reduced blood flow in the brain prevents oxygen and nutrients from reaching brain cells, leading to cell damage or cell death.

Currently, there are only two treatment options for stroke. The first option is the only FDA approved treatment for ischemic stroke, which uses tissue plasminogen activator (tPA)—a thrombolytic drug designed to break up blood clots. The clinical administration of tPA is effective only within 4.5 hours after ischemic stroke symptoms appear. The second treatment option is a surgical procedure to remove the blood clot. About 90% of patients suffering from stroke are not eligible for either treatment, making it crucial to quickly recognize ischemic stroke and have effective therapy for those non-eligible patients.

Neuropeptides are the largest and most diverse signaling molecules in the mammalian brain that function as neurotransmitters, modulators of neurotransmission, autocrine or paracrine regulators that act within a close cellular environment, or hormones/trophic factors which reach to the site of action far from release (1). These properties of neuropeptides make them one of the most critical classes of bioactive molecules involved in response of brain to stress and adaptation to various challenges (e.g., stroke, nerve injury, seizure, and other neurological disorders) (2,3). Actions of neuropeptides are tightly linked to hydrolytic enzymes known as peptidases, which are involved in processing (formation and degradation) of bioactive peptides and are key regulators of neuropeptide function (4-7).

Altered expression and function of several peptidases and related peptidergic systems have been documented in a number of neurological disorders making them potential pharmacological targets for drug development (8-13). The conventional strategy for therapeutic targeting of peptidases and proteases, enzymes hydrolyzing peptide bonds in proteins, has been identification of a specific inhibitor, generally a small molecule, which blocks the active site (14,15). The main pitfall of such approach, which is also the fundamental challenge in developing protease inhibitors into drugs, is the difficulty to achieve target specificity with such inhibitors. The latter is because peptidases and proteases commonly comprise family of proteins with close homologues that have an identical catalytic mechanism and similar substrate specificity profiles (14). Currently, among most promising emerging approaches used to overcome this problem is development of biological or small-molecule allosteric modulators (16-18). The uniqueness of allosteric modulators is in high specificity of such molecules towards the target enzyme because allosteric binding sites are less conserved and exhibit a greater structural diversity than substrate binding sites. Another important feature of allosteric modulators is that they can potentially act as catalytic enhancer, instead of inhibitors, of the target enzyme. Availability of allosteric enhancers as drugs could therapeutically be very valuable if the function of the target peptidase is directed towards protection of the brain and/or its recovery after an insult. Examples of such peptidases include neprilysin, endothelin converting enzymes and insulin degrading enzyme which are the most studied members of amyloid-degrading enzymes involved in clearance of amyloid-β peptides and hence in halting development of Alzheimer's disease (19-22). Angiotensin converting enzyme 2, which is the main peptidase responsible for generation of angiotensin-(1-7), is another example with documented function in protecting brain from stroke injury (23,24).

Thus, a need remains for the development of improved therapies that reduce the effects of ischemic trauma.

SUMMARY OF THE INVENTION

In one embodiment, the present invention includes a method of allosterically potentiating the activity of neurolysin comprising: contacting the neurolysin with an amount of a small molecule that allosterically increases the activity of neurolysin. In one aspect, the small molecule is a histidine-containing dipeptide. In another aspect, the neurolysin is murine or human. In another aspect, the histidine-containing dipeptide reduces the $K_m$ and increased $V_{max}$ values for hydrolysis of one or more neurolysin substrates. In another aspect, the histidine-containing dipeptide is selected from at least one of:

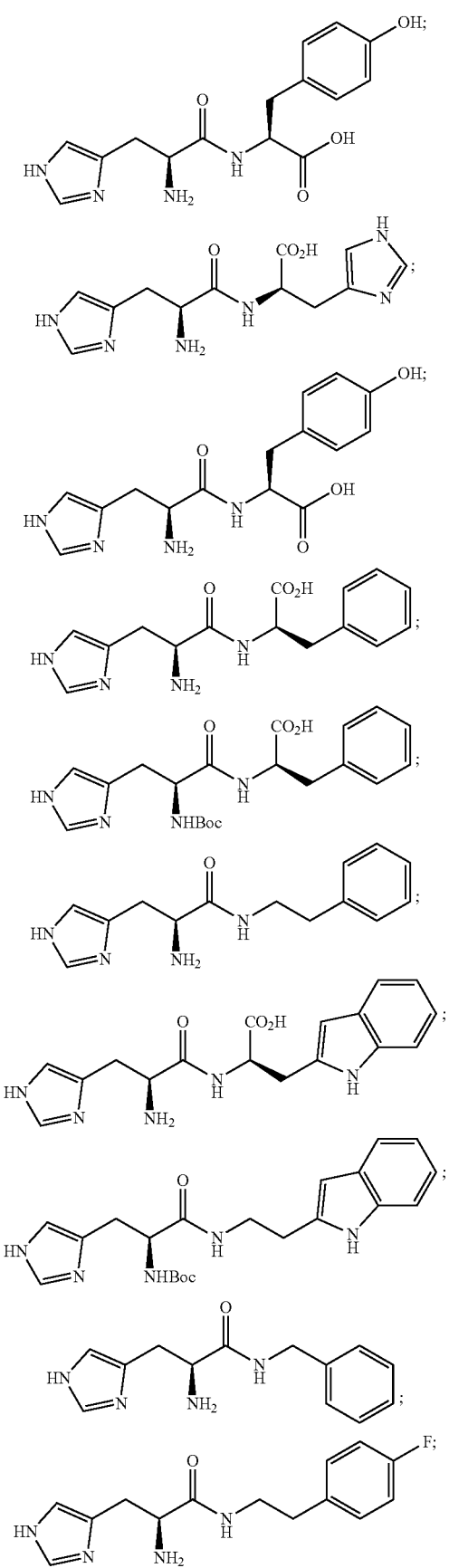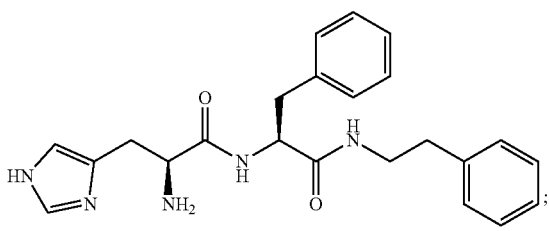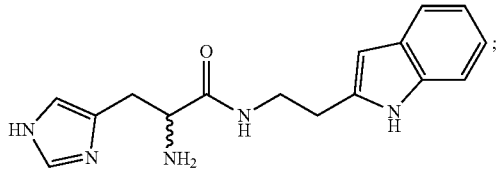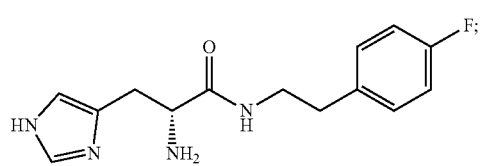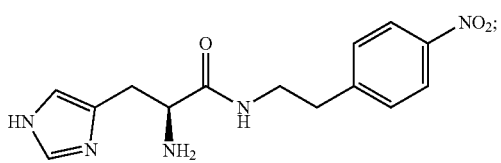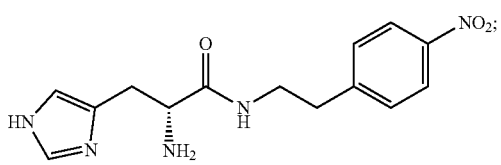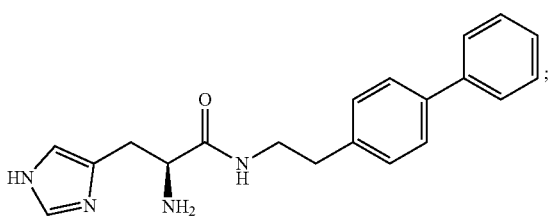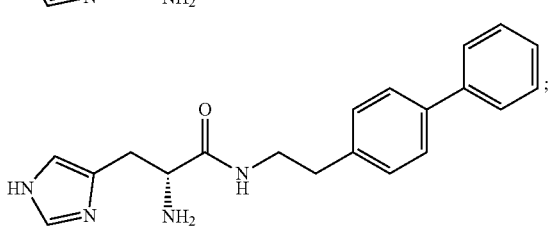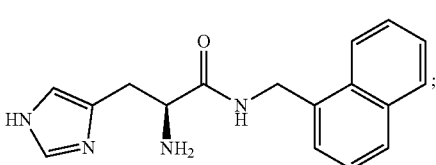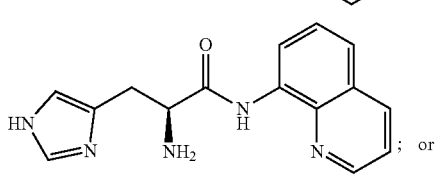

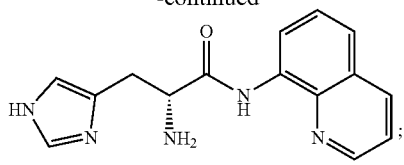

derivatives, salts, or enantiomers thereof.

In another aspect, the histidine-containing dipeptide does not bind at a substrate binding pocket or blocks the binding of a neurolysin substrate. In another aspect, the one or more neurolysin substrates are selected from at least one of neurolyin substrates, neurotensin, bradykinin, angiotensin I, substance P, hemopressin, dynorphin A(1-8), metorphamide, or somatostatin. In another aspect, the histidine-containing dipeptide increases the activity of neurolysin, but does not affect the activity of thimet oligopeptidase (TOP), angiotensin converting enzyme (ACE), angiotensin converting enzyme 2 (ACE2), or neprilysin (NEP). In another aspect, the small molecule that allosterically increases the activity of neurolysin is provided to a subject in an amount sufficient to treat a peripheral inflammatory disorder selected from ischemic stroke, traumatic brain injury, autism, Alzheimer's Disease, dementias or Parkinson's Disease.

Yet another embodiment of the present invention includes an allosteric activator of neurolysin selected from:

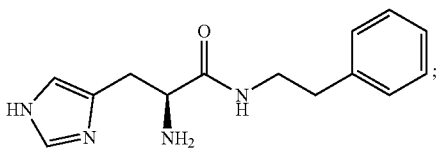
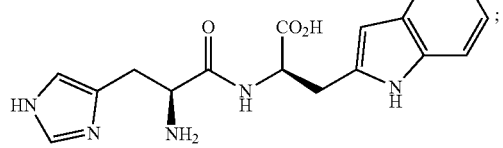
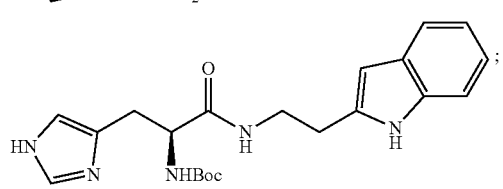
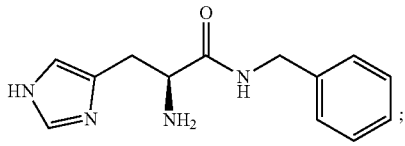
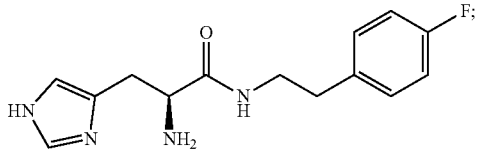
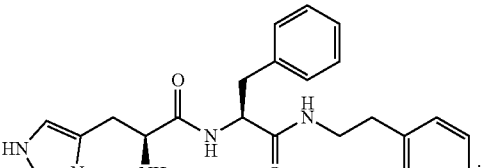
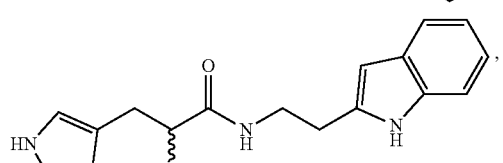
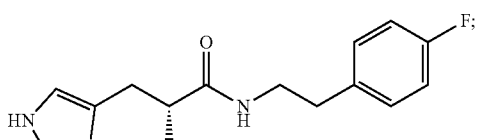
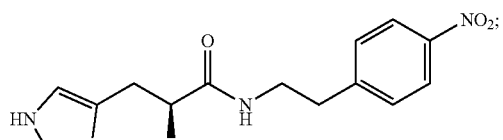
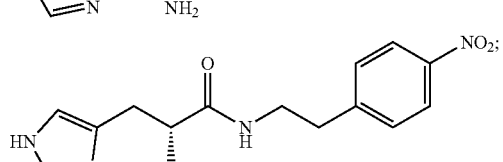

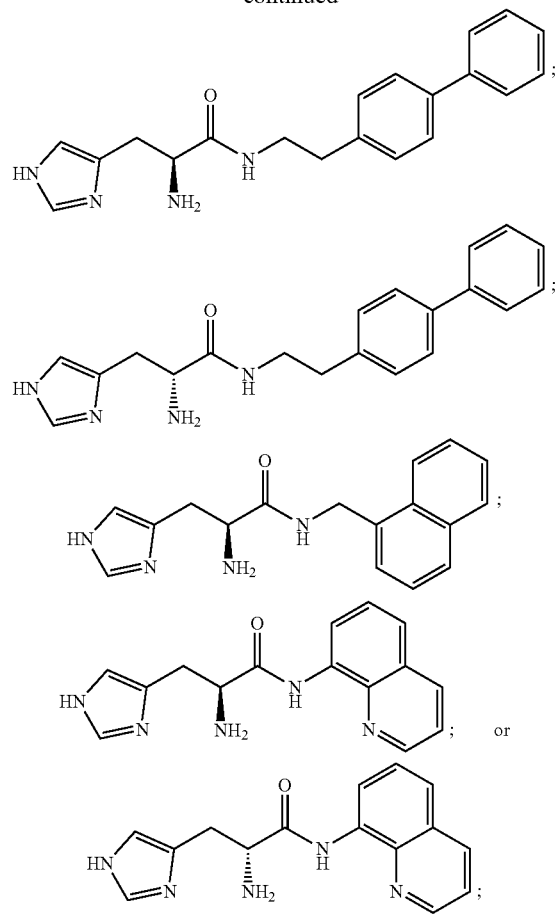

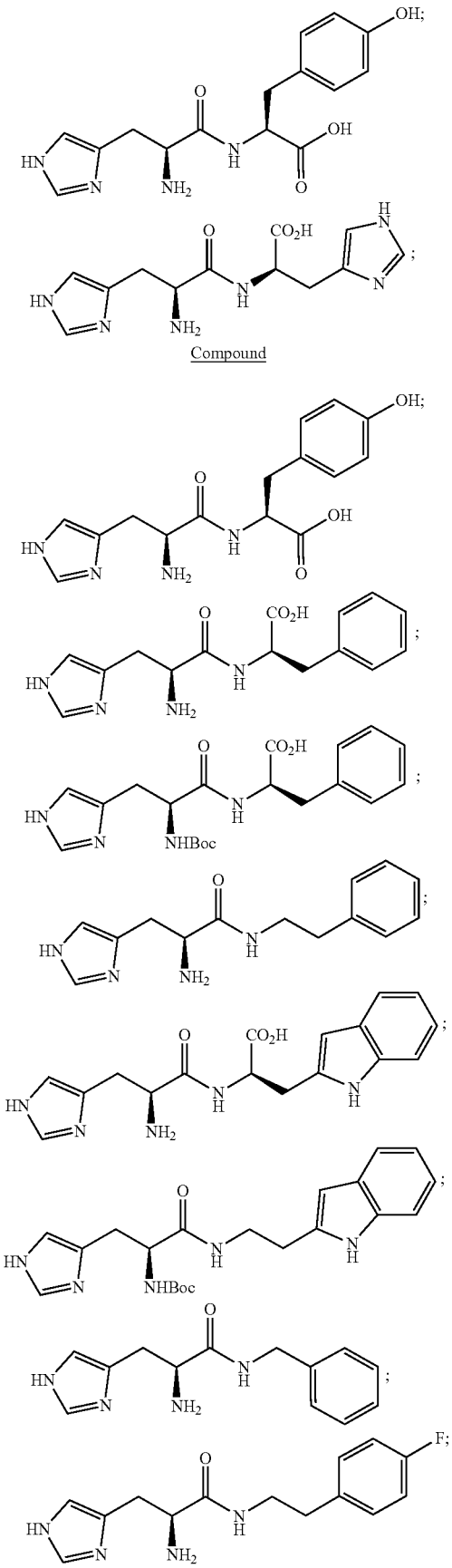

derivatives, salts, or enantiomers thereof. In one aspect, the activator is adapted for oral, intraperitoneal, intradermal, subcutaneous, intravenous, enteral, parental, or pulmonary administration. In another aspect, the activator is combined with one or more excipients, buffers, fillers, or detergents. In another aspect, the activator is adapted for at least one of immediate release, delayed release, or prolonged release. In another aspect, the activator comprises a single enantiomer.

Yet another embodiment of the present invention includes a method of treating the symptoms of peripheral inflammatory disorder comprising: identifying a subject in need of treatment for ischemic stroke; and providing the subject with an amount of an allosteric potentiator of neurolysin sufficient to increase the activity of neurolysin. In one aspect, the peripheral inflammatory disorder is selected from ischemic stroke, traumatic brain injury, autism, Alzheimer's Disease, dementias or Parkinson's Disease. In another aspect, the neurolysin is murine or human. In another aspect, the allosteric potentiator is a histidine-containing dipeptide. In another aspect, the allosteric potentiator reduced the Km and increased Vmax values for hydrolysis of one or more neurolysin substrates. In another aspect, the allosteric potentiator of neurolysin is selected from at least one of:

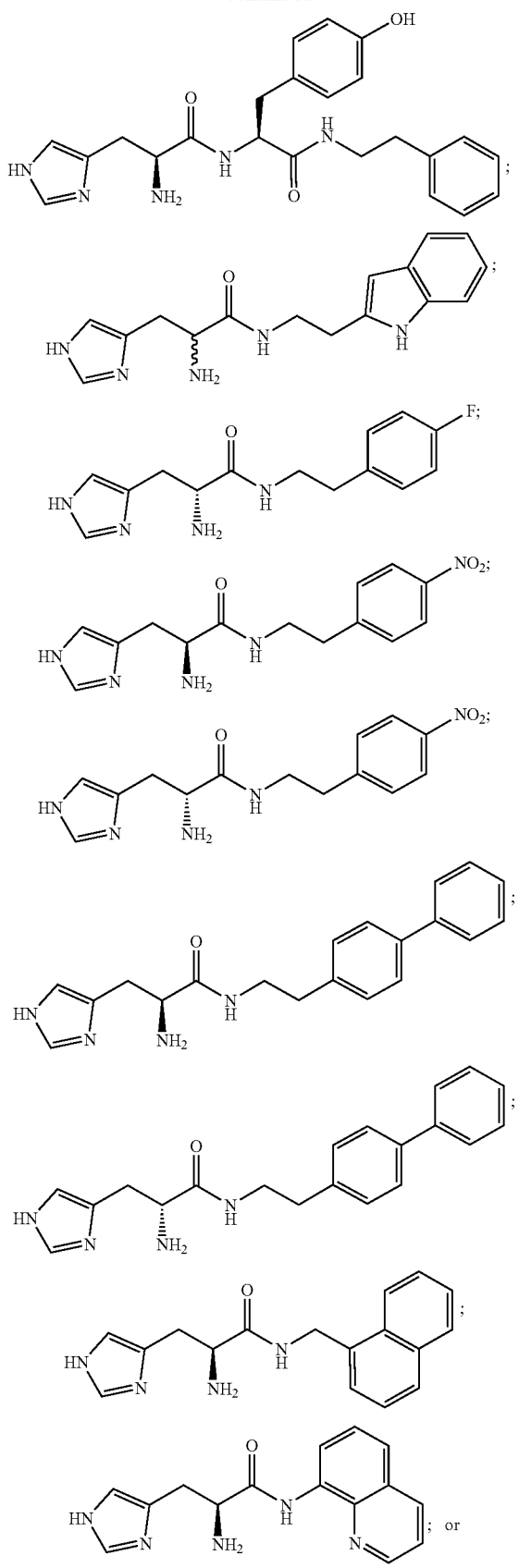
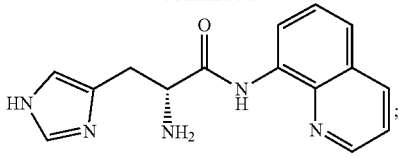

derivatives, salts, or enantiomers thereof. In another aspect, the allosteric potentiator of neurolysin does not bind at a substrate binding pocket or blocks the binding of a neurolysin substrate. In another aspect, the one or more neurolysin substrates are selected from at least one of neurolyin susbtreates, neurotensin, bradykinin, angiotensin I, substance P, hemopressin, dynorphin A(1-8), metorphamide, or somatostatin. In another aspect, the histidine-containing dipeptide increases the activity of neurolysin, but does not affect the activity of thimet oligopeptidase (TOP), angiotensin converting enzyme (ACE), angiotensin converting enzyme 2 (ACE2), or neprilysin (NEP).

BRIEF DESCRIPTION OF THE DRAWINGS

For a more complete understanding of the features and advantages of the present invention, reference is now made to the detailed description of the invention along with the accompanying figures and in which:

FIG. 1A: superposition of ribbon diagrams of ACE2 (cyan) and neurolysin (orange) and their hinge regions. Open conformations of both peptidases were used based on their published crystal structures (33, 41, relevant portions incorporated by reference). The yellow spheres represent the site in the hinge region of neurolysin selected for molecular docking. FIG. 1B: the crystal structure of neurolysin shown in the same orientation as in the left panel. The molecular surface is colored gold and red for carbon, and blue for nitrogen. Yellow spheres depict sites for interaction of potential ligand atoms used in molecular docking orientations. The box in magenta represents the boundaries of the scoring grid used to generate scores that consider electrostatic (polar) and van der Waals (non-polar) interactions.

FIGS. 2A to 2C show the effect of compounds NlnA #1 and NlnA #2 on catalytic activity of rat recombinant neurolysin. FIGS. 2A and 2B: representative reaction progress curves of QFS hydrolysis (25 μM) by rat recombinant neurolysin (0.3 nM) in the presence of different concentrations of NlnA #1 and NlnA #2. FIG. 2C: concentration-dependent effect of both compounds on hydrolysis of QFS under the same experimental conditions (n=3, mean±SD are presented). Note that the initial velocity of the hydrolysis in the absence of either compound corresponds to 100% on the vertical axis and to −13 on the horizontal axis. Calculated $EC_{50}$ value for NlnA #1 is 45.4 μM (95% confidence intervals 29.9 to 68.9 μM), and $E_{max}$ is 234.7% (95% confidence intervals 219.0 to 250.4%). Calculated $EC_{50}$ value for NlnA #2 is 45.8 μM (95% confidence intervals 32.0 to 65.6 μM), and $E_{max}$ is 202.8% (95% confidence intervals 192.2 to 213.4%).

FIG. 3 shows the effect of compounds NlnA #1 and NlnA #2 on the potency of dynorphin A (1-13). Concentration-dependent inhibitory effect of dynorphin A (1-13) on hydrolysis of QFS (15 μM) by rat recombinant neurolysin (rNln, 0.3 nM) in the absence or presence of NlnA #1 or NlnA #2 (100 μM) is presented (n=3, mean±SD are presented, FLU— fluorescence unit). Note that the initial velocity of the hydrolysis in the absence of dynorphin A (1-13) corresponds to −13 on the horizontal axis. Calculated $IC_{50}$ values for dynorphin A (1-13) are: 1.52 µM (95% CI: 0.9-2.5 µM) in rNln, 1.40 µM (95% CI: 1.1-1.8 µM) in rNln+NlnA #1, and 1.20 µM (95% CI: 0.91-1.5 µM) in rNln+NlnA #2.

FIGS. 7A to 7D show the effect of compounds NlnA #1 and NlnA #2 on catalytic activity of human recombinant peptidases. All panels document concentration-dependent effect of NlnA #1 and NlnA #2 on hydrolysis of a respective quenched fluorescent substrate (n=3, mean±SD are presented): Mca-Pro-Leu-Gly-Pro-D-Lys(DNP)-OH at 25 µM for thimet oligopeptidase (TOP)(FIG. 7A), Mca-Arg-Pro-Pro-Gly-Phe-Ser-Ala-Phe-Lys(Dnp)-OH at 10 µM for angiotensin converting enzyme (ACE) (FIG. 7B) and neprilysin (NEP) (FIG. 7D), and Mca-Ala-Pro-Lys-(Dnp)-OH at 10 µM for angiotensin converting enzyme 2 (ACE2) (FIG. 7C). In all panels, the initial velocity of the hydrolysis in the absence of either compound corresponds to 100% on the vertical axis and to −13 on the horizontal axis.

FIG. 8 shows the effect of compounds NlnA #1 and NlnA #2 on hydrolysis of endogenous substrates by neurolysin. Rat recombinant neurolysin (rNln, 2 nM) was incubated with angiotensin I, bradykinin or neurotensin (20 µM) in the absence or presence of NlnA #1 or NlnA #2 (100 µM), and generation of angiotensin-(1-7) (Ang-(1-7)), bradykinin-(1-5) (BK-(1-5)) and neurotensin-(1-10) (NT-(1-10)) was documented by mass spectrometry analysis, respectively (n=2, mean±SD are presented). Column 1 in all panels represents the amount of respective peptide fragment, i.e. product of hydrolysis, in the absence of rNln; column 2—the amount of respective peptide fragment generated in the presence of rNln alone; columns 3 and 4—the amount of respective peptide fragment generated in the presence of rNln plus NlnA #1 or NlnA #2, respectively.

DETAILED DESCRIPTION OF THE INVENTION

Figure 1A:
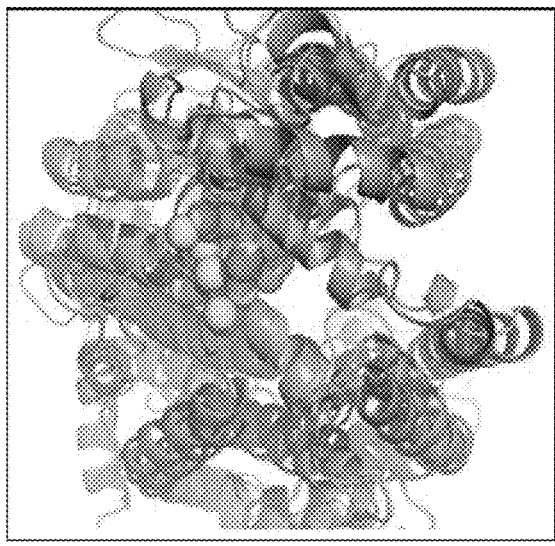
FIGS. 1A and 1B, show the surface pocket in the hinge region selected for molecular docking.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

Example 1. Discovery of a Group of Small Molecules that Specifically Enhance the Catalytic Efficiency of Peptidase Neurolysin The present inventors describe the discovery of a group of small molecules that specifically enhance the catalytic efficiency of peptidase neurolysin. A computational approach was used to explore the structure of neurolysin and identify a druggable surface pocket in its hinge region, followed by docking and ranking of 139,735 molecules from the NCI Developmental Therapeutics Program database. Top ranking compounds were subjected to pharmacological evaluation to identify an enhancer of neurolysin activity. Two structurally related compounds were identified which enhanced the rate of substrate hydrolysis by recombinant (human and rat) and mouse brain-purified neurolysins in a concentration-dependent manner. Neither the identified modulators nor dynorphin A(1-13), a competitive inhibitor, affected each other's affinity in modulating activity of neurolysin, suggesting that the modulators do not bind to the substrate binding site. Both modulators reduced $K_m$ and increased $V_{max}$ values for hydrolysis of the synthetic substrate by neurolysin in a concentration-dependent manner. The modulators had negligible effect on catalytic activity of thimet oligopeptidase, neprilysin, angiotensin converting enzyme (ACE) and ACE2, indicating that they are specific to neurolysin. Both modulators also enhanced hydrolysis of endogenous substrates, suggesting independence of their effect from the synthetic substrate. The identified molecules could be developed into research tools for evaluation of the (patho)physiological function of neurolysin, and may aim development of a new drug class. This study is one of few utilizing a structure-based drug-discovery approach for rational identification of enzyme activators, and by that it demonstrates applicability of this methodology for identification of allosteric modulators of other enzymes.

The present inventors have previously suggested that peptidase neurolysin plays a role in processes modulating the brain's response to stroke and its recovery after stroke (25). Neurolysin (EC 3.4.24.16) is a zinc endopeptidase belonging to the thermolysin-like mammalian family of peptidases (26), which are maximally active at neutral pH and comprise the most studied group of peptidases involved in hydrolytic processing of bioactive peptides in the extracellular environment (5). The hypothesized role of brain neurolysin in response to stroke is based on observations indicating sustained functional up-regulation of this peptidase in mouse brain for at least 7 days after stroke, and diversity of its endogenous substrates with well-documented role in pathogenesis of stroke (25). To develop novel approaches to aid in the treatment of ischemic trauma, and to aid in the understanding of the (patho)physiological function of neurolysin in stroke and other neurological disorders, the present invention was developed.

The present inventors describe herein the discovery of small molecules that enhance catalytic efficiency of neurolysin. For this purpose, a computational approach was used to explore structure of neurolysin and identify a specific, druggable allosteric surface pocket, followed by molecular docking and ranking of 139,735 drug-like small molecules from the National Cancer Institute Developmental Therapeutics Program (NCI DTP) database. Top ranking compounds were received from NCI DTP and subjected to unbiased pharmacological evaluation to identify a molecule specifically enhancing activity of neurolysin. Two structurally similar compounds were identified which increased the rate of substrate hydrolysis by recombinant (human and rat) and mouse brain-purified neurolysins in a concentration-dependent manner. Concentration-response experiments involving the identified modulators and dynorphin A(1-13), a competitive inhibitor of neurolysin, revealed that neither the compounds, nor dynorphin A(1-13), affected each other's affinity in modulating activity of neurolysin. At two different concentrations, both modulators reduced $K_m$ and increased $V_{max}$ values (i.e., increased $V_{max}/K_m$ ratio) for hydrolysis of the synthetic substrate by neurolysin. Enhanced activity of neurolysin was observed not only with use of the synthetic substrate but also with three endogenous substrates of the peptidase. Both modulators had either no, or marginal, effects on catalytic activity closely related peptidases, including thimet oligopeptidase, neprilysin, angiotensin converting enzyme (ACE) and ACE2. This is the first report in scientific literature describing the discovery of specific, small molecule enhancers of neurolysin activity. The identified molecules can be used to target neurolysin in pathogenesis of stroke and other neurological disorders, and may serve as starting structures for development of a new class of drugs.

Molecular docking—Candidate small molecule modulators of neurolysin were selected based on the strategy used for discovery of allosteric enhancers of angiotensin converting enzyme 2 (ACE2) (27,28). In the current study, structural analysis of the hinge region of neurolysin in its open conformation was carried out using DSSP (29) and castP (30) to identify unique structural pockets with adequate solvent accessible volumes and chemical characteristics for binding of drug-like small molecules (molecular weight: <500; octanol/water partition coefficients: <5; H-bond donors: <5; H-bond acceptors: <10 (31)). One potentially druggable site was found unique to the open conformation of the neurolysin hinge region. Programs implemented in the DOCK program package (UCSF) were used to generate files used for molecular docking. SPHGEN was used to position spheres in the selected hinge site, GRID was used to calculate scoring grids with a box size 5 angstrom from the selected spheres. DOCK 6.5 (UCSF) was used to dock and rank 139,725 compounds from the NCI DTP repository (zinc.docking.org/catalogs/ncip). The job was run on the University of Florida High Performance Computing Facility by parallel processing. Compounds were selected to include protonation variants at medium pH (5.75-8.25). Each molecule was positioned into the selected surface pocket in 1000 different orientations and scored with rank based on the predicted polar (H-bonding) and nonpolar (van der Waals) interactions. Top scoring 40 compounds (0.03% of the chemical library screened) were received from NCI DTP and used for pharmacological evaluation (see below).

Rat recombinant neurolysin—N-terminal polyhistidine tagged recombinant rat neurolysin was produced in *Escherichia coli* using a plasmid construct in pBAD/His vector system (Invitrogen) kindly provided by Dr. David W. Rodgers (University of Kentucky) (32,33). Bacterial culture was carried out in Terrific Broth in 2 L Erlenmeyer flasks using an incubator shaker (I-2400, New Brunswick Scientific). Expression was induced by addition of arabinose (1 mM final concentration), the cells were pelleted 3 h after induction and stored at −80° C. freezer. Bacterial pellets were resuspended and lysed in phosphate buffer (20 mM NaH$_2$PO$_4$, 500 mM NaCl, 0.05% Tween-20, pH 8.0) containing 0.25 mg/ml lysozyme, 1 mM phenylmethylsulfonyl fluoride, 0.05 mg/ml DNAse and 0.02 mg/ml RNase, followed by brief sonication. After centrifugation (40,000×g, 20 min at 4° C.) the supernatant was applied to a Ni-NTA Superflow cartridge (Qiagen), followed by washing and elution of recombinant neurolysin with phosphate buffer containing 25 and 250 mM imidazole, respectively. The eluted protein was further purified by size exclusion chromatography using a TSK gel BioAssist G2SWxl column (Tosoh bioscience) in AKTA Purifier FPLC system (GE Healthcare). Purity of recombinant neurolysin (≥95%) was verified by SDS-PAGE and size exclusion chromatography, whereas identity was confirmed by Western blotting using a specific anti-neurolysin antibody (TriplePointBiologics; product number RP3—Neurolysin) (25,34). Specific activity of recombinant neurolysin was determined by an enzymatic assay described below.

Human recombinant peptidases—recombinant human neurolysin (product number 3814-ZN), thimet oligopeptidase (TOP; product number 3439-ZN), neprilysin (NEP; product number 1182-ZNC), angiotensin converting enzyme (ACE; product number 929-ZN), and ACE2 (product number 933-ZN) were purchased from R & D systems.

Mouse brain neurolysin—P10 mouse forebrains were used for purification of native neurolysin as expression of the peptidase is about 5 times higher in comparison to adult mouse forebrain (34,35). In brief, forebrains were homogenized in hypotonic buffer (20 mM NaPO4, pH 7.2) followed by gentle sonication and centrifugation (30 min at 48,000×g at 4° C.). The resulting supernatant was filtered through a 100 kDa cut-off centrifugal filtering unit and concentrated in a 30 kDa cut-off centrifugal filtering unit (Amicon Ultra; Millipore). Neurolysin was semi-purified from the concentrate by size exclusion chromatography using a Superdex 200 Increase 10/300 GL column (GE Healthcare) in AKTA Purifier FPLC system (GE Healthcare). Elution of neurolysin was tracked by the enzymatic assay described below, and the fraction with the highest neurolysin activity was directly used for the experiments.

Enzymatic assays—activity of neurolysin was measured in a continuous assay by documenting the increase in fluorescence occurring upon cleavage of a quenched fluorescent substrate (QFS) Mca-Pro-Leu-Gly-Pro-D-Lys (DNP)-OH (Bachem) (25,36). In brief, a fixed concentration of recombinant or mouse brain purified neurolysin was incubated with 25 µM (for primary screening and determination of EC$_{50}$ values) or 2.5 to 75 µM (for determination of K$_m$ and V$_{max}$ values) QFS in artificial cerebrospinal fluid (NaCl 126 mM, NaHCO$_3$ 26 mM, KCl 3 mM, KH$_2$PO$_4$ 1.4 mM, HEPES 25 mM, glucose 4 mM, MgCl$_2$ 1.3 mM, CaCl$_2$) 1.4 mM, ZnSO$_4$ 0.0002 mM, pH 7.2) containing 0.01% final assay concentration of Triton X-100 at 37° C. In studies involving dynorphin A(1-13), a fixed concentration of rat recombinant neurolysin was incubated with 15 µM QFS and varying concentrations of dynorphin A(1-13) in the absence or presence of one of the modulators at 100 µM. In the reverse experiment, a fixed concentration of rat recombinant neurolysin was incubated with 15 µM QFS and varying concentrations of one of the modulators in the absence or presence of dynorphin A(1-13) at 1 µM. All assays were initiated by addition of QFS (100 µl assay volume in 96-well plates), and each experimental sample was present in duplicate. Generation of the fluorescent product (Mca-Pro-Leu-OH; λex=320, λem=405) was documented every 1 min in a plate reader (SynergyMX; Biotek) at initial velocity conditions where less than 20% of the substrate was metabolized. For mouse brain purified neurolysin, Pro-Ile-inhibited (10 mM final assay concentration) fraction of substrate hydrolysis was considered neurolysin specific.

Activity of recombinant human TOP was assessed in the same way as for neurolysin, except that the assay was carried out in the presence of 0.1 mM dithiothreitol (37). Likewise, activities of recombinant human ACE, NEP and ACE2 were measured similar to neurolysin, except that quenched fluorescent substrate Mca-Arg-Pro-Pro-Gly-Phe-Ser-Ala-Phe-Lys(Dnp)-OH (SEQ ID NO:1) was used for ACE and NEP (38,39), and Mca-Ala-Pro-Lys-(Dnp)-OH (SEQ ID NO:2) was used for ACE2 (40) (both substrates at 10 µM final assay concentration, obtained from Enzo Life Sciences).

Screening of test compounds—primary screening of top-ranked 40 compounds (received from NCI DTP) was carried out at 10 and 100 µM final assay concentrations. Determination of EC$_{50}$ values was conducted in the presence of 0.1 to 300 µM final assay concentrations of the two identified activators. In all experiments, test compounds were incubated with neurolysin for 10 min at 37° C. before addition of the substrate to start the reaction. All test compounds were dissolved in DMSO at 10 to 50 mM stock concentrations. Presence of DMSO (up to 3.5%) did not affect activity of the enzyme.

Endogenous substrates of neurolysin and mass spectrometry analysis—hydrolysis of neurotensin, bradykinin and angiotensin I (20 µM; obtained from American Peptide Company) by recombinant rat neurolysin (2 nM in artificial cerebrospinal fluid containing 0.01% Triton X-100) was carried out in the absence and presence of the two identified modulators (100 µM) at 37° C. for 20 min. The reaction was stopped with HCl (~32 mM final concentration) followed by freezing at −80° C.

One pmol of each sample was subjected to LC-MS/MS analysis using a Dionex 3000 Ultimate nano-LC system (Dionex, Sunnyvale, CA) and a LTQ Orbitrap Velos mass spectrometer (Thermo Scientific, San Jose, CA). Samples were online-purified using Acclaim PepMap100 C18 pre-column (75 µm×2 cm, 3 µm, 100 Å, Dionex) and separated using Acclaim PepMap100 C18 RSLC column (75 µm×15 cm, 2 µm, 100 Å, Dionex). A 30 min LC elution gradient was employed at 350 nL/min flow rate and 29.5° C. column compartment temperature. The elution gradient of solvent B was: 5% over 10 min, 5%-90% over 10 min and 90% over 10 min. Solvent B consisted of 100% ACN containing 0.1% formic acid, while solvent A composed of 98% HPLC water containing 0.1% formic. Eluting peptides were ionized by electrospray ionization at 1.5 kV. The LTQ Orbitrap Velos mass spectrometer was operated in data-dependent acquisition mode comprised of two scan events. The first scan event was a full MS scan of 300-2000 m/z at a mass resolution of 60,000. The precursor ions with charge state +2 or higher were subjected to the second scan, which was a collision induced dissociation (CID) MS/MS scan. The isolation width was set to 3.0 m/z, the normalized collision energy was set to 35%, and the activation Q value was set to 0.250. The top 5 most intense ions observed in the MS scan event were subjected to the CID MS/MS scan. The dynamic exclusion was set to have repeat count of 2, repeat duration of 30 s, exclusion list size of 200 and exclusion duration of 90 s. The relative quantitation of each peptide was achieved by summing up the extracted peak area of all the observed protonated precursor ions corresponding to the certain peptide.

Statistical Analyses—statistical analyses and curve fitting were conducted with GraphPad Prism 6.0 software. For each enzymatic reaction, slope of the line which represents the initial velocity (Vo) for the reaction progress curve was calculated using the liner regression model of the software (Vo=Slope=Δ fluorescent intensity of the reaction product/Δ time). $EC_{50}$ values for the modulators were calculated by fitting initial velocity values for hydrolysis of QFS by neurolysin in the presence of varying concentrations of a modulator into a nonlinear regression model for the three-parameter log(stimulator) vs. response equation [Y=Bottom+(Top−Bottom)/(1+10^((Log $EC_{50}$−X)))]. $IC_{50}$ values for dynorphin A(1-13) were calculated by fitting initial velocity values for hydrolysis of QFS by neurolysin in the presence of varying concentrations of dynorphin A(1-13) into a nonlinear regression model for the three-parameter log(inhibitor) vs. response equation [Y=Bottom+(Top−Bottom)/(1+10^((X−Log $IC_{50}$)))]. Ki values were determined using the Cheng-Prusoff equation: $Ki=IC_{50}/(1+S/Km)$ where S is the substrate concentration (15 µM QFS in our experiments), and Km is the Km value for the substrate (15 µM for QFS, see Table 3). Km and Vmax values were calculated by fitting initial velocity values for hydrolysis of varying concentrations of QFS by neurolysin in the absence or presence of 40 or 100 µM of each modulator into Michaelis-Menten equation [Y=Vmax*X/(Km+X)]. Data are presented as mean with 95% confidence intervals or mean±S.D.

Molecular docking—In this study, a structural analysis of the hinge region of neurolysin in its open conformation was carried out to identify a unique surface pocket. The search for an allosteric site was carried out in the hinge region because crystal structures of neurolysin demonstrates that catalysis is accompanied by large a hinge-bending motion (33,41). The hinge region can affect the distance between the two structural domains and by that modulate substrate binding and catalysis. Moreover, the equilibrium between open and closed conformations can be perturbed with drug-like small molecules to enhance or inhibit catalytic activity. Lastly, peptidases are sensitive to activation by monovalent anions.

The hinge region in neurolysin showed presence of several surface pockets with adequate solvent accessible volumes (DSSP (29)) and castP (30)). One of these pockets was selected as a potential allosteric site (FIGS. 1A and 1B) because it is located at a position analogous to the ACE2 site used for selection of small molecule enhancers of catalytic activity.

Figure 1B:
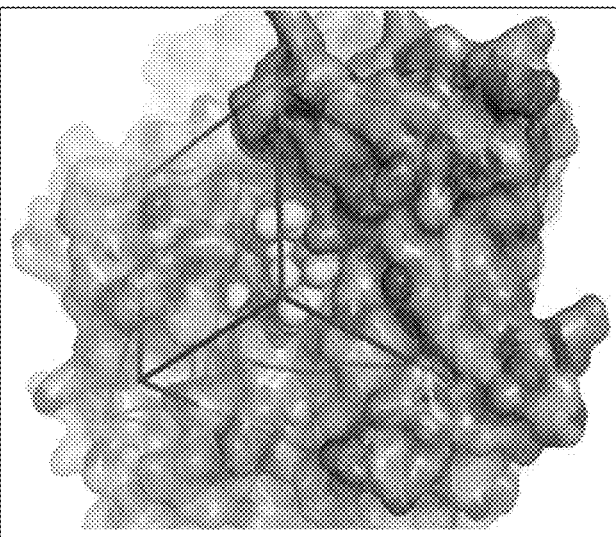

The selected surface pocket was used for molecular docking and virtual, high-throughput screening of drug-like compounds from NCI DTP (FIGS. 1A and 1B). As a result of in silico screening the compounds were ranked according to their combined energy scores for hydrogen bonding and van der Waals contact interactions with the selected surface pocket (Table 1).

TABLE 1

Top ten scoring compounds for the selected surface pocket, i.e. the hypothesized allosteric binding site, on the hinge region of neurolysin.

| Rank | ID | LogP | H- | H- | MW | VDW | ES | Score |
|---|---|---|---|---|---|---|---|---|
| 1 | NSC 42215* | 2.41 | 0 | 3 | 184.234 | 19.338 | −108.107 | −88.767 |
| 2 | NSC 353874 | 1.24 | 1 | 3 | 196.245 | −9.700 | −46.004 | −55.705 |
| 3 | NSC 128977 | −0.03 | 2 | 6 | 272.174 | 8.901 | −59.141 | −50.239 |
| 5 | NSC 359097 | −1.65 | 2 | 3 | 169.178 | 3.290 | −50.315 | −47.025 |
| 6 | NSC 14541 | −0.52 | 2 | 4 | 228.38 | −26.993 | −19.369 | −46.363 |
| 7 | NSC | −1.71 | 5 | 8 | 292.296 | −32.834 | −11.721 | −44.555 |
| 8 | NSC 155877 | −1.48 | 0 | 3 | 334.655 | −23.804 | −19.725 | −43.529 |

TABLE 1-continued

Top ten scoring compounds for the selected surface pocket, i.e. the hypothesized allosteric binding site, on the hinge region of neurolysin.

| Rank | ID | LogP | H- | H- | MW | VDW | ES | Score |
|---|---|---|---|---|---|---|---|---|
| 10 | NSC 302851 | −5.51 | 4 | 6 | 240.291 | −26.927 | −15.557 | −42.484 |
| 11 | NSC 600947 | 1.72 | 1 | 3 | 239.403 | −30.350 | −12.113 | −42.463 |
| 12 | NSC 163084 | −0.59 | 4 | 6 | 352.404 | −34.094 | −8.321 | −42.416 |

VDW - van der Waals interactions;
ES - electrostatic interactions
*NSC 42215 was also ranked #4 with combined score of −48.091 (was not used in the enzymatic assays as it was not available from NCI DTP or from a commercial vendor);
**NSC 523374 was also ranked #9 with combined score of −43.371. Note that ranking of a compound more than once indicates that it can bind to neurolysin in more than one orientation.

Primary and secondary screens—Top ranking 40 compounds identified in the virtual screen were obtained from NCI DTP and used at 10 and 100 M concentrations to observe their effects on ability of recombinant rat neurolysin to hydrolyze QFS. Table 2 summarizes the effects of all compounds on activity of the peptidase at both concentrations. Among them there were more than a handful of compounds showing inhibition of the peptidase at both concentrations, and two compounds (NSC 374121 and NSC 523374), which showed robust, concentration-dependent activation of neurolysin.

TABLE 2

Structure, $A_{50}$ and $A_{max}$ activity data for synthesized dipeptide Neurolysin (Nln) activators.

| Compound | Code | $A_{50}$ (μM; 95% CI) | $A_{max}$ (%; 95% CI) |
|---|---|---|---|
|  | His-Tyr | 37.7 (24.5 to 58.6) | 467 (424.9 to 516.9) |
| 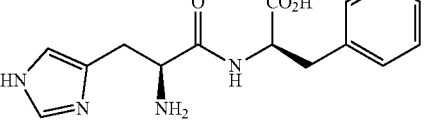 | His-Phe | 130.2 (113.5 to 150.1) | 573 (547.9 to 602.7) |
| 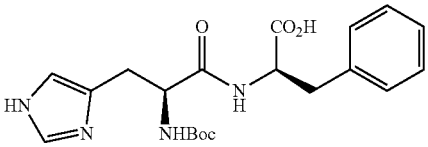 [SMILES: CC(C)(C)OC(=O)N[C@@H](Cc1c[nH]cn1)C(=O)N[C@H](Cc1ccccc1)C(=O)O] | NK-61-2A | Inactive | Inactive |
| 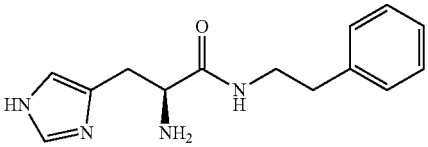 [SMILES: N[C@@H](Cc1c[nH]cn1)C(=O)NCCc1ccccc1] | NK-61-4A | 9.46 (5.9 to 15) | 231 (216.2 to 248.9) |
| 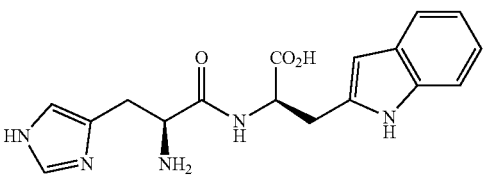 [SMILES: N[C@@H](Cc1c[nH]cn1)C(=O)N[C@H](Cc1cc2ccccc2[nH]1)C(=O)O] | His-Trp | 34 (24 to 48.12) | 440.3 (414.3 to 467.9) |

TABLE 2-continued

Structure, $A_{50}$ and $A_{max}$ activity data for synthesized dipeptide Neurolysin (Nln) activators.

| Compound | Code | $A_{50}$ (μM; 95% CI) | $A_{max}$ (%; 95% CI) |
|---|---|---|---|
| (His-NHBoc, amide-CH2CH2-indole) | PT-1-172 | Inactive | Inactive |
| (His-NH2, amide-CH2CH2-indole) | (±)PT-1-173 RACEMIC | 4.3 (3.4 to 5.4) | 311 (298.6 to 325.7) |
| (imidazole-CH2CH2-C(O)-NH-CH2CH2-indole) | PT-1-177 | Inactive | Inactive |
| (His-NH2, amide-CH2-phenyl) | DF-3-2B | 24.25 (7.85 to 71.4) | 152.2 (137.3 to 171.5) |
| (His-NH2, amide-CH2-C6H4-F) | DF-6-2A | 24.9 (15.7 to 39.5) | 252 (235.6 to 270.5) |
| (His-NH2, amide-phenyl) | DF-5-2A | 7.743 (0.66 to 46.8) | 139.8 (124.7 to 158.4) |
| (His-NHBoc, amide-CH2CH2-phenyl) | | Inactive | Inactive |
| (His-NHBoc, amide-CH2CH2-indole) | | Inactive | Inactive |

TABLE 2-continued
Structure, $A_{50}$ and $A_{max}$ activity data for synthesized dipeptide Neurolysin (Nln) activators.
| Compound | Code | $A_{50}$ (μM; 95% CI) | $A_{max}$ (%; 95% CI) |
|---|---|---|---|
| 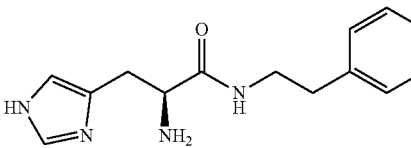 | DF-2-2B | 27.89 (22.4 to 34.8) | 323.1 (311.4 to 335.6) |
| 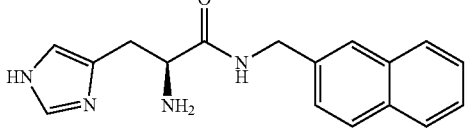 | DF-9-2 | 12.27 (7.6 to 19.7) | 262.3 (246.7 to 279.4) |
| 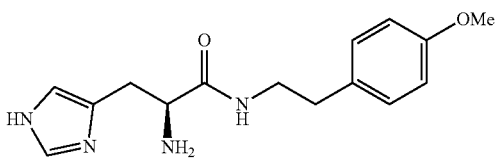 [SMILES: COc1ccc(CCNC(=O)[C@@H](N)Cc2c[nH]cn2)cc1] | AB-1-4-2 | 52.5 (34.5 to 81.3) | 544 (492.2 to 609.4) |
| 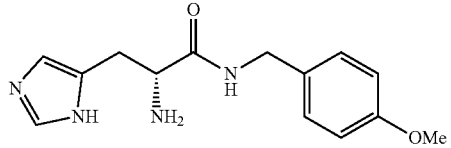 [SMILES: COc1ccc(CNC(=O)[C@H](N)Cc2cnc[nH]2)cc1] | AB-1-16-2 | 226.8 (146 to 392.4) | 703.5 (588.9 to 915.6) |
| 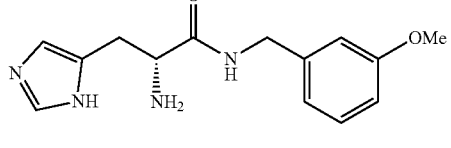 | AB-1-14-2 | 61.83 (46.5 to 83) | 477.1 (444 to 516) |
| 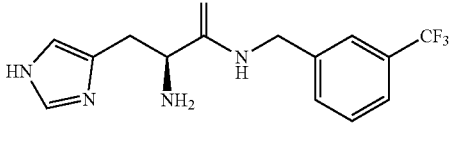 | AB-1-6-2 | 16 (13 to 19.7) | 494.4 (476.7 to 512.9) |
| 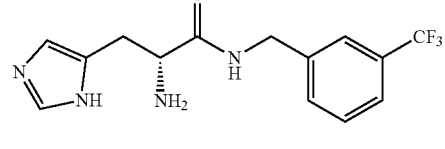 | AB-1-9-2 | 11.99 (4.9 to 27.3) | 184.4 (169.4 to 201.5) |
| 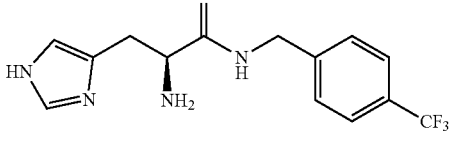 | DF-8-2 | 36.31 (25.3 to 52.5) | 305.2 (285.3 to 328) |
| 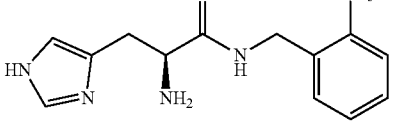 | DF-10-2 | 40.06 (29.4 to 55.12) | 334 (313.7 to 357.2) |

TABLE 2-continued

Structure, $A_{50}$ and $A_{max}$ activity data for synthesized dipeptide Neurolysin (Nln) activators.

| Compound | Code | $A_{50}$ (μM; 95% CI) | $A_{max}$ (%; 95% CI) |
|---|---|---|---|
| (structure) | AB-2-7-2 | 60.4 (46.2 to 79.8) | 407 (382.7 to 434.9) |
| (structure) | AB-1-3-2 | Inactive | Inactive |
| (structure) | AB 3-2-2 | 42.7 (21 to 89.8) | 438.4 (379.4 to 520.4) |
| (structure) | AB-1-8-2 | 157.6 (122.4 to 207.2) | 643 (588.8 to 714) |
| (structure) | AB1-17-2 | 139.5 (98.15 to 206.3) | 598.8 (532.8 to 692.9) |
| (structure) | HP2CF3 | 23.08 (19.6 to 27.2) | 396.2 (384.5 to 408.5) |
| (structure) | AB-2-5-4 | 5.4 (1.45 to 17.2) | 177.6 (158.7 to 198.1) |
| (structure) | His-Pro | 5.6 (4.7 to 6.7) | 502 (488.4 to 515.7) |

TABLE 2-continued
Structure, $A_{50}$ and $A_{max}$ activity data for synthesized dipeptide Neurolysin (Nln) activators.
| Compound | Code | $A_{50}$ (μM; 95% CI) | $A_{max}$ (%; 95% CI) |
|---|---|---|---|
| 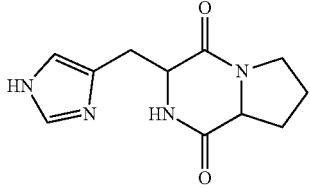 | Cyclo(His-Pro) | Inactive | Inactive |
| 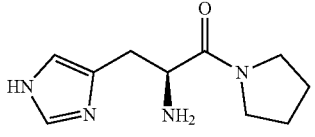 | SR-5-3d | 53 (28.5 to 106) | 173 (158.5 to 194.1) |
| 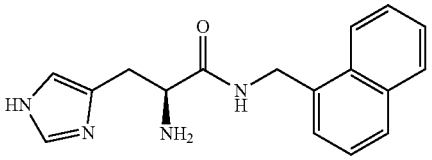 | SR-9-1d | 4.2 (3.17 to 5.6) | 264 (256.3 to 272.6) |
| 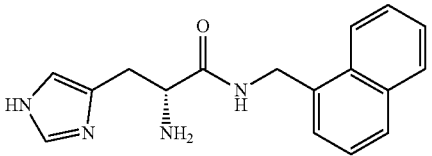 | SR-10-1d | 15.37 (10.9 to 21.5) | 343 (325.2 to 363.5) |
| 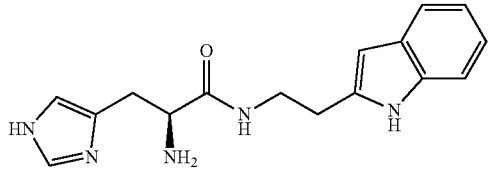 | SR-7-2d | 6.1 (3.7 to 10.12) | 259 (240.7 to 281) |
| 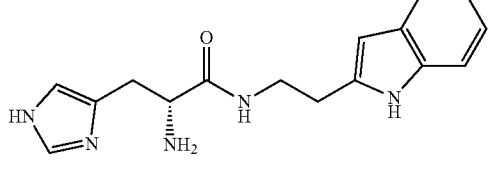 | SR-8-2d | 1.0 (0.16 to 4.4) | 132 (122.5 to 143.6) |
| 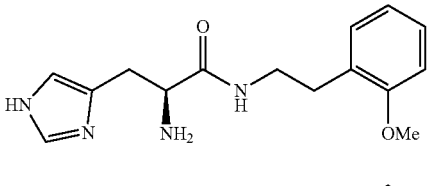 | SR11-1d | 31.8 (21 to 48.7) | 319 (296.1 to 345.4) |
| 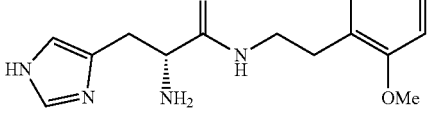 | SR12-1d | 30 (24 to 37.5) | 328 (315.4 to 342) |

TABLE 2-continued

Structure, $A_{50}$ and $A_{max}$ activity data for synthesized dipeptide Neurolysin (Nln) activators.

| Compound | Code | $A_{50}$ (μM; 95% CI) | $A_{max}$ (%; 95% CI) |
|---|---|---|---|
| (structure) | SR13-1d | 29.6 (22.7 to 38.8) | 367 (349.7 to 387.1) |
| (structure) | SR18-1 | 13.6 (10.1 to 18.2) | 323.7 (310.3 to 337.9) |
| (structure) | SR16-1d | 43.2 (30.9 to 61.5) | 324.9 (304 to 349) |
| (structure) | SR15-1d | 19.8 (9.5 to 40.6) | 255.3 (230.5 to 284.8) |
| (structure) | SR20-1d | 221 (149-354) | 428.8 (373 to 523.5) |
| (structure) | SR19-2d | 25.2 (19.6 to 32.4) | 339.8 (325.4 to 355.4) |

TABLE 3

The effect of top-ranking 40 compounds on catalytic activity of rat recombinant neurolysin.

| NSC # | 6088 | 615399 | 639022 | 640354 | 659264 | 296961 | 302851 | 332636 | 333568 | 339919 |
|---|---|---|---|---|---|---|---|---|---|---|
| Score ranking | 13, | 34 | 54 | 32 | 49 | 48 | 10, 27, | 46 | 23, 37 | 57 |
| % activity at 10 | 102 | 108 | 91 | 79 | 104 | 106 | 104 | 103 | 106 | 100 |
| % activity at 100 | 108 | 108 | 30 | 76 | 107 | 127 | 80 | 64 | 77 | 63 |

| NSC # | 35909 | 374121 | 400844 | 523374 | 600947 | 353874 | 211002 | 266752 | 281707 | 282137 |
|---|---|---|---|---|---|---|---|---|---|---|
| Score ranking | 5 | 35 | 30 | 7, 9, 22, | 11, 45, | 2 | 15 | 59, 83 | 14 | 36 |
| % activity at 10 | 87 | 121 | 104 | 122 | 107 | 122 | 104 | 107 | 109 | 106 |
| % activity at 100 | 92 | 226 | 84 | 206 | 105 | 80 | 100 | 97 | 113 | 94 |

TABLE 3-continued

The effect of top-ranking 40 compounds on catalytic activity of rat recombinant neurolysin.

| NSC # | 343 | 14541 | 15180 | 47096 | 134514 | 155877 | 163084 | 203396 | 210826 | 48778 |
|---|---|---|---|---|---|---|---|---|---|---|
| Score ranking | 20 | 6 | 42 | 43, 99 | 21, 25, | 8 | 12 | 16 | 53 | 18, 73 |
| % activity at 10 | 105 | 97 | 102 | 101 | 92 | 82 | 103 | 102 | 101 | 89 |
| % activity at 100 | 106 | 103 | 95 | 111 | 9 | 4 | 102 | 106 | 105 | 84 |
| NSC # | 820 | 88659 | 89624 | 92597 | 121184 | 128977 | 131922 | 134119 | 340049 | 343028 |
| Score ranking | 17 | 50 | 19, 38 | 51, 64 | 24 | 3 | 26, 39, | 31 | 33, 52 | 28, 29 |
| % activity at 10 | 105 | 100 | 102 | 105 | 77 | 80 | 96 | 83 | 94 | 98 |
| % activity at 100 | 100 | 100 | 38 | 98 | 18 | 68 | 28 | 41 | 52 | 73 |

*, compared to vehicle control.

Synthesis Scheme

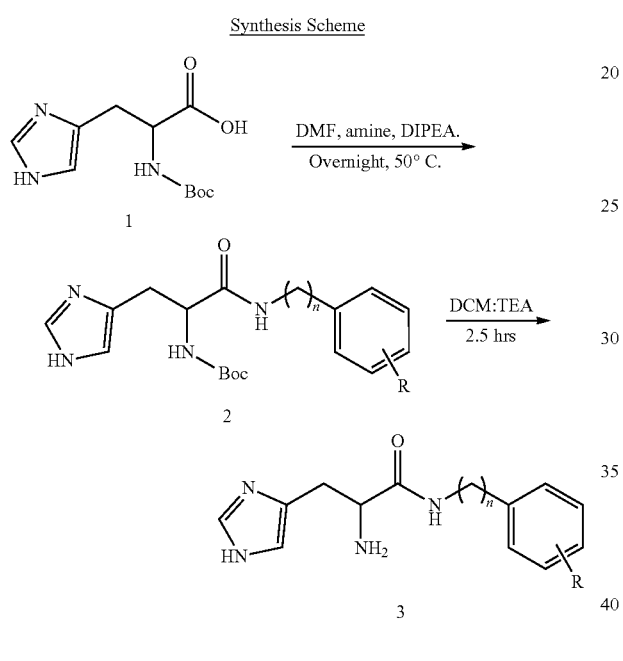

General Synthetic Procedures. All reactions were carried out in oven dried glassware under positive nitrogen pressure. Reaction progress was monitored by thin-layer chromatography (TLC) and visualized by using UV lamp (254 nm), or by ninhydrin, potassium permanganate or phosphomolybdic acid solutions as indicator. Column chromatography was performed with silica gel using the mobile phase indicated. Commercial grade solvents and reagents were purchased from Fisher Scientific or Sigma-Aldrich and were used without further purification except as indicated. Anhydrous solvents were purchased from Across Organics and stored under an atmosphere of dry nitrogen over molecular sieves. 1H and 13C NMR spectra were recorded in the indicated solvent on a Bruker 400 MHz Avance III HD spectrometer at 400 and 100 MHz for 1H and 13C, respectively, with deuterated solvent peaks as internal standard. Multiplicities are indicated by s (single), d (doublet), dd (doublet of doublets), t (triplet), q (quartet), m (multiplet), and br (broad). Chemical shifts (δ) are reported in parts per million (ppm) and coupling constants (J), in hertz. High-pressure liquid chromatography was performed on a Gilson HPLC system, equipped with 254 UV detector using Trilution software v.2.1 with an ACE Equivalence 3 (C18, 3 mm, 4.6 mm×150 mm) column. All samples were determined to possess >95% purity, except where indicated otherwise.

General method to synthesize di- and tripeptides: To a solution of N-Boc-L-Histidine (1 mmol) in DMF (6 mL) was added BOP (1 mmol) and the solution stirred at for 30 minutes at 50° C. under an atmosphere of nitrogen. In a separate vessel, DIPEA (1 equiv.) was added dropwise to a solution of the appropriate amine (1 equiv.) in DMF (4 mL) and the mixture stirred at room temperature for 30 minutes under an atmosphere of nitrogen. The contents of this vessel were added dropwise to the mixture of N-Boc-L-Histidine (1 equiv.) and BOP and the reaction stirred for 30 minutes at 50° C. The reaction was extracted with EtOAc and washed with water. The organic phase was dried (Na2SO4), evaporated in vacuo and purified by column chromatography (1%-7% MeOH:DCM). The crude product was dissolved in 20% TFA in DCM (20 mL) and stirred for 3 hours at room temperature. The solvent was evaporated in vacuo to yield the title compound.

AB-1-4-2

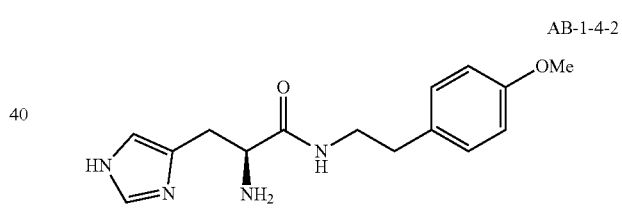

$^1$H (DMSO-d$_6$, 400 Hz) δ$_H$: 2.61 (2H, t, J=7.2 Hz, CH$_2$), 3.10-3.14 (2H, m, CH$_2$), 3.24-3.27 (1H, m, CH), 3.33-3.38 (1H, m, CH), 2.95 (3H, s, OCH$_3$), 4.02-4.08 (1H, m, CH), 6.85 (2H, d, J=8.4 Hz, Ar—H), 7.10 (2H, d, J=8.0 Hz, Ar—H), 7.39 (1H, s, CH), 8.34-8.41 (2H, br. s, NH2), 8.54 (1H, t, J=5.4 Hz, NH), 9.01 (1H, s, CH), 14.31-14.80 (1H, br. s, NH). $^{13}$C (DMSO-d$_6$, 100 Hz) δ$_C$: 27.0, 34.3, 41.1, 51.8, 55.4, 114.2, 118.2, 127.5, 129.9, 131.2, 134.9, 158.2, 167.4

AB-1-16-2

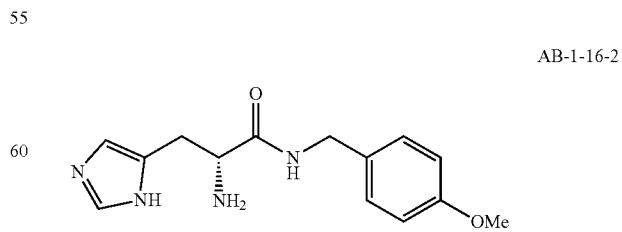

$^1$H (DMSO-d$_6$, 400 Hz) δ$_H$: 3.11-3.23 (2H, m, CH$_2$), 3.74 (3H, s, OCH$_3$), 4.09 (1H, t, J=7.2 Hz, CH), 4.19-4.29 (2H, m, CH$_2$), 6.88 (2H, d, J=8.8 Hz, Ar—H), 7.09 (2H, d, J=8.0

Hz, Ar—H), 7.41 (1H, s, CH), 8.39-8.45 (2H, br. s, NH2), 8.86 (1H, t, J=5.6 Hz, NH), 9.01 (1H, s, CH), 14.3-14.62 (1H, br. s, NH).

$^{13}$C (DMSO-d$_6$, 100 Hz) δ$_C$: 26.9, 42.3, 51.8, 55.5, 114.1, 118.3, 129.1, 130.4, 134.8, 158.8, 167.3.

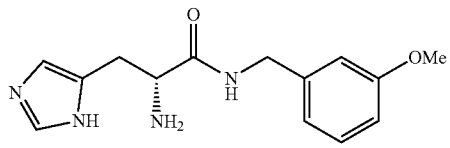 [SMILES: COc1cccc(CNC(=O)[C@H](N)Cc2cnc[nH]2)c1]

AB-1-14-2

$^1$H (DMSO-d$_6$, 400 Hz) δ$_H$: 3.14-3.26 (2H, m, CH$_2$), 3.73 (3H, s, OCH$_3$), 4.17 (1H, t, J=6.2 Hz, CH), 4.28-4.31 (2H, m, CH$_2$), 6.73-6.84 (3H, m, Ar—H), 7.23 (1H, t, Ar—H), 7.42 (1H, s, CH), 8.45-8.47 (2H, br. s, NH2), 8.98 (1H, t, J=5.6 Hz, NH), 9.04 (1H, s, CH), 14.55-14.66 (1H, br. s, NH).

$^{13}$C (DMSO-d$_6$, 100 Hz) δc: 26.8, 42.8, 51.8, 55.4, 112.8, 113.6, 118.3, 119.8, 127.7, 129.9, 134.8, 140.1, 159.7, 167.5.

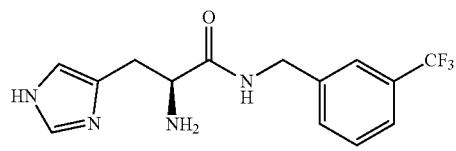 [SMILES: N[C@@H](Cc1c[nH]cn1)C(=O)NCc1cccc(C(F)(F)F)c1]

AB-1-6-2

$^1$H (DMSO-d$_6$, 400 Hz) δ$_H$: 3.15-3.28 (2H, m, CH$_2$), 4.20 (1H, t, J=6.8 Hz, CH), 4.35-4.50 (2H, m, CH$_2$), 7.42 (1H, s, CH), 7.50 (1H, d, J=7.6 Hz, Ar—H), 7.55-7.64 (3H, m, Ar—H), 8.45-8.48 (2H, br. s, NH2), 9.03 (1H, s, CH), 9.10 (1H, t, J=5.6 Hz, NH), 14.49-14.67 (1H, br. s, NH).

$^{13}$C (DMSO-d$_6$, 100 Hz) δ$_C$: 26.9, 42.5, 51.9, 118.2, 124.2, 127.5, 129.3, 129.8, 130.1, 131.9, 134.9, 140.2, 159, 167.8

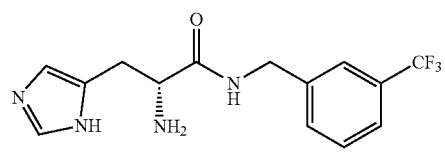 [SMILES: N[C@H](Cc1cnc[nH]1)C(=O)NCc1cccc(C(F)(F)F)c1]

AB-1-9-2

$^1$H (DMSO-d$_6$, 400 Hz) δ$_H$: 3.16-3.29 (2H, m, CH$_2$), 4.21 (1H, t, J=6.6 Hz, CH), 4.35-4.49 (2H, m, CH$_2$), 7.42 (1H, s, CH), 7.49 (1H, d, J=7.6 Hz, Ar—H), 7.54-7.63 (3H, m, Ar—H), 8.48-8.52 (2H, br. s, NH2), 9.03 (1H, s, CH), 9.14 (1H, t, J=5.8 Hz, NH), 14.69-14.81 (1H, br. s, NH).

$^{13}$C (DMSO-d$_6$, 100 Hz) δ$_C$: 26.8, 42.5, 51.8, 118.3, 124.4, 127.2, 129.8, 130.1, 131.8, 133.6, 134.9, 135.8, 140.2, 159.1, 167.8.

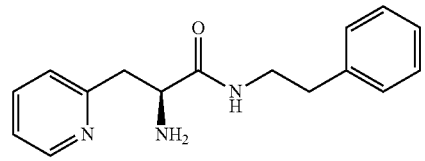 [SMILES: N[C@@H](Cc1ccccn1)C(=O)NCCc1ccccc1]

AB-1-3-2

$^1$H (DMSO-d$_6$, 400 Hz) δ$_H$: 2.66 (2H, t, J=7.4 Hz), 3.22-3.40 (4H, m, 2×CH$_2$), 4.23 (1H, t, J=6.8 Hz, CH), 7.16-7.22 (4H, m, Ar—H), 7.26-7.30 (2H, m, Ar—H), 7.52 (1H, d, J=8.0 Hz, Ar—H), 7.61 (1H, t, J=6.0 Hz, Ar—H), 8.10 (1H, t, J=7.2 Hz, NH), 8.48-8.49 (2H, br. s, NH2), 8.68 (1H, d, J=4.0 Hz, Ar—H).

$^{13}$C (DMSO-d$_6$, 100 Hz) δ$_C$: 35.5, 42.3, 54.9, 60.2, 122, 124.3, 126.5, 128.7, 136.6, 139.8, 149.3, 158.7, 170.7.

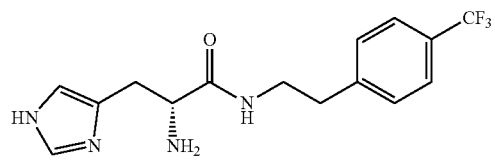 [SMILES: N[C@H](Cc1c[nH]cn1)C(=O)NCCc1ccc(C(F)(F)F)cc1]

AB-1-8-2

$^1$H (DMSO-d$_6$, 400 Hz) δ$_H$: 2.79 (2H, t, J=7.2 Hz, CH$_2$), 3.03-3.16 (2H, m, CH$_2$), 3.31-3.47 (2H, m, CH$_2$), 4.04 (1H, t, J=6.8 Hz, CH), 7.37 (1H, s, CH), 7.40 (2H, d, J=8.0 Hz, Ar—H), 7.63 (2H, d, J=8.0 Hz, Ar—H), 8.28-8.43 (2H, br. s, NH2), 8.58 (1H, t, J=5.6 Hz, NH), 8.91 (1H, s, CH), 14.22-14.60 (1H, br. s, NH).

$^{13}$C (DMSO-d$_6$, 100 Hz) δ$_C$: 27.1, 34.9, 51.8, 118.1, 125.5, 127.3, 127.5, 129.9, 135, 144.4, 158.9, 167.6.

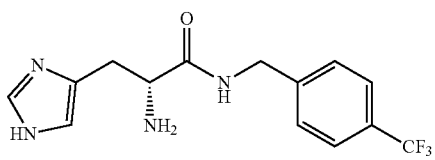 [SMILES: N[C@H](Cc1c[nH]cn1)C(=O)NCc1ccc(C(F)(F)F)cc1]

AB-17-2

$^1$H (DMSO-d$_6$, 400 Hz) δ$_H$: 3.14-3.26 (2H, m, CH$_2$), 4.21 (1H, t, J=6.8 Hz, CH), 4.43-4.54 (2H, m, CH$_2$), 7.36 (1H, d, J=8.0 Hz, Ar—H), 7.42 (1H, s, CH), 7.50 (1H, t, J=7.6 Hz, Ar—H), 7.64 (1H, t, J=7.6 Hz, Ar—H), 7.73 (1H, d, J=7.6 Hz, Ar—H), 8.48-8.56 (2H, br. s, NH2), 8.94 (1H, s, CH), 9.06 (1H, t, J=5.6 Hz, NH), 14.34-14.59 (1H, br. s, NH).

$^{13}$C (DMSO-d$_6$, 100 Hz) δ$_C$: 27, 52, 118.2, 126.2, 126.6, 128.3, 129.4, 130.8, 133.1, 135, 136.6, 158.6, 167.9.

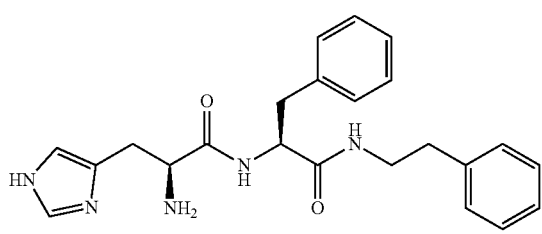 [SMILES: N[C@@H](Cc1c[nH]cn1)C(=O)N[C@@H](Cc1ccccc1)C(=O)NCCc1ccccc1]

AB-2-5-4

¹H (DMSO-d₆, 400 Hz) δ_H: 2.67 (2H, t, J=7.4 Hz, CH₂), 2.79-2.84 (1H, m, CH), 2.93-2.98 (1H, m, CH), 3.07-3.10 (1H, m, CH), 3.20-3.27 (2H, m, CH₂), 3.27-3.34 (1H, m, CH), 4.14 (1H, s, CH), 4.50 (1H, q, J=8.4 Hz, CH), 7.19-7.31 (10H, m, Ar—H), 7.42 (1H, s, CH), 8.25-8.28 (2H, br. s, NH2), 8.46 (1H, t, J=5.1 Hz, NH), 8.73 (1H, d, J=7.6 Hz, NH), 9.04 (1H, s, CH), 14.32-14.41 (1H, br. s, NH).

¹³C (DMSO-d₆, 100 Hz) δ_C: 26.8, 35.3, 37.9, 46.2, 51.4, 55.2, 118.7, 126.6, 127, 128.6, 128.7, 129.1, 129.5, 134.9, 137.6, 139.6, 167.7, 171.4.

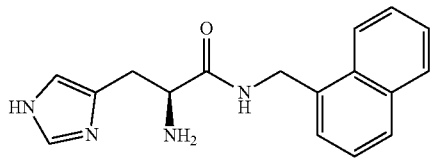 [SMILES: N[C@@H](Cc1c[nH]cn1)C(=O)NCc1cccc2ccccc12]

SR 8-2d

¹H NMR (400 MHz, MeOH-d₄) δ_H: 2.82-3.07 (m, 2H), 3.10-3.30 (m, 2H), 3.52 (dt, J=13.4, 6.8 Hz, 1H), 3.58-3.74 (m, 1H), 4.00-4.21 (m, 1H), 6.89-7.05 (m, 1H), 7.05-7.16 (m, 2H), 7.16-7.29 (m, 1H), 7.30-7.42 (m, 1H), 7.48-7.70 (m, 1H), 8.69 (br. s, 1H).

¹³C NMR (100 MHz, MeOH-d₄) δ_C: 13.05, 19.47, 24.59, 40.05, 51.91, 60.15, 110.95, 111.31, 117.80, 118.30, 121.06, 122.19, 127.24, 134.30, 136.74, 167.03.

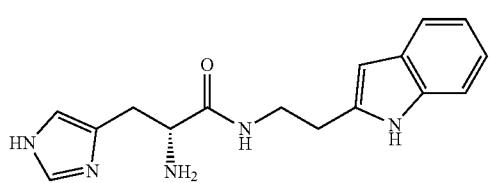

SR 9-1d

¹H NMR (400 MHz, MeOH-d₄) δ_H: 3.29 (dd, J=7.0, 2.9 Hz, 2H), 4.21 (t, J=7.1 Hz, 1H), 4.78 (d, J=14.67 Hz, 1H), 7.20 (s, 1H), 7.40-7.50 (m, 2H), 7.50-7.62 (m, 2H), 7.82-7.89 (m, 1H), 7.89-7.96 (m, 1H), 7.96-8.05 (m, 1H), 8.62 (s, 1H).

¹³C NMR (100 MHz, MeOH-d₄) δ_C: 26.47, 41.00, 51.99, 117.67, 122.92, 125.05, 125.64, 126.17, 126.62, 128.30, 128.52, 131.14, 132.85, 133.97, 134.21, 166.76.

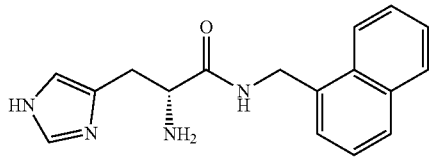 [SMILES: N[C@H](Cc1c[nH]cn1)C(=O)NCc1cccc2ccccc12]

SR 10-1d

¹H NMR (400 MHz, MeOH-d₄) δ_H: 3.24-3.31 (m, 2H), 4.23 (t, J=6.8 Hz, 1H), 4.77 (d, J=14.7 Hz, 1H), 4.96 (d, J=14.7 Hz, 2H), 7.19 (s, 1H), 7.38-7.48 (m, 2H), 7.48-7.57 (m, 2H), 7.78-7.85 (m, 1H), 7.95-8.02 (m, 1H), 8.61 (s, 1H).

¹³C NMR (100 MHz, MeOH-d₄) δ_C: 26.32, 40.98, 51.94, 117.83, 122.92, 125.05, 125.63, 126.17, 126.59, 126.83, 128.27, 128.49, 131.13, 132.86, 133.95, 134.10, 166.76.

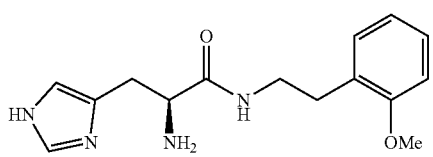 [SMILES: COc1ccccc1CCNC(=O)[C@@H](N)Cc1c[nH]cn1]

SR 11-1d

¹H NMR (400 MHz, MeOH-d₄) δ_H: 2.57-2.79 (m, 2H), 3.03-3.20 (m, 2H), 3.23-3.31 (m, 1H), 3.35-3.47 (m, 1H), 3.72 (s, 3H), 4.03 (t, J=6.7 Hz, 1H), 6.74 (t, J=7.4 Hz, 1H), 6.82 (d, J=8.2 Hz, 1H), 6.99 (d, J=7.2 Hz, 1H), 7.09 (t, J=7.3 Hz, 1H), 7.20 (s, 1H) 8.74 (s, 1H).

¹³C NMR (100 MHz, MeOH-d₄) δ_C: 26.38, 29.81, 39.19, 51.94, 54.38, 69.94, 110.17, 118.00, 120.11, 126.53, 126.98, 127.71, 130.00, 134.44, 157.68, 166.98.

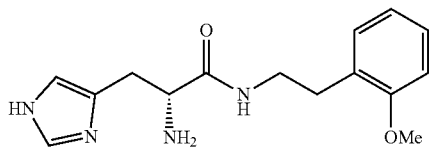 [SMILES: COc1ccccc1CCNC(=O)[C@H](N)Cc1c[nH]cn1]

SR 12-1d

¹H NMR (400 MHz, MeOH-d₄) δ_H: 2.57-2.77 (m, 2H), 3.03-3.20 (m, 2H), 3.24-3.35 (m, 1H), 3.35-3.46 (m, 1H), 3.67-3.76 (m, 3H), 4.02 (t, J=6.9 Hz, 1H), 6.68-6.78 (m, 1H), 6.83 (d, J=8.1 Hz, 1H), 6.95-7.03 (m, 1H), 7.04-7.15 (m, 1H), 7.20 (s, 1H), 8.75 (s, 1H).

¹³C NMR (100 MHz, MeOH-d₄) δ_C: 26.47, 29.81, 39.19, 51.98, 54.37, 110.17, 117.90, 120.11, 126.52, 127.18, 127.71, 130.00, 134.48, 157.67, 167.01.

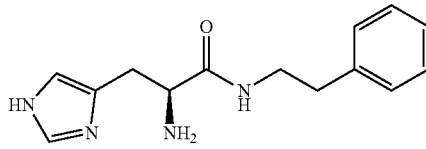

SR 13-1d

¹H NMR (400 MHz, MeOH-d₄) δ_H: 2.58-2.72 (m, 2H), 3.01-3.18 (m, 2H), 3.27-3.48 (m, 2H), 3.67 (s, 4H), 4.02 (t, J=6.9 Hz, 1H), 6.60-6.72 (m, 3H), 7.01-7.15 (m, 1H), 7.21 (s, 1H), 8.68-8.77 (m, 1H).

$^{13}$C NMR (100 MHz, MeOH-d$_4$) δ$_C$: 26.48, 34.79, 40.57, 51.96, 54.21, 111.43, 114.12, 117.88, 120.63, 127.17, 129.19, 134.50, 140.17, 159.93, 167.08.

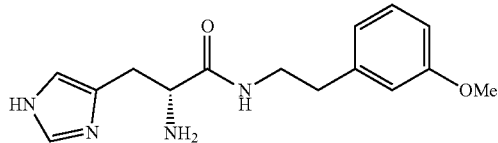

SR 15-1d $^1$H NMR (400 MHz, MeOH-d$_4$) δ$_H$: 2.67-2.85 (m, 2H), 3.28 (dd, J=6.7, 3.7 Hz, 2H), 3.44 (dt, J=13.5, 6.9 Hz, 1H), 3.55 (dd, J=14.2, 6.9 Hz, 1H), 3.81 (s, 3H), 4.17 (t, J=6.9 Hz, 1H), 6.74-6.89 (m, 3H), 7.17-7.32 (m, 2H), 8.66-8.75 (m, 1H).
$^{13}$C$^{NMR}$ (100 MHz, MeOH-d$_4$) δ$_C$: 26.42, 34.79, 40.57, 51.91, 54.19, 111.42, 114.09, 117.94, 120.63, 127.03, 129.19, 134.49, 140.17, 159.93, 167.07.

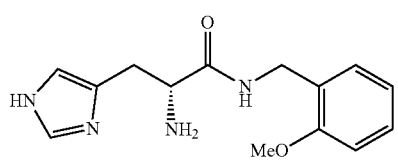

SR 16-1d $^1$H NMR (400 MHz, MeOH-d$_4$) δ$_H$: 3.02-3.31 (m, 2H), 3.78-3.89 (m, 3H), 4.24 (d, J=14.6 Hz, 2H), 4.46 (d, J=14.4 Hz, 1H), 6.95 (t, J=7.3 Hz, 1H), 7.01 (d, J=8.2 Hz, 1H), 7.10-7.22 (m, 2H), 7.34 (t, J=7.8 Hz, 1H), 8.49 (br. s, 1H).
$^{13}$C NMR (100 MHz, MeOH-d$_4$) δ$_C$: 26.39, 38.74, 52.10, 54.91, 110.59, 117.78, 120.34, 124.97, 129.29' 129.36, 134.07, 157.32, 167.16.

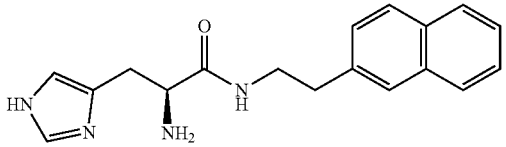 [SMILES: N[C@@H](Cc1c[nH]cn1)C(=O)NCCc1ccc2ccccc2c1]

SR 18-1d $^1$H NMR (400 MHz, MeOH-d$_4$) δ$_H$: 2.88-3.08 (m, 2H), 3.09-3.31 (m, 2H), 3.47-3.75 (m, 3H), 4.15 (br. s, 1H), 7.24 (s, 1H), 7.32-7.53 (m, 3H), 7.59-7.72 (m, 1H), 7.72-7.88 (m, 3H), 8.70 (s, 1H).
$^3$C NMR (100 MHz, MeOH-d$_4$) δ$_C$: 26.42, 34.92, 40.49, 51.81, 117.84, 125.17, 125.76, 126.76, 126.78, 127.06, 127.23, 127.80, 132.35, 133.61, 134.33, 136.17.

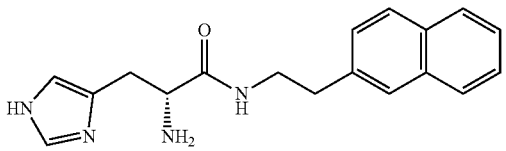 [SMILES: N[C@H](Cc1c[nH]cn1)C(=O)NCCc1ccc2ccccc2c1]

SR 19-2d $^1$H NMR (400 MHz, MeOH-d$_4$) δ$_H$: 2.91-3.05 (m, 2H), 3.06-3.26 (m, 2H), 3.49-3.73 (m, 2H), 4.11 (t, J=6.6 Hz, 1H), 7.19 (s, 1H), 7.34-7.42 (m, 1H), 7.42-7.48 (m, 2H), 7.69 (s, 1H), 7.74-7.86 (m, 3H), 8.55 (s, 1H).
$^{13}$C NMR (100 MHz, MeOH-d$_4$) δ$_C$: 26.33, 34.91, 40.49, 51.77, 117.92, 125.17, 125.75, 126.69, 126.76, 126.78, 127.06, 127.23, 127.80, 132.34, 133.61, 134.27, 136.17, 167.09.

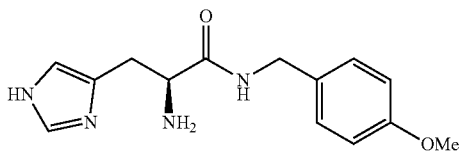

SR 20-1d $^1$H NMR (400 MHz, MeOH-d$_4$) δ$_H$: 3.24-3.31 (m, 2H), 3.77-3.84 (m, 3H), 4.14 (t, J=7.0 Hz, 1H), 4.27 (d, J=14.6 Hz, 1H), 4.38 (d, J=14.4 Hz, 1H), 6.89 (m, 2H), 7.17 (m, 2H), 7.30 (s, 1H), 8.73 (s, 1H).
$^{13}$C NMR (100 MHz, MeOH-d$_4$) δ$_C$: 26.43, 42.47, 52.08, 54.29, 113.58, 117.88, 127.21, 128.89, 129.66, 134.39, 159.26, 166.71.

Figure 2A:
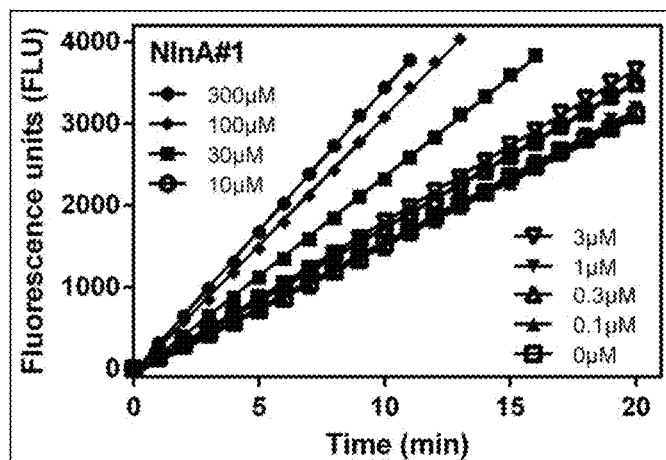
Figure 2B:
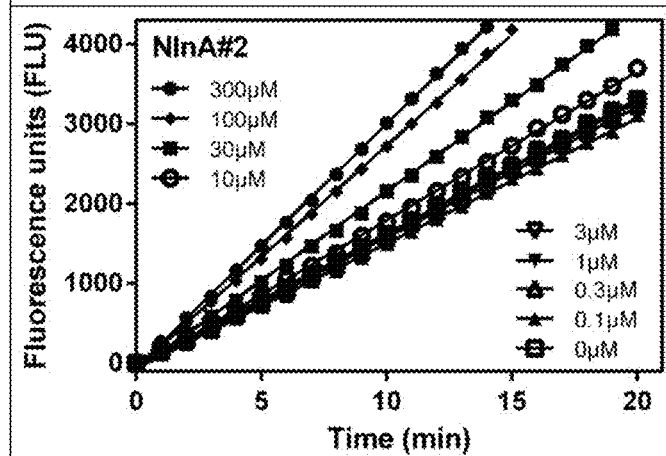
Figure 2C:
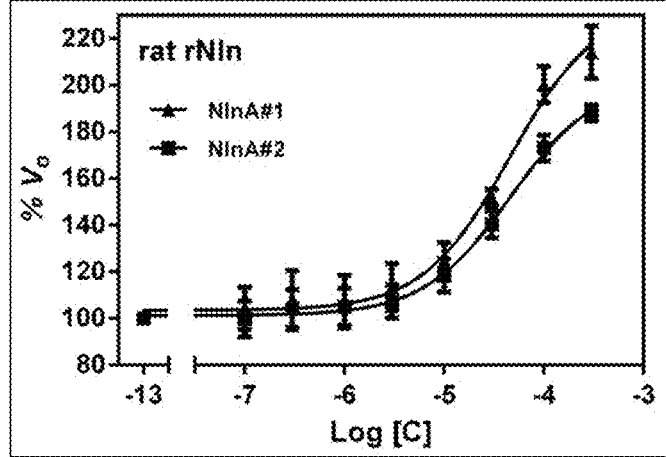

Based on the results of the primary screen, compounds NSC 374121 (referred as NlnA #1) and NSC 523374 (referred as NlnA #2) were subjected to further pharmacological evaluation. Concentration-dependent effect of both compounds on initial velocity of hydrolysis of QFS by neurolysin is presented in FIGS. 2A to 2C. For NlnA #1 (FIG. 2A) the calculated average EC$_{50}$ was 45.4 μM (95% confidence intervals 29.9 to 68.9 μM), and E$_{max}$ was 234.7% (95% confidence intervals 219.0 to 250.4%). For NlnA #2 (FIG. 2B) the calculated average EC$_{50}$ was 45.8 μM (95% confidence intervals 32.0 to 65.6 μM), and E$_{max}$ was 202.8% (95% confidence intervals 192.2 to 213.4%).

Figure 10A:
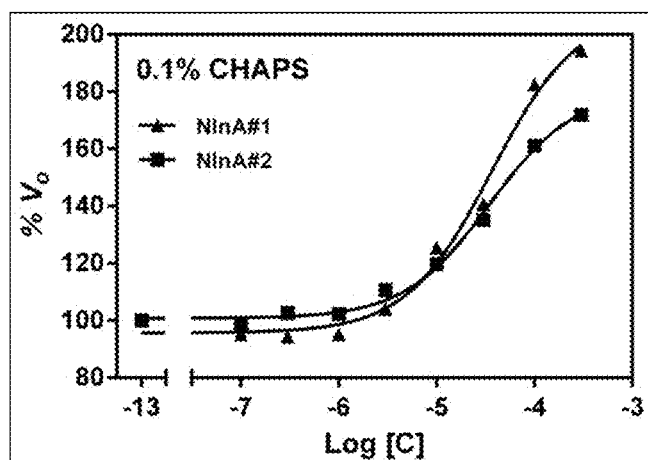
FIGS. 10A and 10B show the effect of compounds NlnA #1 and NlnA #2 on catalytic activity of neurolysin in the presence of CHAPS (FIG. 10A) and BSA (FIG. 10B). Both panels document representative concentration-dependent effect of the compounds on hydrolysis of QFS (25 µM) by rat recombinant neurolysin (0.3 nM). The initial velocity of the hydrolysis in the absence of either compound corresponds to 100% on the vertical axis and to −13 on the horizontal axis. In the presence of 0.1% CHAPS, $EC_{50}$ value for NlnA #1 is 36.2 µM (95% confidence intervals 22.2 to 59.3 M), whereas for NlnA #2 it is 34.5 M (95% confidence intervals 24.3 to 49.2 µM). In the presence of 0.01 mg/ml BSA, $EC_{50}$ value for NlnA #1 is 20.5 µM (95% confidence intervals 9.0 to 47.1 µM), whereas for NlnA #2 it is 30.6 µM (95% confidence intervals 10.6 to 87.8 µM).
Figure 10B:
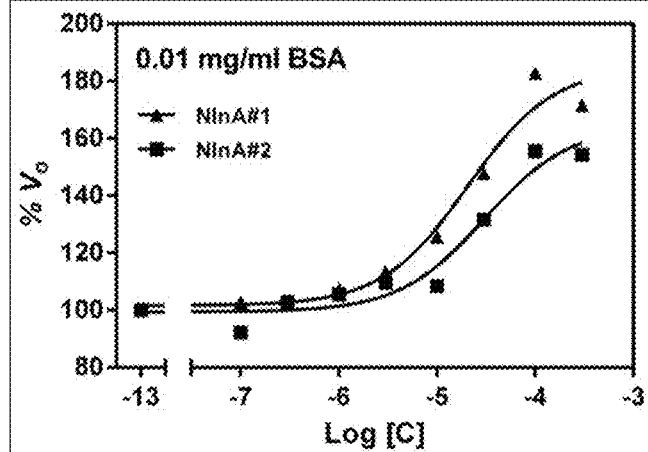
Figure 11A:
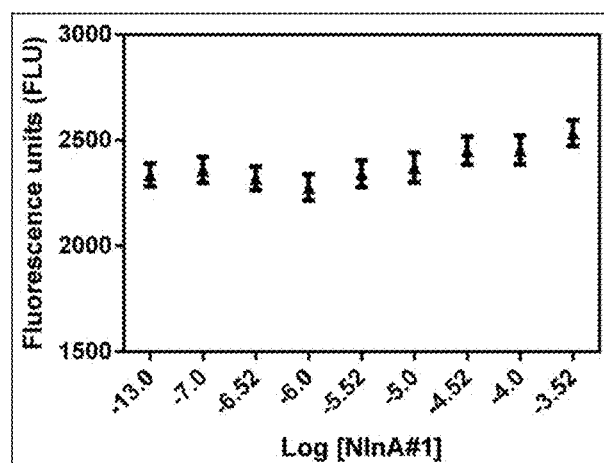
FIGS. 11A and 11B show the effect of compounds NlnA #1 (FIG. 11A) and NlnA #2 (FIG. 11A) on fluorescence signal of Mca-Pro-Leu-OH. Both panels document representative concentration-dependent effect of the compounds on fluorescence signal of Mca-Pro-Leu-OH, the product of QFS hydrolysis by neurolysin, under the same assay conditions as presented in FIGS. 2A-C. The only difference was that Mca-Pro-Leu-OH, instead of QFS, was present in the assay at 2 µM final concentration. Each data point represents the average fluorescence signal measured every minute for duration of 10 min. Note that −13 on the horizontal axis corresponds to the condition where neither NlnA #1 nor NlnA #2 was present.
Figure 11B:
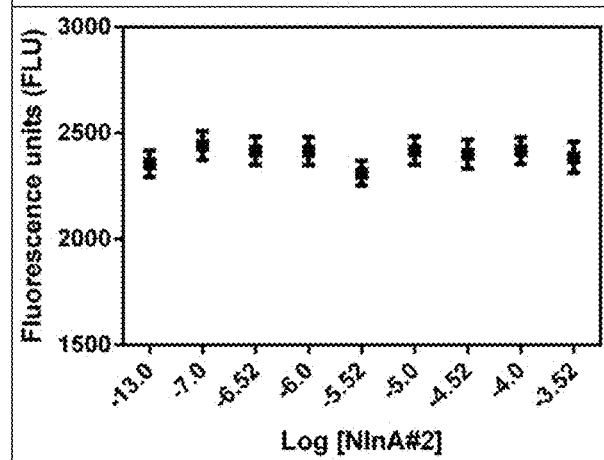

Notably, both the primary screen and the concentration-response experiments were carried out in an assay buffer containing 0.01% Triton X-100, as recommended by Feng B. and colleagues (44,45), to avoid identification of promiscuous modulators of enzymes. In addition, the concentration-response experiment was also conducted in the presence of 0.1% CHAPS or 0.01 mg/ml bovine serum albumin (BSA), as alternatives to Triton X-100, to prevent identification of non-specific enzyme modulators (46). In the latter experiments, both compounds demonstrated concentration-dependent effect on activity of neurolysin similar to the condition where Triton X-100 was present in the assay buffer (FIGS. 10A and 10B). The inherent fluorescent enhancing or quenching properties of NlnA #1 and NlnA #2 were also verified to avoid false conclusions. In this set of experiments it was determined that the compounds had negligible or no effect of on the fluorescence signal documented from the hydrolysis product of QFS (Mca-Pro-Leu-OH; (36)) under the same experimental conditions (FIGS. 11A and 11B). Lastly, activity of neurolysin could be enhanced by NlnA #1 and NlnA #2 purchased from a commercial vendor (AnaSpec), as well as in several independently produced and isolated batches of the rat recombinant neurolysin (data not shown). Based on these results it was concluded that enhancement of neurolysin activity by NlnA #1 and NlnA #2 was not an artifact and pharmacological studies were continued.

The modulatory site on neurolysin is different from the substrate binding site—To confirm that NlnA #1 and NlnA

Figure 3:
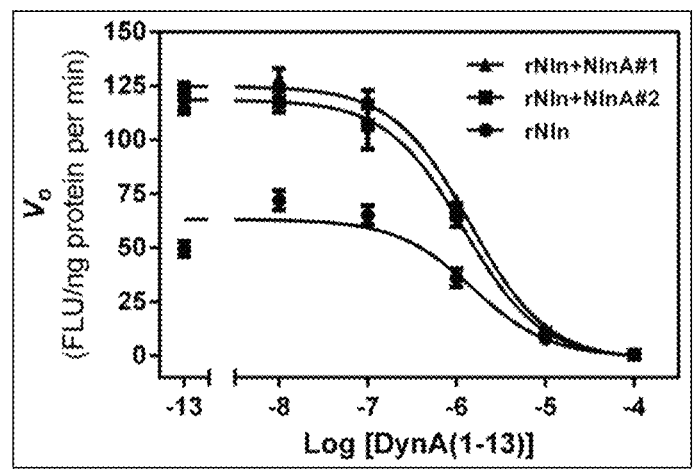
Figure 4A:
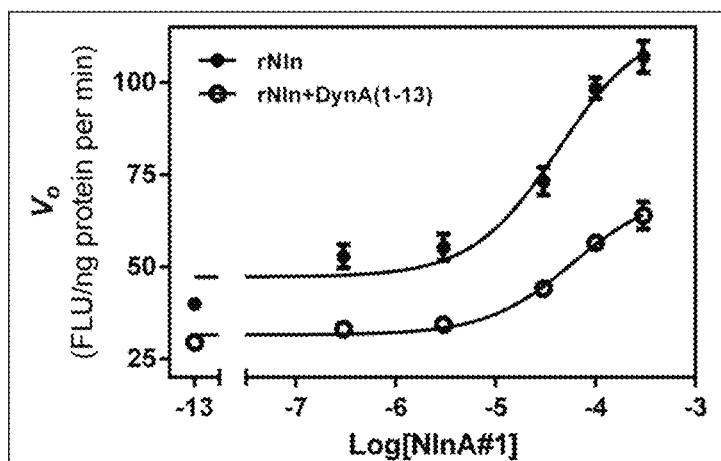
FIGS. 4A and 4B show the effect of dynorphin A (1-13) on the potency of compounds NlnA #1 (FIG. 4A) and NlnA #2 (FIG. 4B). Concentration-dependent effect of NlnA #1 and NlnA #2 on hydrolysis of QFS (15 µM) by rat recombinant neurolysin (rNln, ~0.3 nM) in the absence or presence of dynorphin A (1-13) (1 µM) (n=3, mean±SD are presented, FLU—fluorescence unit). Note that the initial velocity of the hydrolysis in the absence of NlnA #1 or NlnA #2 corresponds to −13 on the horizontal axis in both panels. Calculated $EC_{50}$ values for NlnA #1 are 42.3 µM (95% CI: 24.0-74.8 M) and 58.6 M (95% CI 37.5-91.6 M) in the absence and presence of dynorphin A (1-13), respectively. Corresponding $E_{max}$ values for NlnA #1 are 292.4% (95% confidence intervals 265.7 to 319.0%) and 238.3% (95% confidence intervals 222.2 to 254.3%). Calculated $EC_{50}$ values for NlnA #2 are 23.3 µM (95% CI: 6.7-81.2 µM) and 24.9 µM (95% CI: 8.4-73.5 µM) in the absence and presence of dynorphin A (1-13), respectively. Corresponding $E_{max}$ values for NlnA #2 are 254.7% (95% confidence intervals 226.3 to 283.1%) and 198.3% (95% confidence intervals 179.5 to 217.0%).
Figure 4B:
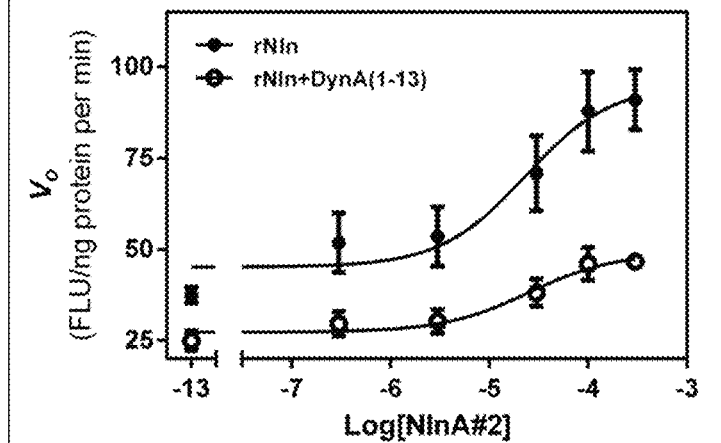

2 were interacting with a binding site on neurolysin that was different from the substrate binding site, a set of experiments were carried out using a competitive inhibitor of neurolysin dynorphin A(1-13) (47). In the first experiment, the effect of a fixed concentration of NlnA #1 and NlnA #2 on the affinity of dynorphin A(1-13), i.e. Ki value, in inhibiting activity of neurolysin was determined (FIG. 3). As expected, both NlnA #1 and NlnA #2 enhanced activity of neurolysin, and this effect was also observed in the presence of dynorphin A(1-13) at concentrations close to its $IC_{50}$ value and below. However, Ki values for dynorphin A(1-13) did not differ significantly in the absence and presence of the modulators (FIG. 3): Ki value was 0.76 µM (95% CI: 0.45-1.25 µM) in the absence of any of the modulators, it was 0.7 µM (95% CI: 0.55-0.9 µM) in the presence of 100 µM NlnA #1, and 0.6 µM (95% CI: 0.45-0.75 µM) in the presence of 100 µM NlnA #2. In a reverse experiment, the concentration-response effect of NlnA #1 and NlnA #2 on activity of neurolysin were studied in the absence and presence of a fixed concentration of dynorphin A(1-13) (FIGS. 4A and 4B). In these experiments, dynorphin A(1-13) inhibited activity of neurolysin and decreased the $E_{max}$ values of NlnA #1 (FIG. 4A) and NlnA #2 (FIG. 4B). However, it did not significantly affect the $EC_{50}$ values of the modulators (FIGS. 4A and 4B): $EC_{50}$ value for NlnA #1 was 42.3 µM (95% CI: 24.0-74.8 µM) and 58.6 µM (95% CI: 37.5-91.6 µM) in the absence and presence of dynorphin A (1-13), respectively. $EC_{50}$ value for NlnA #2 was 23.3 µM (95% CI: 6.7-81.2 µM) and 24.9 µM (95% CI: 8.4-73.5 µM) in the absence and presence of dynorphin A(1-13), respectively. The observations made in this set of experiments suggest that dynorphin A(1-13) and NlnA #1 or NlnA #2 interact with different binding sites on neurolysin, because they did not affect each other's affinity for the peptidase (FIGS. 3 and 4A/4B). Although, the $EC_{50}$ value is a not a direct indicator of the affinity of a ligand, in these experiments where all variables were maintained unchanged (concentrations of neurolysin, substrate, NlnA #1, NlnA #2, etc.) the documented $EC_{50}$ values of the modulators in the absence and presence of dynorphin A(1-13) suggest that affinity of the modulators for neurolysin remained unaffected. Considering that dynorphin A(1-13) is a competitive inhibitor of neurolysin (47), these data also suggest that the binding site of the modulators is different from the substrate binding site.

Figure 5A:
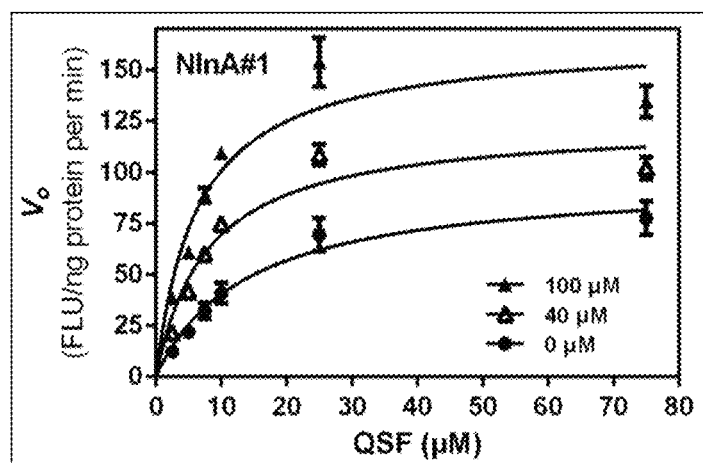
FIGS. 5A and 5B show the effect of compounds NlnA #1 (FIG. 5A) and NlnA #2 (FIG. 5B) on catalytic efficiency of neurolysin. Hydrolysis of different concentrations of QFS by rat recombinant neurolysin (0.3 nM) in the absence or presence of NlnA #1 and NlnA #2 (40 and 100 µM) is presented (n=16 for 0 µM (neurolysin alone), n=4 for all other groups, mean±SD are presented, FLU—fluorescence unit).
Figure 5B:
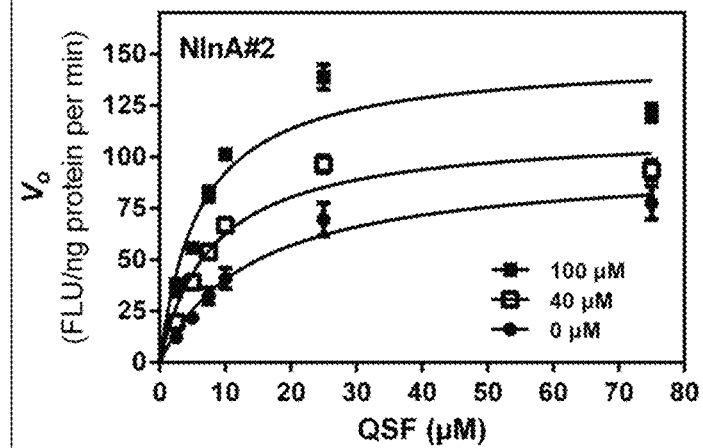

Effect of the modulators on catalytic efficiency of neurolysin—To determine whether the increased initial velocity of QFS hydrolysis by neurolysin in the presence of NlnA #1 or NlnA #2 translates into increased catalytic efficiency of the peptidase, in this set of experiments the effect of both modulators on hydrolysis of different concentrations of the substrate (spanning from ~6-fold less to ~5-fold more of its Km value) was studied. In the presence of NlnA #1 at a concentration close to its $EC_{50}$ value (40 µM) maximal velocity (Vmax) of the hydrolysis was increased by ~29%, whereas Km value was decreased by ~43% resulting in more than doubling of Vmax/Km ratio (FIGS. 5A and 5B and Table 3). Likewise, in the presence of NlnA #2 (40 µM) $V_{max}$ value was increased by ~16.5%, whereas Km value was decreased by ~42.4%, again resulting in doubling of the Vmax/Km ratio (FIGS. 5A and 5B and Table 3). The same trend was observed in the presence of 100 µM concentration of either modulators resulting in more than tripling of the Vmax/Km ratio (FIGS. 5A and 5B and Table 3). These data suggest that both NlnA #1 and NlnA #2 increased catalytic efficiency of neurolysin. These experiments also allowed us to define the kinetic mechanism of neurolysin activation by NlnA #1 and NlnA #2. Since catalysis of the reaction by neurolysin occurs both in the absence and presence of the modulators, NlnA #1 and NlnA #2 can be classified as non-essential activators (48). Considering that the modulators affect both Km and Vmax values of the substrate hydrolysis by neurolysin, they can be classified as allosteric effectors of the "K system" and "V system", which may indicate that both substrate-binding affinity ("K-systems") and the rate of substrate conversion into product ("V-systems") are altered (49).

TABLE 4

Calculated Vmax and Km values for studies presented in FIGS. 5A and 5B.

| | Vmax | Km | Vmax/K | Fold change |
|---|---|---|---|---|
| rNln | 96.6 (91.3-101.8) | 13.9 (12.0-15.8) | 6.9 | — |
| rNln + 40 µM NlnA#1 | 124.2*** (112.2-136.2) | 7.9*** (5.7-10.1) | 15.7 | 2.3 |
| rNln + 100 µM NlnA#1 | 164.8*** (147.2-182.4) | 6.4*** (4.3-8.5) | 25.8 | 3.7 |
| rNln + 40 µM NlnA#2 | 112.5* (102.7-122.3) | 8.0*** (6.0-10.0) | 14.0 | 2.0 |
| rNln + 100 µM NlnA#2 | 148.2*** (133.0-163.3) | 6.1*** (4.1-8.0) | 24.4 | 3.5 |

Vmax unites are in FLU/ng protein per min, Km units are in µM (FLU-fluorescent unit).
Data are presented as average values together with 95% confidence intervals in parenthesis (n = 16 for recombinant neurolysin (rNln), n = 4 for all other groups;
*p < 0.05;
***p < 0.001 in comparison to rNln values).

Figure 6A:
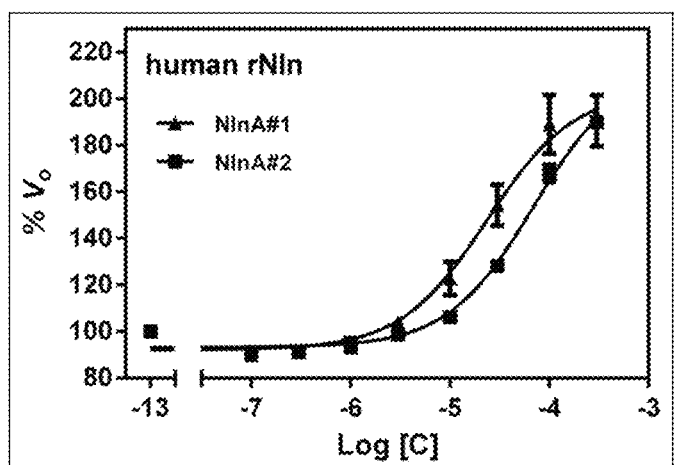
FIGS. 6A and 6B show the effect of compounds NlnA #1 (FIG. 6A) and NlnA #2 (FIG. 6B) on catalytic activity of human recombinant and mouse brain neurolysin. Both panels document concentration-dependent effect of both compounds on hydrolysis of QFS at 25 µM (n=3, mean±SD are presented). Note that the initial velocity of the hydrolysis in the absence of either compound corresponds to 100% on the vertical axis and to −13 on the horizontal axis. In human recombinant neurolysin the $EC_{50}$ for NlnA #1 is 23.6 µM (95% confidence intervals 16.5 to 33.7 µM), and $E_{max}$ is 203.5 (95% confidence intervals 193.7 to 213.4%). The $EC_{50}$ value for NlnA #2 is 69.5 µM (95% confidence intervals 56.0 to 86.2 µM), and $E_{max}$ is 214.3% (95% confidence intervals 205.7 to 222.9%). In mouse brain neurolysin the $EC_{50}$ for NlnA #1 is 9.2 µM (95% confidence intervals 3.1 to 26.9 µM), and $E_{max}$ is 190% (95% confidence intervals 169.2 to 210.7%). The $EC_{50}$ value for NlnA #2 is 17.1 µM (95% confidence intervals 6.0 to 49.1 µM), and $E_{max}$ is 258% (95% confidence intervals 232.7 to 283.8%). Note that in the mouse brain neurolysin, the initial velocity of QFS hydrolysis was consistently lower in the presence of 300 µM NlnA #1 compared to that of 100 µM (300 µM concentration was not included in the analysis for determination of the $EC_{50}$ value).
Figure 6B:
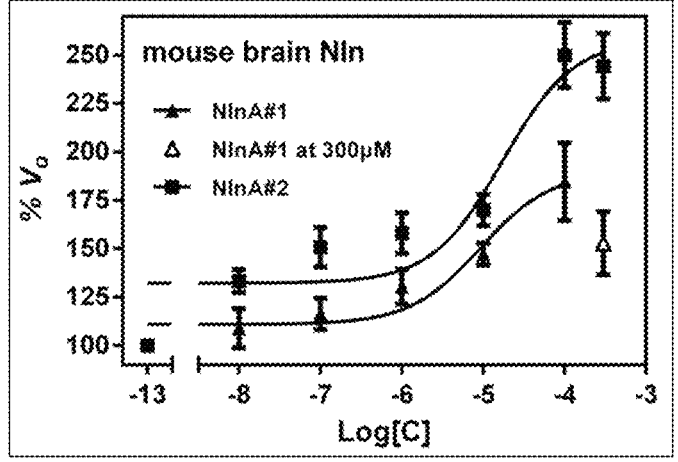

Species selectivity of the identified modulators—To determine whether the observed effects of NlnA #1 and NlnA #2 are only limited to the rat neurolysin or not, concentration response studies were also carried out with human recombinant and mouse brain-purified neurolysin. Concentration-dependent effects of both compounds on initial velocity of hydrolysis of QFS by human and mouse neurolysin were similar to that of the rat peptidase, and are presented in FIGS. 6A and 6B. With human recombinant neurolysin the calculated average $EC_{50}$ for NlnA #1 (FIG. 6A) was 23.6 µM (95% confidence intervals 16.5 to 33.7 µM), and Emax was 203.5% (95% confidence intervals 193.7 to 213.4%). For NlnA #2 (FIG. 6B) the calculated average $EC_{50}$ was 69.5 µM (95% confidence intervals 56.0 to 86.2 µM), and Emax was 214.3% (95% confidence intervals 205.7 to 222.9%). With mouse brain neurolysin the calculated average $EC_{50}$ for NlnA #1 was 9.2 µM (95% confidence intervals 3.1 to 26.9 µM), and Emax was 190% (95% confidence intervals 169.2 to 210.7%). For NlnA #2 the calculated average $EC_{50}$ was 17.1 µM (95% confidence intervals 6.0 to 49.1 µM), and Emax was 258% (95% confidence intervals 232.7 to 283.8%). These observations indicate that both modulators enhance activity of human recombinant and mouse brain neurolysins similar to that of the rat recombinant peptidase, with NlnA #1 being somewhat more potent than NlnA #2. Importantly, the ability of the modulators to enhance activity of native, i.e., mouse brain-purified, neurolysin also indicates that our observations are not limited to the recombinantly produced peptidase and that the allosteric site is the same/similar in these species.

Peptidase selectivity of the identified modulators—In this set of experiments concentration-dependent effects of NlnA #1 and NlnA #2 on activity of peptidases related to neurolysin were studied (FIGS. 7A to 7D). Overall, both modulators demonstrated negligible effect on activity of thimet oligopeptidase (TOP, FIG. 7A), angiotensin converting enzyme (ACE, FIG. 7B), ACE2 and neprilysin (NEP, FIG. 7D) at concentrations up to 300 µM. At 300 µM concentration NlnA #1 inhibited activity of TOP by 25.9±0.7%, ACE by 22.6±2.5%, ACE2 (FIG. 7C) by 13.4±2.9%, and NEP by 2.9±4.7% (n=3, mean±SD are presented). Under the same experimental conditions, NlnA #2 (at 300 µM) inhibited activity of TOP by 15.6±2.6%, ACE by 12.2±1.8%, ACE2 by 10.9±2.9%, and NEP by 1.6±2.0% (n=3, mean±SD are presented). Although, the list of tested peptidases was not exhaustive and it did not include many other pharmacological targets, the negligible effect of NlnA #1 and NlnA #2 on activity of four closely related peptidases, including TOP— the closest homolog to neurolysin (50), suggests that the modulators possessed excellent selectivity towards neurolysin and did not promiscuously enhance activity of peptidases.

Effect of modulators on hydrolysis of endogenous substrates by neurolysin—The use of synthetic substrates (usually with fluorescent properties) in enzymatic assays to identify and characterize modulators is very convenient as they allow easy tracking of the reaction progress (17). However, observations made with such substrates cannot be translated a priori to the endogenous substrates, as there are examples in the scientific literature describing compounds which could modulate the target enzyme only when a synthetic substrate was used (51,52). To avoid such artifacts, in this set of studies the effect of NlnA #1 and NlnA #2 on hydrolysis of three endogenous substrates of neurolysin (angiotensin I, bradykinin and neurotensin (26,47)) were studied, and mass-spectrometry was used to document the reaction (FIG. 8 and Supplementary FIG. 3). In the presence of both modulators formation of angiotensin-(1-7) from angiotensin I was increased by ~6-fold, formation of bradykinin-(1-5) from bradykinin by ~2-fold, and formation of neurotensin-(1-10) from neurotensin by ~3-fold. These results provide additional evidence that catalytic activity of neurolysin can be enhanced by NlnA #1 and NlnA #2, and importantly, that this phenomenon is not limited to QFS but is also observed with endogenous substrates of the peptidase.

Figure 9B:
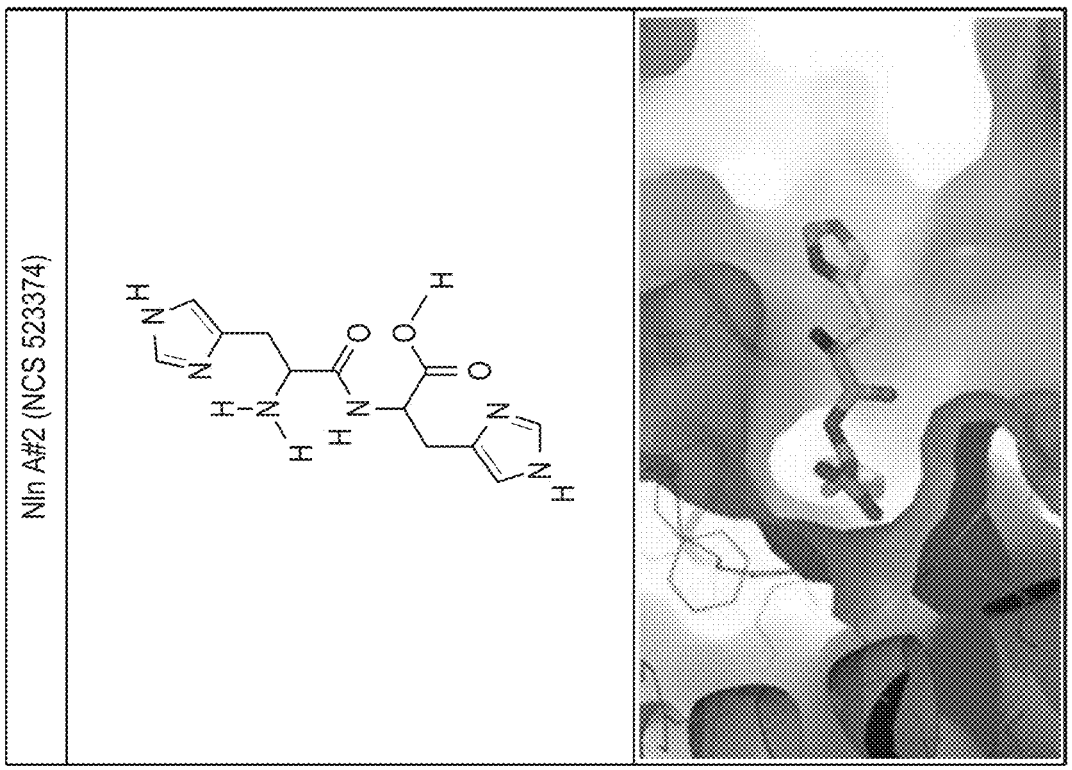
FIGS. 9A and 9B show the docking of NlnA #1 (FIG. 9A) and NlnA #2 (FIG. 9B) into the selected surface pocket of neurolysin in its hinge region. Top panels: chemical structure of the compounds. NlnA #1, NSC 374121, L-histidyl-L-tyrosine. NlnA #2, NSC 523374, D,L-histidyl-D,L-histidine. Bottom panels: close-up view of the crystal structure of neurolysin in its open conformation shown in FIG. 1B together with a molecule of NlnA #1 or NlnA #2 bound to the selected surface pocket, i.e. the hypothesized allosteric binding site. The molecular surface of the protein is colored gold for carbon, blue for nitrogen, red for oxygen. In the compounds, yellow for carbon, red for oxygen, and blue for nitrogen.
Figure 9A:
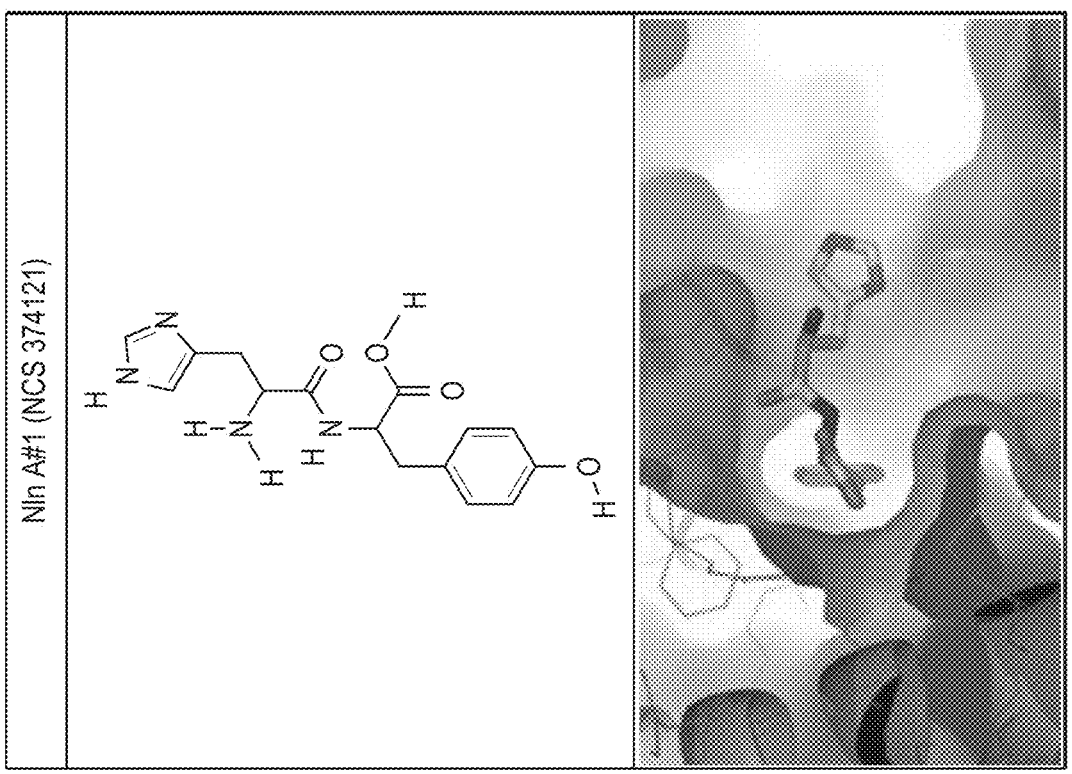

Structural analysis—Comparison of the structures of the identified modulators suggest chemical groups functionally relevant to the activity modulating mechanism. As shown in FIGS. 9A and 9B, top panels, NlnA #1 (L-histidyl-L-tyrosine) and NlnA #2 (D,L-histidyl-D,L-histidine) are largely identical, with common core structures linked to an imidazole ring. These common elements have the potential to either interact with the hinge region of neurolysin (and other sites) or be solvent accessible. Molecular docking of the modulators shows possible binding interactions with the hinge region of neurolysin (FIGS. 9A and 9B, bottom panels). The top scoring orientations of these compounds, as predicted by molecular docking, show common binding modes in which the common carboxylate groups have the potential to form H bonds with neurolysin. The predicted binding modes suggest that the imidazole group may be solvent accessible and available to participate in interactions with neighboring hinge residues.

The present inventors identified and characterized two structurally related compounds that enhance the catalytic efficiency of metallopeptidase neurolysin. To accomplish this a rational, structure-based drug-discovery approach was used involving structural analysis of the hinge region of neurolysin to identify a potential allosteric binding site with druggable properties, followed by docking and in silico screening of ~140,000 drug-like compounds from NCI DTP. The compounds were ranked based on their combined energy scores for hydrogen bonding and van der Waals contact interactions with the hypothesized allosteric binding site, and the highest ranking 40 compounds were subjected to thorough in vitro pharmacological evaluation. In the primary screen the effect of these compounds on activity of rat recombinant neurolysin was evaluated at 10 and 100 µM concentrations, resulting in identification of two modulators, which can increase the rate of hydrolysis of a synthetic substrate by neurolysin. Potencies of the identified modulators, i.e., $EC_{50}$ values determined from concentration-response studies, were ~45 µM with Emax values ≥200% for hydrolysis of the synthetic substrate by rat recombinant neurolysin. The observed effects were reproducible in an assay buffer supplemented with 0.01% Triton X-100, or 0.1% CHAPS or 0.01 mg/ml BSA, all of which are methodological tactics recommended by different investigators as a way to prevent identification of promiscuous modulators of enzymes in high or low-throughput screening studies. Notably, the observation was reproduced in different isolates of the rat recombinant neurolysin and with the identified modulators purchased from a commercial vendor instead of the stock obtained from NCI DTP. Both modulators were also capable of enhancing activity of human recombinant and mouse brain purified neurolysin, indicating that the effect of modulators was not limited to one species or to a recombinantly produced peptidase. To verify whether the identified modulators interacted with a binding site different from the substrate binding site or not, concentration-response experiments were carried out involving the modulators and dynorphin A(1-13), a competitive inhibitor of neurolysin. These studies show that neither the modulators nor dynorphin A(1-13) affected each other's affinity in modulating activity of neurolysin, providing evidence that the modulators bind to a site which is different from the substrate binding site. The effect of identified modulators on catalytic efficiency of neurolysin was determined using ranging concentrations of the synthetic substrate. Both modulators reduced Km and increased Vmax values, thus increasing Vmax/Km ratio, in a concentration-dependent manner, indicating that catalytic efficiency of neurolysin is enhanced by the modulators. On the contrary, the modulators had negligible or no effect on catalytic activity of peptidases closely related to neurolysin, including thimet oligopeptidase, neprilysin, angiotensin converting enzyme (ACE) and ACE2, indicating that the effect of the identified molecules is specific to neurolysin. Lastly, to determine whether the effect of the identified modulators on activity of neurolysin was observed only with the synthetic substrate or not, hydrolysis of three endogenous substrates of the peptidase was studied. These studies demonstrate that both modulators enhanced hydrolysis of neurotensin, bradykinin and angiotensin I by neurolysin, showing that the effect of the identified modulators was specific to the peptidase and not linked to the synthetic substrate only.

FIGS. 10A and 10B show the effect of compounds NlnA #1 and NlnA #2 on catalytic activity of neurolysin in the presence of CHAPS (FIG. 10A) and BSA (FIG. 10B). Both panels document representative concentration-dependent effect of the compounds on hydrolysis of QFS (25 µM) by rat recombinant neurolysin (0.3 nM). The initial velocity of the hydrolysis in the absence of either compound corresponds to 100% on the vertical axis and to ~13 on the horizontal axis. In the presence of 0.1% CHAPS, $EC_{50}$ value for NlnA #1 is 36.2 µM (95% confidence intervals 22.2 to 59.3 µM), whereas for NlnA #2 it is 34.5 µM (95% confidence intervals 24.3 to 49.2 µM). In the presence of 0.01 mg/ml BSA, $EC_{50}$ value for NlnA #1 is 20.5 µM (95% confidence intervals 9.0 to 47.1 µM), whereas for NlnA #2 it is 30.6 µM (95% confidence intervals 10.6 to 87.8 µM).

FIGS. 11A and 11B show the effect of compounds NlnA #1 (FIG. 11A) and NlnA #2 (FIG. 11A) on fluorescence signal of Mca-Pro-Leu-OH. Both panels document representative concentration-dependent effect of the compounds on fluorescence signal of Mca-Pro-Leu-OH, the product of QFS hydrolysis by neurolysin, under the same assay conditions as presented in FIGS. 2A-C. The only difference was that Mca-Pro-Leu-OH, instead of QFS, was present in the assay at 2 µM final concentration. Each data point represents the average fluorescence signal measured every minute for duration of 10 min. Note that −13 on the horizontal axis corresponds to the condition where neither NlnA #1 nor NlnA #2 was present.

Figure 12:
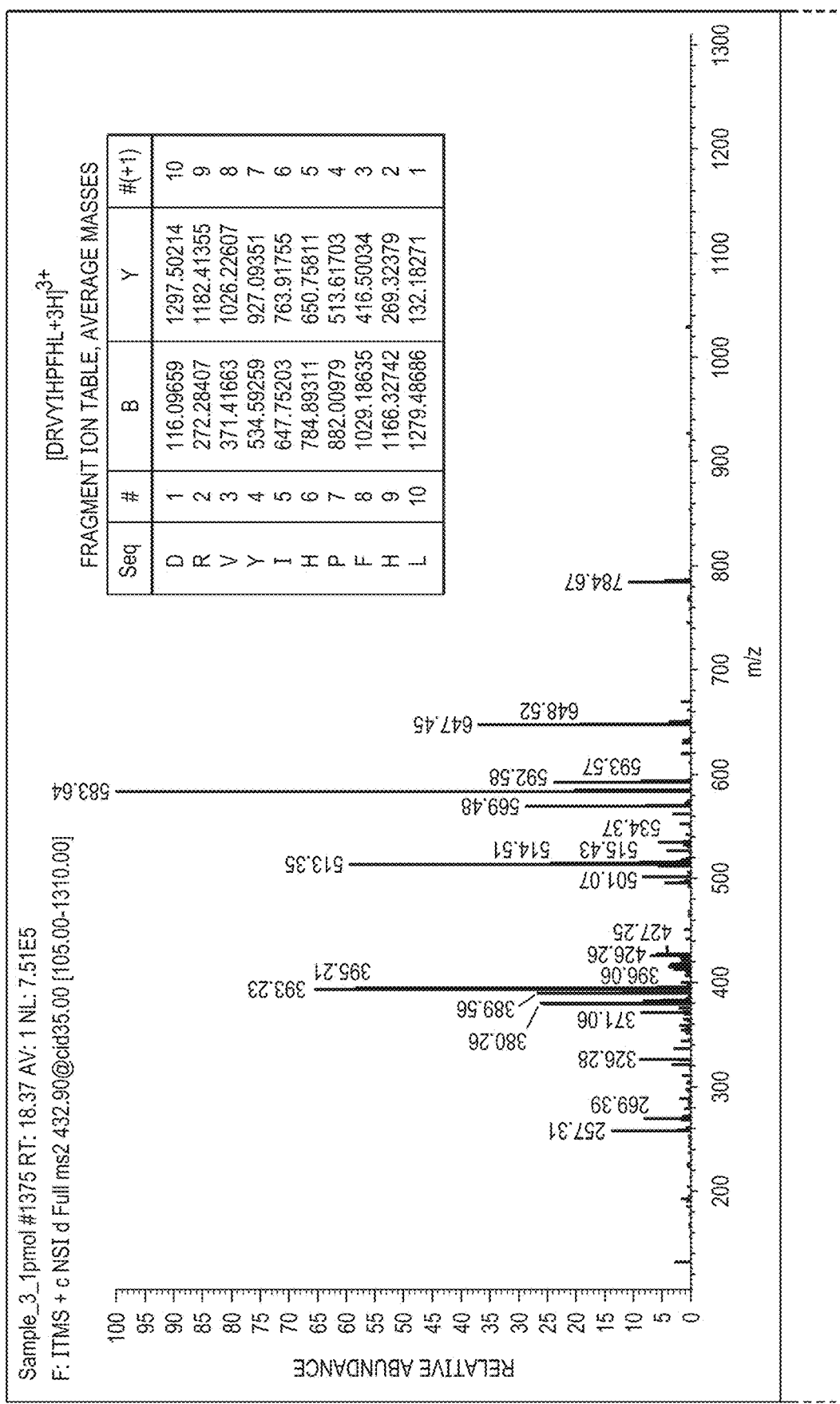
FIG. 12 shows a mass spectrometry analysis of angiotensin I hydrolysis by recombinant neurolysin. Top and middle panels demonstrate representative mass spectra of neurolysin substrate angiotensin I and the product of its hydrolysis angiotensin-(1-7), respectively. Bottom panel demonstrates representative LC-MS chromatograms of experimental samples in which angiotensin-(1-7) ([DRVYIHP+3H]$^{3+}$, m/z=300.4960) was measured for quantification.
Figure 12:
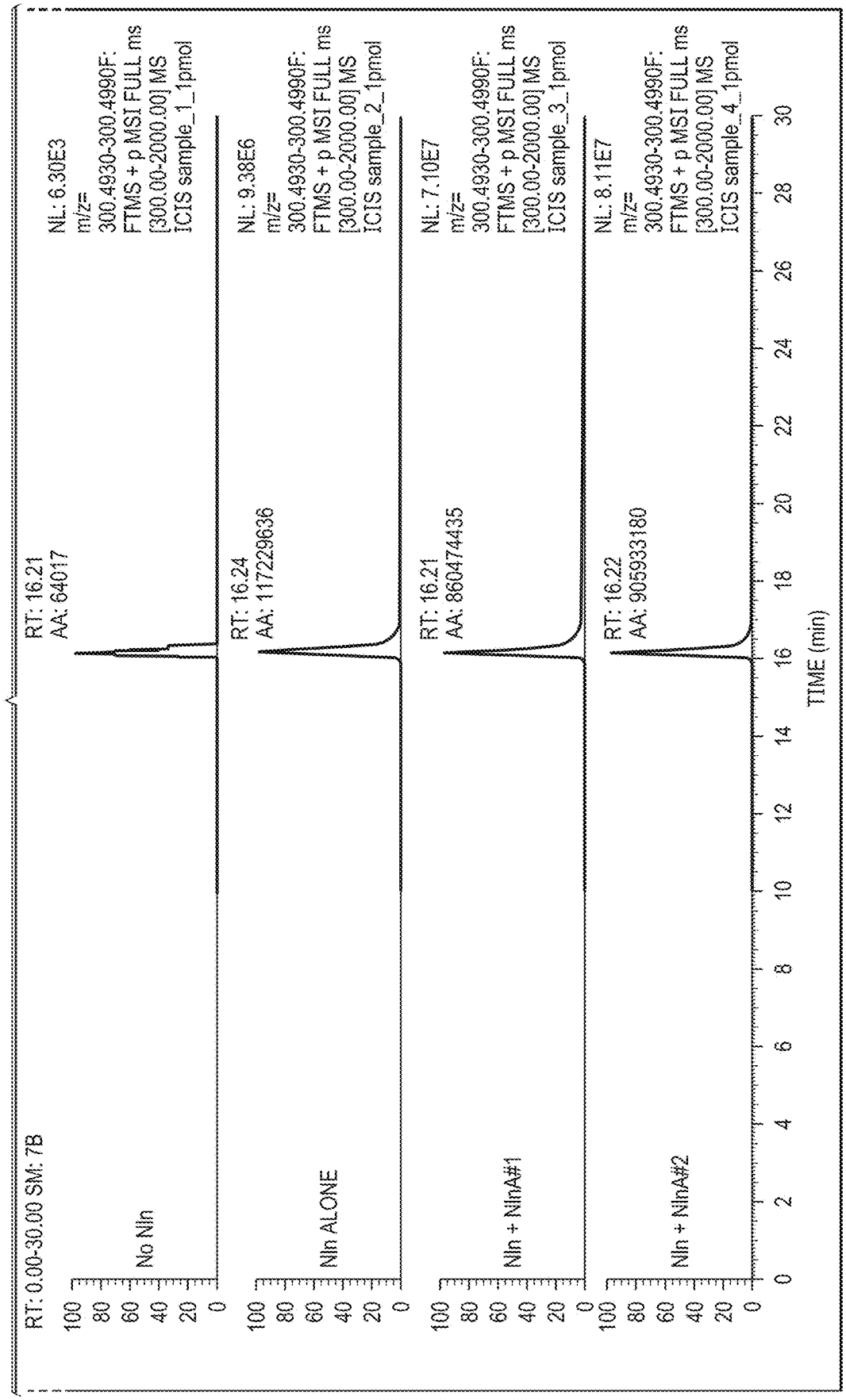

FIG. 12 shows a mass spectrometry analysis of angiotensin I hydrolysis by recombinant neurolysin. Top and middle panels demonstrate representative mass spectra of neurolysin substrate angiotensin I and the product of its hydrolysis angiotensin-(1-7), respectively. Bottom panel demonstrates representative LC-MS chromatograms of experimental samples in which angiotensin-(1-7) ($[DRVYIHP+3H]^{3+}$, m/z=300.4960) was measured for quantification.

This is the first report describing the discovery of specific, small molecule enhancers of neurolysin activity. These molecules can be used to target neurolysin in different (patho)physiological states. The structures are the lead molecules for development of an entirely new class of drugs, i.e., neurolysin potentiators/activators. The latter can be used for the (patho)physiological effects of endogenous substrates of neurolysin, among which the most characterized ones are neurotensin, bradykinin, angiotensin I, substance P, hemopressin, dynorphin A(1-8), metorphamide, and somatostatin (47, 53-55). Neurolysin hydrolyzes and inactivates all of these peptides except angiotensin I, dynorphin A(1-8), and metorphamide. Angiotensin I, the main inactive precursor peptide of the renin-angiotensin system, is converted into a bioactive peptide angiotensin-(1-7) by neurolysin. Dynorphin A(1-8), a kappa-opioid receptor agonist, and metorphamide, a kappa- and mu-opioid receptor agonist, are converted into delta-opioid receptor agonists Leu- and Met-enkephalins, respectively, by neurolysin. All of these bioactive peptides are critically involved in various brain functions (56-61). Their role in pathogenic mechanisms responsible for ischemic brain injury and several other neurological disorders has also been documented in multiple studies (62-67). If in a given pathophysiological condition several or most of the peptides inactivated by neurolysin have deleterious actions, then its activation could be beneficial to reduce levels of these peptides and halt or reverse progression of the disease. Likewise, if the bioactive peptides generated in the result of neurolysin's activity are protective, increased activity of the peptidase could again be beneficial. From a pharmaceutical standpoint, using one small molecule potentiator of neurolysin would be much more manageable and desirable for modulation of the function of these peptide systems, rather than using multiple small molecule receptor antagonists or agonists to target each peptide system separately.

It is important to note that the modulators identified in this study are histidine-containing dipeptides, L-histidyl-L-tyrosine (NlnA #1) and D,L-histidyl-D,L-histidine (NlnA #2). Interestingly, the first specific inhibitors of neurolysin were proline-containing dipeptides (68), of which L-prolyl-L-isoleucine is the most potent inhibitor in use as a research tool. Based on the data presented in this study, it is reasonable to predict (but not a limitation of the present invention) that N-terminal histidine, or part of its molecule, is the main pharmacophore in both modulators. However, the role of the C-terminal amino acid in binding of the molecule to the allosteric site of neurolysin and modulation of its activity cannot be excluded. It is important to note that NlnA #2 used in this study was a mixture of enantiomers (D- and L-histidine).

The most important findings of this study are that: (a) activity of neurolysin can be enhanced by small molecules; (b) allosteric binding site appears to be the same/very similar in neurolysins of rodent and human origin; and (c) identified enhancers are specific to neurolysin and largely inert to other homologous peptidases. Based on these key findings rational medicinal-chemical approaches could be applied to design molecules that possess high potency and other pharmacological properties (e.g., systemic and brain bioavailability) desirable for new research tools and drug leads.

In summary, this invention is the first to demonstrate that activity of neurolysin can be enhanced and describes identification of two small molecules that possess such properties. The molecules identified in this study could be developed into research tools for evaluation of the functional significance of neurolysin in pathogenesis of stroke and other neurological disorders, and may serve as starting structures for development of new class of drugs. Notably, the approach utilized in this study to identify allosteric modulators of neurolysin is largely unrecognized, despite being more efficient and economical then random screening approaches in yielding hit rates (27,46).

Figure 13:
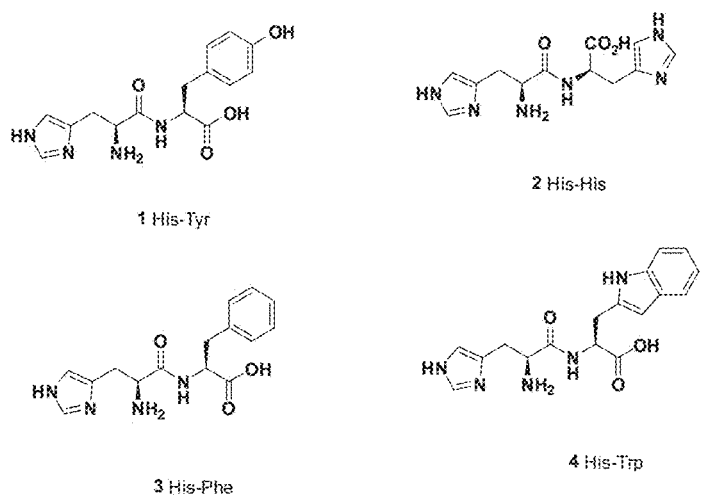
FIG. 13 shows the basic structures of dipeptide Nln activator hits.

Example 2. Peptidomimetic Neurolysin Activators Possessing Enhanced Brain Penetration and Stability To harness this discovery and evaluate the potential of Nln as a therapeutic target for stroke and other acute neurodegenerative disorders a structure-based discovery approach was used for rational identification of small molecules which can enhance catalytic efficiency of Nln (Jayaraman et al. 2021). While a small number of Nln inhibitors are known, no reported activators of Nln have been disclosed to date. The top hits from this screen were purchased and re-screened in the isolated enzyme assay disclosed herein to confirm activity. Four dipeptide compounds (FIG. 13) possessed activity to activate Nln based on half maximal activation concentration ($A_{50}$) and maximum activation percentage ($A_{max}$). The His-Tyr dipeptide (1) possessed an $A_{50}$=37.7 µM and $A_{max}$=467%, the His-His compound (2) $A_{50}$=46 µM and $A_{max}$=203%, His-Phe (3) $A_{50}$=130 µM and $A_{max}$=573% and His-Trp (4) $A_{50}$=34 µM and $A_{max}$=440%. Dipeptides 1, 2 and 4 were equipotent within 95% confidence intervals while His-Phe (3) was significantly less potent. As shown hereinabove, thorough pharmacological and biochemical/physical experiments have established the ability of these dipeptides to increase activity of recombinant rat and human, and mouse-brain isolated Nln, but do not affect activity of other peptidases closely related to Nln. These data identify valid hit compounds for further optimization as Nln activators to overcome their initial high micromolar potency and low stability.

The initial structure-activity relationship (SAR) of the dipeptide hits and detail a peptidomimetic approach was used to develop first-in-class potent, stable, selective, brain penetrant and 'drug-like' small molecule activators of Nln. These SAR studies result in identification of peptidomimetic compounds with 10-fold increase in potency, greater than 65-fold increase in mouse brain stability, significant selectivity over four highly homologous peptidases, 5-fold increased brain penetration and 'drug-like' fraction unbound in the brain. These compounds represent advanced hit compounds for further study as neuroprotectants[15-17] for stroke and wider neurodegenerative diseases, including, given the reported effects of Nln to degrade Abeta,[18] Alzheimer's Disease.

Chemistry. Initial optimization of the hit dipeptides involved iterative excision of amino acid functionality to identify the minimum pharmacophore of active peptidomimetics with enhanced blood-brain barrier (BBB) penetration. A number of precautions to avoid the potential for racemization in the amide bond coupling step were employed.[19] Racemization is reported to be more apparent with the use of N-acyl protecting groups at the α-amine compared with N-carbamate protection.[20, 21] Furthermore, the combination of the BOP coupling agent,[22] and Boc protection has been reported to suppress racemization in a number of syntheses.[20, 23] To this end, commercially available Boc-protected L- or D-histidine was coupled with an appropriately substituted primary amine in the presence of BOP coupling reagent and a base, to afford the respective amide intermediates (Scheme 1). Subsequent deprotection employing TFA yielded the targeted compounds in moderate to good yield. Specific rotation data obtained for selected derivatives confirmed retention of stereochemistry throughout this synthetic route when TFA concentration is limited to 20% and a 3 hour reaction time is observed.

Synthesis of Peptidomimetics[a]

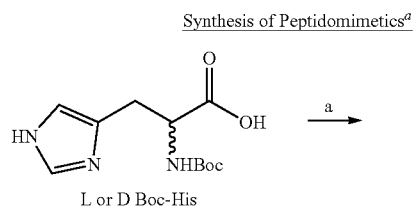

L or D Boc-His

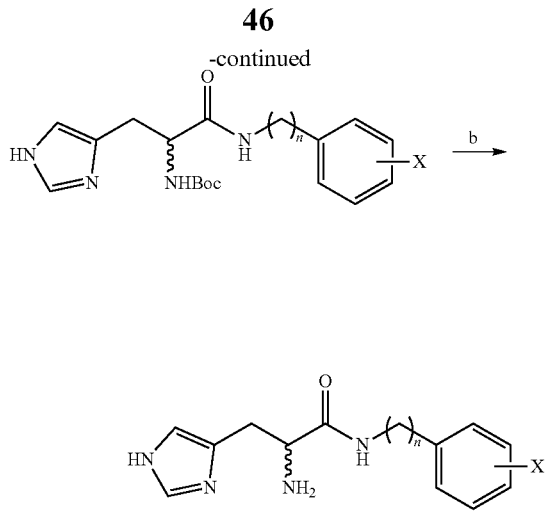

[a]Reagents and conditions: a) Appropriate amine, BOP, DIPEA, DMF, 50° C; b) 20% TFA, DCM, r.t.

Structure-Activity Relationship. These studies further validated the four hit dipeptides identified by the HTS. When these compounds were obtained from commercial sources and their structure independently confirmed by NMR, the His-Phe compound 3 was less active than the His-His (2) His-Tyr (1) and His-Trp (4) compounds, which all possessed equipotent high micromolar activity (Table 5). Thus compounds 1, 2 and 3 represented viable hit compounds for structure-activity relationship (SAR) studies. Characterization of each compound was performed by assignment of A50 and $A_{max}$, with 100% representing normal enzyme turnover in the latter. While these two parameters of biological activity are complementary, the inventors focused SAR design and compound development based on A50 values as these represent unambiguous evaluation criteria for drug discovery. While a 700% $A_{max}$ is excellent activity alone, when combined with an $A_{50}$=227 µM (see compound 5c).

TABLE 5

Structure, activation activity and in silico physicochemical property predictions of monocyclic aromatic-containing histidine peptidomimetics.

| Compound | Structure | $A_{50}$[1] (µM; 95% CI) | $A_{max}$[2] (%; 95% CI) | MPO[3] Score | LLE[4] |
|---|---|---|---|---|---|
| 1 | 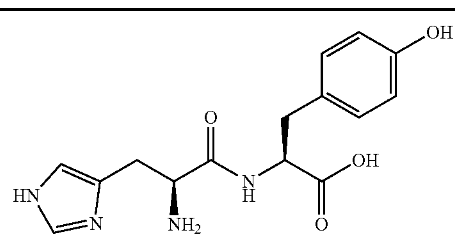 | 37.7 (24.5 to 58.6) | 467 (424.9 to 516.9) | 4 | 7.74 |
| 2 | 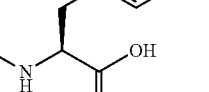 | 45.8 (32.0 to 65.6) | 202.8 (192.2 to 213.4) | 4 | 9.4 |

TABLE 5-continued

Structure, activation activity and in silico physicochemical property predictions of monocyclic aromatic-containing histidine peptidomimetics.

| Compound | Structure | $A_{50}{}^1$ (μM; 95% CI) | $A_{max}{}^2$ (%; 95% CI) | MPO[3] Score | LLE[4] |
|---|---|---|---|---|---|
| 3 | 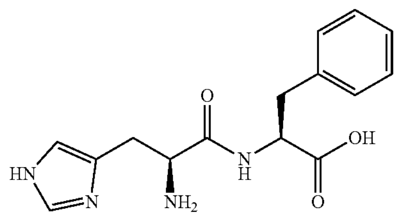 [SMILES: N[C@@H](Cc1c[nH]cn1)C(=O)N[C@@H](Cc1ccccc1)C(=O)O] | 130.2 (113.5 to 150.1) | 573 (547.9 to 602.7) | 3.8 | 6.53 |
| 4 | 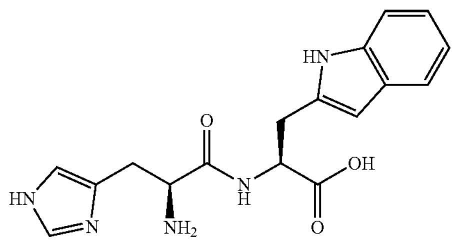 [SMILES: N[C@@H](Cc1c[nH]cn1)C(=O)N[C@@H](Cc1cc2ccccc2[nH]1)C(=O)O] | 34 (24 to 48.12) | 440.3 (414.3 to 467.9) | 4.1 | 7.13 |
| 4a | 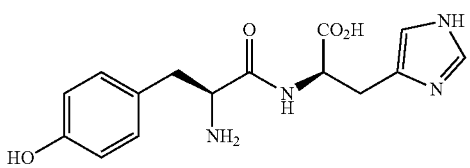 [SMILES: N[C@@H](Cc1ccc(O)cc1)C(=O)N[C@H](Cc1c[nH]cn1)C(=O)O] | Inactive | Inactive | N/A | N/A[5] |
| 4b | 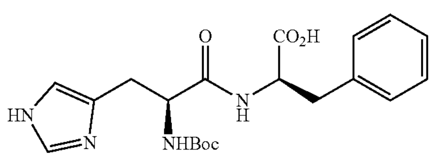 [SMILES: CC(C)(C)OC(=O)N[C@@H](Cc1c[nH]cn1)C(=O)N[C@H](Cc1ccccc1)C(=O)O] | Inactive | Inactive | N/A | N/A |
| 4c | 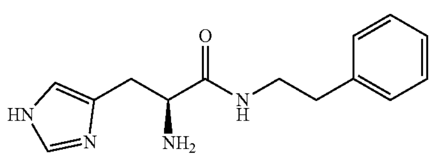 [SMILES: N[C@@H](Cc1c[nH]cn1)C(=O)NCCc1ccccc1] | 20.7 (10.5-40.8) | 337.2 (302-378.6) | 5 | 4.86 |
| 4d | 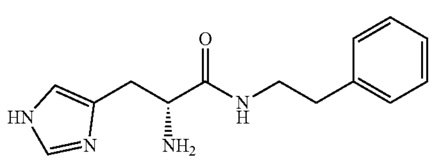 [SMILES: N[C@H](Cc1c[nH]cn1)C(=O)NCCc1ccccc1] | 24.6 (17.3 to 35) | 294.6 (278.0 to 313) | 5 | 4.79 |
| 4e | 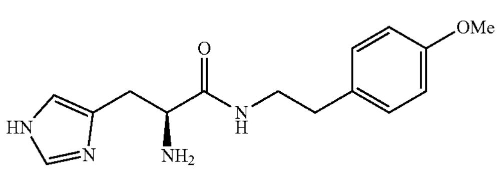 [SMILES: COc1ccc(CCNC(=O)[C@@H](N)Cc2c[nH]cn2)cc1] | 46 (31.5 to 68) | 339.4 (314.2 to 369.3) | 5 | 4.60 |
| 4f | 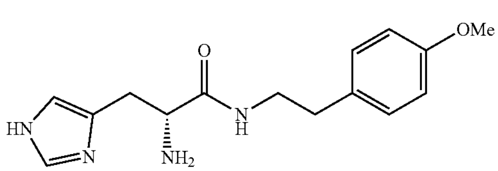 [SMILES: COc1ccc(CCNC(=O)[C@H](N)Cc2c[nH]cn2)cc1] | 66.4 (48.1 to 92.7) | 378.3 (350.5 to 411.9) | 5 | 4.44 |

TABLE 5-continued

Structure, activation activity and in silico physicochemical property predictions of monocyclic aromatic-containing histidine peptidomimetics.

| Compound | Structure | $A_{50}{}^1$ (μM; 95% CI) | $A_{max}{}^2$ (%; 95% CI) | MPO[3] Score | LLE[4] |
|---|---|---|---|---|---|
| 4g | [structure: L-histidine amide with 2-methoxyphenethylamine] | 31.8 (21 to 48.7) | 319 (296.1 to 345.4) | 5 | 4.76 |
| 4h | [structure: D-histidine amide with 2-methoxyphenethylamine] | 30 (24 to 37.5) | 328 (315.4 to 342) | 5 | 4.78 |
| 4i | [structure: L-histidine amide with 3-methoxyphenethylamine] | 29.6 (22.7 to 38.8) | 367 (349.7 to 387.1) | 5 | 4.79 |
| 4j | [structure: D-histidine amide with 3-methoxyphenethylamine] | 19.8 (9.5 to 40.6) | 255.3 (230.5 to 284.8) | 5 | 4.97 |
| 4k | [structure: L-histidine amide with 4-trifluoromethylphenethylamine] | 15.7 (11.6 to 22.4) | 299.4 (283.9 to 316.2) | 5 | 4.10 |
| 4l | [structure: D-histidine amide with 4-trifluoromethylphenethylamine] | 24 (17.9 to 32.2) | 330.1 (313.9 to 347.7) | 5 | 3.92 |
| 4m | [structure: L-histidine amide with 4-fluorophenethylamine] | 27.89 (22.4 to 34.8) | 323.1 (311.4 to 335.6) | 5 | 4.59 |
| 4n | [structure: D-histidine amide with 4-fluorophenethylamine] | 35.7 (29.3 to 43.6) | 353.8 (340.6 to 368.1) | 5 | 4.49 |
| 4o | [structure: L-histidine amide with 4-nitrophenethylamine] | 9.8 (6.3 to 15.15) | 282.4 (266.5 to 299.5) | 4 | 5.45 |

TABLE 5-continued

Structure, activation activity and in silico physicochemical property predictions of monocyclic aromatic-containing histidine peptidomimetics.

| Compound | Structure | $A_{50}$[1] (μM; 95% CI) | $A_{max}$[2] (%; 95% CI) | MPO[3] Score | LLE[4] |
|---|---|---|---|---|---|
| 4p | 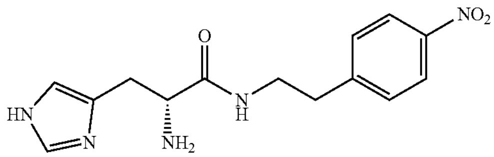 [SMILES: N[C@H](Cc1c[nH]cn1)C(=O)NCCc1ccc([N+](=O)[O-])cc1] | 25.5 (16.7 to 38.8) | 267.5 (250.1 to 287.1) | 4 | 5.03 |
| 4q | 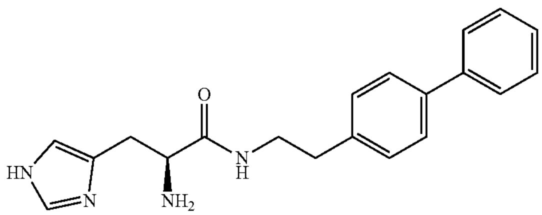 [SMILES: N[C@@H](Cc1c[nH]cn1)C(=O)NCCc1ccc(-c2ccccc2)cc1] | 9.5 (6.12 to 14.6) | 258.2 (244 to 273.4) | 5 | 3.32 |
| 4r | 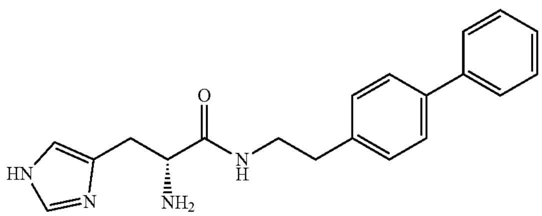 [SMILES: N[C@H](Cc1c[nH]cn1)C(=O)NCCc1ccc(-c2ccccc2)cc1] | 11.7 (8.26 to 16.7) | 269.7 (256.8 to 283.4) | 5 | 3.22 |
| 5a | 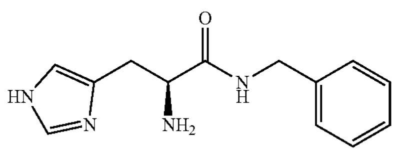 [SMILES: N[C@@H](Cc1c[nH]cn1)C(=O)NCc1ccccc1] | 24.25 (7.85 to 71.4) | 152.2 (137.3 to 171.5) | 5 | 5.01 |
| 5b | 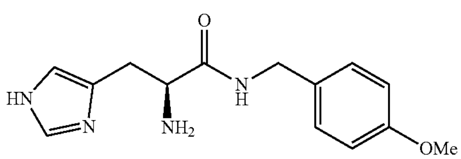 [SMILES: COc1ccc(CNC(=O)[C@@H](N)Cc2c[nH]cn2)cc1] | 221 (149 to 354) | 428.8 (373 to 523.5) | 5 | 4.13 |
| 5c | 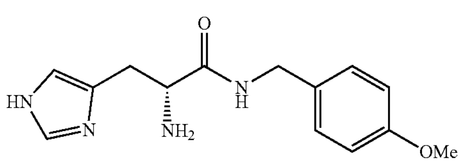 [SMILES: COc1ccc(CNC(=O)[C@H](N)Cc2c[nH]cn2)cc1] | 226.8 (146 to 392.4) | 703.5 (588.9 to 915.6) | 5 | 4.12 |
| 5d | 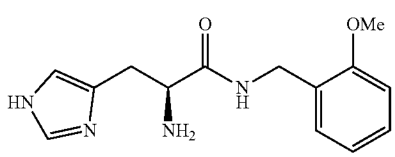 [SMILES: COc1ccccc1CNC(=O)[C@@H](N)Cc1c[nH]cn1] | 42.31 (32.1 to 55.6) | 385.8 (363.8 to 410.5) | 5 | 4.85 |
| 5e | 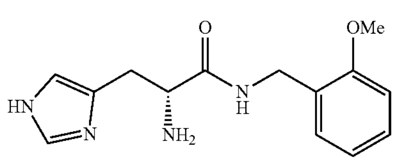 [SMILES: COc1ccccc1CNC(=O)[C@H](N)Cc1c[nH]cn1] | 43.4 (30.9 to 61.5) | 324.9 (304 to 349) | 5 | 4.84 |

TABLE 5-continued

Structure, activation activity and in silico physicochemical property predictions of monocyclic aromatic-containing histidine peptidomimetics.

| Compound | Structure | $A_{50}$[1] (µM; 95% CI) | $A_{max}$[2] (%; 95% CI) | MPO[3] Score | LLE[4] |
|---|---|---|---|---|---|
| 5f | 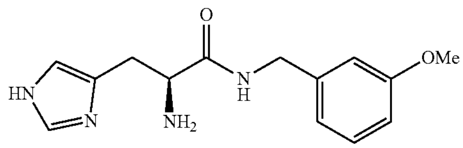 [SMILES: COc1cccc(CNC(=O)[C@@H](N)Cc2c[nH]cn2)c1] | 66.8 (51.6 to 87.1) | 327.5 (309.7 to 348.2) | 5 | 4.65 |
| 5g | 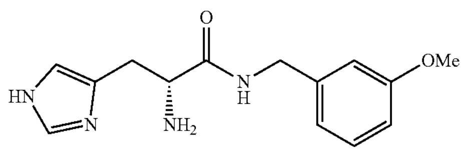 [SMILES: COc1cccc(CNC(=O)[C@H](N)Cc2c[nH]cn2)c1] | 61.83 (46.5 to 83) | 477.1 (444 to 516) | 5 | 4.68 |
| 5h | 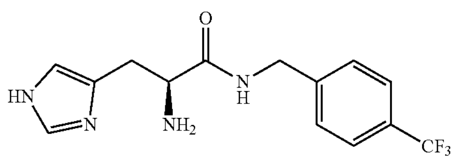 [SMILES: N[C@@H](Cc1c[nH]cn1)C(=O)NCc1ccc(C(F)(F)F)cc1] | 25.8 (19.5 to 34.19) | 287.7 (274.7 to 301.8) | 5 | 4.10 |
| 5i | 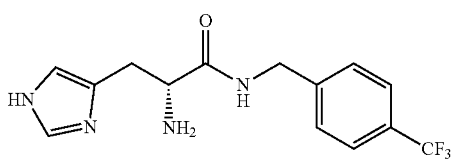 [SMILES: N[C@H](Cc1c[nH]cn1)C(=O)NCc1ccc(C(F)(F)F)cc1] | 29.3 (917.1 to 48.9) | 319.1 (296.3 to 344.3) | 5 | 4.04 |
| 5j | 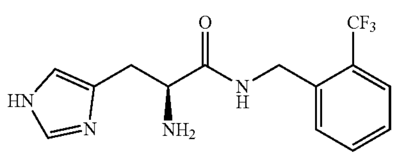 [SMILES: N[C@@H](Cc1c[nH]cn1)C(=O)NCc1ccccc1C(F)(F)F] | 48.6 (31.4 to 76.7) | 362.2 (331.6 to 400.1) | 5 | 3.91 |
| 5k | 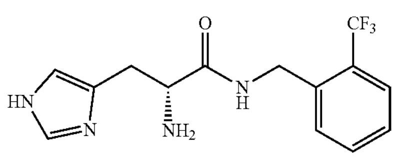 [SMILES: N[C@H](Cc1c[nH]cn1)C(=O)NCc1ccccc1C(F)(F)F] | 27.1 (17.1 to 43.3) | 345.8 (317.5 to 378.3) | 5 | 4.08 |
| 5l | 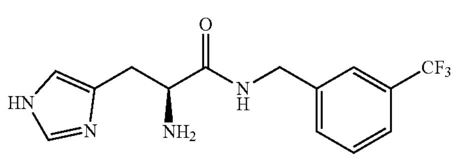 [SMILES: N[C@@H](Cc1c[nH]cn1)C(=O)NCc1cccc(C(F)(F)F)c1] | 8.6 (4.9 to 14.9) | 270.2 (251.4 to 290.7) | 5 | 4.58 |
| 5m | 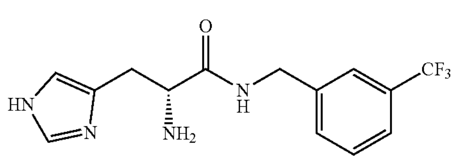 [SMILES: N[C@H](Cc1c[nH]cn1)C(=O)NCc1cccc(C(F)(F)F)c1] | 19.95 (11.1 to 35.4) | 282 (258.4 to 309.1) | 5 | 4.21 |
| 5n | 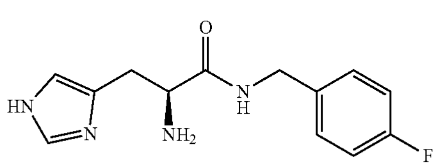 [SMILES: N[C@@H](Cc1c[nH]cn1)C(=O)NCc1ccc(F)cc1] | 14.9 (10-22) | 293 (276.5-310.7) | 5 | 5.08 |

TABLE 5-continued

Structure, activation activity and in silico physicochemical property predictions of monocyclic aromatic-containing histidine peptidomimetics.

| Compound | Structure | $A_{50}{}^{1}$ (μM; 95% CI) | $A_{max}{}^{2}$ (%; 95% CI) | MPO[3] Score | LLE[4] |
|---|---|---|---|---|---|
| 5o | 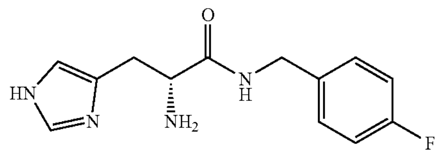 [SMILES: N[C@H](Cc1c[nH]cn1)C(=O)NCc1ccc(F)cc1] | 29.8 (20.8 to 42.9) | 320.5 (299.7 to 343.9) | 5 | 4.78 |
| 5p | 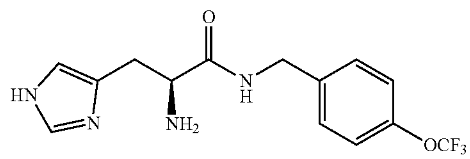 | 27.4 (17.6 to 42.81) | 310 (287.2 to 336.1) | 5 | 4.07 |
| 5q | 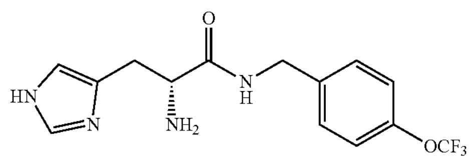 | 26.7 (14.9 to 46.4) | 337.1 (312 to 364.9) | 5 | 4.09 |
| 5r | 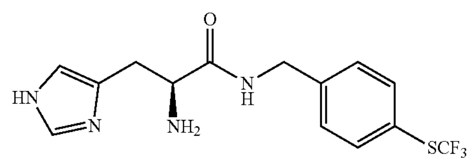 [SMILES: N[C@@H](Cc1c[nH]cn1)C(=O)NCc1ccc(OC(F)(F)F)cc1] | 28.16 (22.67 to 35.03) | 287.5 (277.4 to 298.4) | 5 | 3.28 |
| 5s | 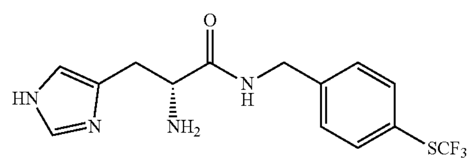 [SMILES: N[C@H](Cc1c[nH]cn1)C(=O)NCc1ccc(OC(F)(F)F)cc1] | 16.1 (9.5 to 27.1) | 251.5 (233.7 to 271.3) | 5 | 3.52 |
| 6a | 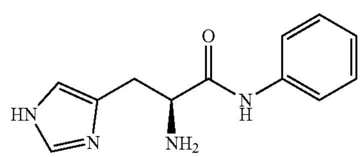 [SMILES: N[C@@H](Cc1c[nH]cn1)C(=O)Nc1ccccc1] | 252 (170.6 to 406.6) | 466.6 | 5 | 4.02 |
| 6b | 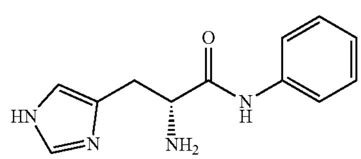 [SMILES: N[C@H](Cc1c[nH]cn1)C(=O)Nc1ccccc1] | 113.6 (92.8 to 140.5) | 440.3 (414.9 to 470.4) | 5 | 4.37 |
| 7a | 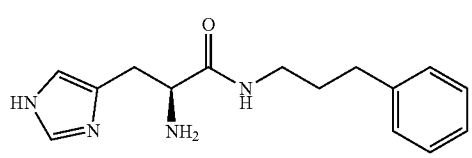 [SMILES: N[C@@H](Cc1c[nH]cn1)C(=O)NCCCc1ccccc1] | 20.6 (14.91 to 28.4) | 288.1 (273.6 to 303.8) | 5 | 4.49 |
| 7b | 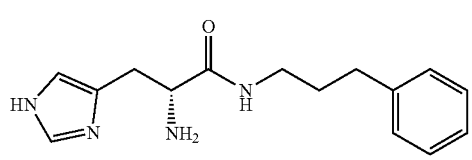 [SMILES: N[C@H](Cc1c[nH]cn1)C(=O)NCCCc1ccccc1] | 21 (16-27.7) | 281.8 (269.9-294.5) | 5 | 4.48 |

TABLE 5-continued

Structure, activation activity and in silico physicochemical property predictions of monocyclic aromatic-containing histidine peptidomimetics.

| Compound | Structure | $A_{50}^1$ (µM; 95% CI) | $A_{max}^2$ (%; 95% CI) | MPO[3] Score | LLE[4] |
|---|---|---|---|---|---|
| 8a | 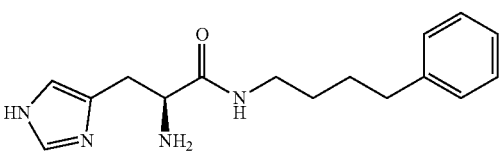 [SMILES: N[C@@H](Cc1c[nH]cn1)C(=O)NCCCCc1ccccc1] | 126 (101-159) | 328 (309-351) | 5 | 3.17 |
| 8b | 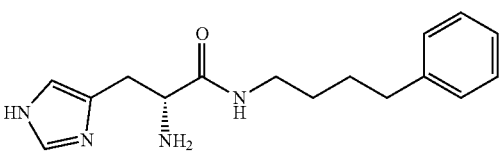 [SMILES: N[C@H](Cc1c[nH]cn1)C(=O)NCCCCc1ccccc1] | 27.4 (16.9 to 46.8) | 233.8 (215.9 to 254.8) | 5 | 3.84 |

[1] Concentration required to activate Nln by 50%.
[2] Maximum % activation achieved.
[3] Multi-Parameter Optimization.
[4] Ligand-lipophilicity efficiency.
[5] Not applicable.

In an effort to further develop potent and selective neurolysin (Nln) activators that do not suffer from the characteristic metabolic lability of dipeptides,[24-26] the inventors used a peptidomimetic approach. Given the apparently conserved histidine moiety present as the Western fragment in all four hit compounds, this moiety was retained and modifications focused on the Eastern aromatic amino acid moieties to attenuate peptide character. While the tyrosine (1) and tryptophan (4)-containing hits possess similar activity with $A_{50}$=37.7 µM and 34 µM respectively, the phenylalanine compound (3) possessed an $A_{50}$=130.2 µM, over threefold less active than 1, suggesting a pharmacophoric role for the phenol ring of the tyrosine amino acid and the indole ring of the tryptophan. Targeting the neuropeptidase Nln necessitates penetration of designed activators into the brain. Thus, the inventors approximated blood-brain barrier (BBB) penetration of analogues with the multi-parameter optimization (MPO)[27] score augmented with ligand-lipophilicity efficiency (LLE).[15, 28] Analysis of the MPO scores of hit compounds 1, 3 and 4 (4, 3.8 and 4.1 respectively) predict poor, or low, BBB penetrance as expected from dipeptides.[29] Thus, the SAR strategy focused on removing the amino acid functionality that classically impedes BBB penetration, increasing lipophilicity, varying terminal aromatic ring substitution and establishment of the importance of the stereocenter of the histidine amine group to determine the eutomer. Derivatives were broadly separated into two categories; substituted monocyclic aromatics (Table 5; compounds 4a-r, 5a-s, 6a, 7a-b, 8a-b) and bulkier bicyclic aromatic/heteroaromatics (Table 6; compounds 9a-9f, 10a-f). Most derivatives possessed an MPO score of ≥4 (Table 5-6) validating this synthetic approach. It is worth noting that an MPO value of 5 is obtained for many derivatives due to the modifications being introduced not largely varying the underlying physicochemical properties of the compounds. LLE was used as a predictor of 'drug-likeness' (Table 5, 6).[30] A molecule is often considered 'drug-like' if its LLE score exceeds five in combination with a lipophilic c log P value.[31, 32]

TABLE 6

Structure, activation activity and in silico physicochemical property predictions of bicyclic aromatic-containing histidine peptidomimetics.

| Compound | Structure | $A_{50}^1$ (µM; 95% CI) | $A_{max}^2$ (%; 95% CI) | MPO[3] | LLE[4] |
|---|---|---|---|---|---|
| 4 | 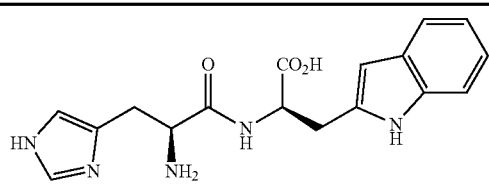 | 34 (24 to 48.12) | 440.3 (414.3 to 467.9) | 4 | 7.13 |
| 9a | 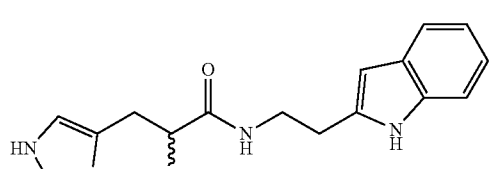 | 4.3 (3.4 to 5.4) | 311 (298.6 to 325.7) | 4.9 | 5.56 |

TABLE 6-continued

Structure, activation activity and in silico physicochemical property predictions of bicyclic aromatic-containing histidine peptidomimetics.

| Compound | Structure | $A_{50}{}^1$ (μM; 95% CI) | $A_{max}{}^2$ (%; 95% CI) | MPO[3] | LLE[4] |
| --- | --- | --- | --- | --- | --- |
| 9b | 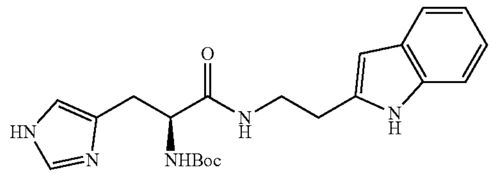 [SMILES: CC(C)(C)OC(=O)N[C@@H](Cc1c[nH]cn1)C(=O)NCCc1cc2ccccc2[nH]1] | Inactive | Inactive | N/A | N/A |
| 9c | 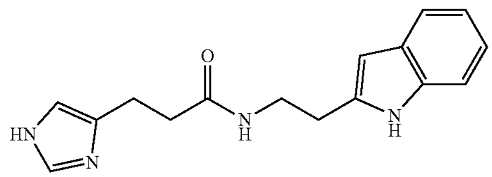 [SMILES: O=C(CCc1c[nH]cn1)NCCc1cc2ccccc2[nH]1] | Inactive | Inactive | N/A | N/A |
| 9d | 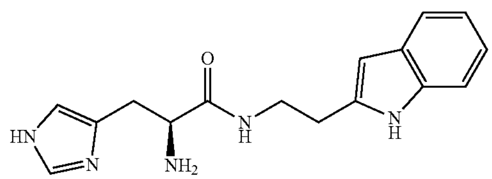 [SMILES: N[C@@H](Cc1c[nH]cn1)C(=O)NCCc1cc2ccccc2[nH]1] | 6.1 (3.7 to 10.12) | 259 (240.7 to 281) | 4.9 | 5.41 |
| 9e | 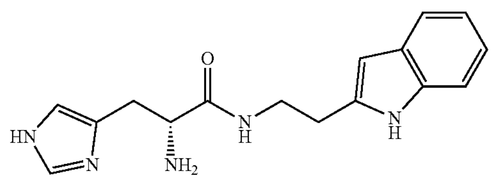 [SMILES: N[C@H](Cc1c[nH]cn1)C(=O)NCCc1cc2ccccc2[nH]1] | 1.0 (0.16 to 4.4) | 132 (122.5 to 143.6) | 4.9 | 6.19 |
| 9f | 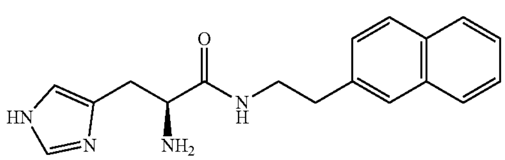 [SMILES: N[C@@H](Cc1c[nH]cn1)C(=O)NCCc1ccc2ccccc2c1] | 13.6 (10.1 to 18.2) | 323.7 (310.3 to 337.9) | 5 | 3.87 |
| 9g | 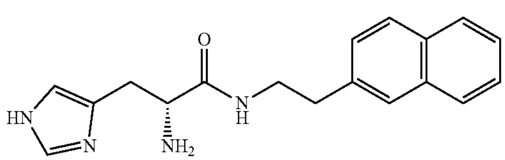 [SMILES: N[C@H](Cc1c[nH]cn1)C(=O)NCCc1ccc2ccccc2c1] | 25.2 (19.6 to 32.4) | 339.8 (325.4 to 355.4) | 5 | 3.61 |
| 10a | 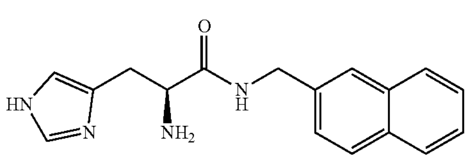 [SMILES: N[C@@H](Cc1c[nH]cn1)C(=O)NCc1ccc2ccccc2c1] | 4.4 (1.7 to 11) | 210.9 (191.7 to 231.9) | 5 | 4.58 |
| 10b | 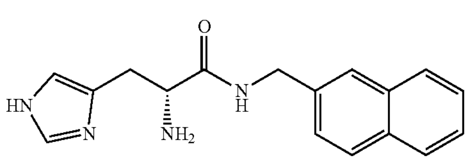 [SMILES: N[C@H](Cc1c[nH]cn1)C(=O)NCc1ccc2ccccc2c1] | 6.3 (3.8 to 10.7) | 197.5 (184.9 to 214.8) | 5 | 4.42 |

TABLE 6-continued

Structure, activation activity and in silico physicochemical property predictions of bicyclic aromatic-containing histidine peptidomimetics.

| Compound | Structure | $A_{50}^1$ (μM; 95% CI) | $A_{max}^2$ (%; 95% CI) | MPO[3] | LLE[4] |
|---|---|---|---|---|---|
| 10c | (L-histidine-naphthylmethylamide structure) | 4.2 (3.17 to 5.6) | 264 (256.3 to 272.6) | 5 | 4.60 |
| 10d | (D-histidine-naphthylmethylamide structure) | 15.37 (10.9 to 21.5) | 343 (325.2 to 363.5) | 5 | 4.04 |
| 11a | (L-histidine-8-aminoquinoline structure) | 4.4 (2.07 to 9.14) | 252.4 (231.4 to 274.9) | 4.9 | 5.27 |
| 11b | (D-histidine-8-aminoquinoline structure) | 3.7 (1.7 to 7.9) | 255.2 (239.9 to 278.9) | 4.9 | 5.35 |

[1]Concentration required to activate Nln by 50%.
[2]Maximum % activation achieved.
[3]Multi-Parameter Optimization.
[4]Ligand-lipophilicity efficiency.
[5]Not applicable.

To gain a better understanding of the pharmacophoric requirements for Nln binding, compound 4a (H-Try-His-OH), the reverse analog of 1, was purchased and its structure confirmed by NMR. This reversal led to the complete amelioration of Nln activation, suggesting that histidine linked via its C-terminus is crucial for the activation of Nln. The pharmacophoric role of the primary amine of the histidine moiety was further confirmed when the derivative containing a boc protected carbamate at this position (4b) (Table 5) was found to be inactive. Excision of this amine, illustrated by trypotophan derivative (9c, Table 6), also results in complete amelioration of activity. Thus, a primary amine or at least a hydrogen bond acceptor (given the elimination of hydrogen bond acceptance ability due to the carbamate resonance structure placing a positive charge on the nitrogen) is required at this position of the compound for Nln activation. These observations support a critical pharmacophoric role for the terminal histidine moiety.

Excision of the carboxylic acid moiety from the His-Phe hit (3) to afford derivative 4c significantly improved $A_{50}$ from 130.2 to 20.7 μM while slightly reducing $A_{max}$ from 573% to 337%. Moreover, MPO score increased to 5, indicating BBB penetration, with an LLE value of 4.86. This observation indicated it was possible to obtain more active compounds from this hit series (based on $A_{50}$) and that further SAR studies were warranted. Indeed, the absence of the para OH group on 4c indicated that a tyrosine moiety is not a requirement for activity. Given the apparent pharmacophoric nature of the free amine of the histidine, the impact of stereochemistry at this position of the molecule was examined. The unnatural dipeptide 4d containing D-histidine, opposite to the L-histidine present in 4c, was synthesized and found to be equipotent within 95% confidence limits with $A_{50}$ of 24.5 μM and 20.7 μM, and $A_{max}$ of 295% and 337% respectively. This trend was repeated with most of the monocyclic derivatives with no eutomer identifiable for $A_{50}$ activity. However, the p-nitro compounds L-4o and D-4p showed approximately two-fold difference in $A_{50}$ values (9.8 and 25.5 μM respectively) but with equipotent $A_{max}$. The MPO score of both of these compounds (4) is much lower than compared to other derivatives. Compound D-5o possessed approximately two-fold greater activity than L-5n with $A_{50}$ values of 30 μM and 15 μM respectively but with similar $A_{max}$ values. Within the aniline derivatives, L-6a possessed much lower activity compared with D-6b ($A_{50}$=252 and 114 μM respectively) but comparable $A_{max}$ (467% and 440% respectively). The trend of no correlation between activity and stereochemistry held in the bicyclic derivatives with the exception of the napthyl compounds L-10c and D-10d possessing $A_{50}$ values of 4.2 and 15 μM, and $A_{max}$ values of 264% and 343% respectively.

Next, the inventors conducted a substituent scan around the terminal phenyl ring employing an electron-donating methoxy group. The para position (4e and 4f) showed the least amount of activity with $A_{50}$ values of 46 and 66 µM respectively. When the methoxy was moved to the ortho position (4g and 4h) activity increased to afford equipotent compounds with a mean $A_{50}$ of 31 µM. Similar activity was seen when substitution was moved to the meta position (L-4i and D-4j) with $A_{50}$ values of 30 and 20 µM respectively. When the substituent was switched to a para $CF_3$ electron-withdrawing group (4k and 4l), activity was substantially increased with 4k possessing an $A_{50}$=16 µM and $A_{max}$ of 299%, with the opposite enantiomer 4l being equipotent within confidence limits. A less electron-withdrawing fluorine substituent at the para position of the terminal phenyl ring (4m and 4n) affords similar activity with 4m possessing an $A_{50}$=28 µM and $A_{max}$ of 323%. Introduction of a para nitro group (4o and 4p) increased activity with L-4o possessing an $A_{50}$=10 µM and $A_{max}$ of 282%, approximately double the activity of its enantiomer. Notably both 4o and 4p possessed LLE values greater than 5 but with lower MPO scores of 4. Finally, for this series, a second phenyl ring was added to the para position of the terminal phenyl to afford compounds 4q and 4r which possessed some of the most potent $A_{50}$ values identified to date; 9.5 and 11.7 µM respectively, with equipotent $A_{max}$ values of 258% and 269%. However, the lipophilicity of the biphenyl moiety reduces the LLE of these compounds to 3.3.

Cognizant of the potential metabolic lability of the amide bond within this scaffold, the inventors next investigated a truncated homologation series in which the ethyl linker to the terminal aromatic ring was reduced a single methylene, thus increasing steric hinderance around the amide bond. Surprisingly, benzyl derivative 5a ($A_{50}$=24 µM, $A_{max}$=152%) possessed similar activity to its phenethyl counterpart 4c ($A_{50}$=20.7 µM, $A_{max}$=337%). Performing a substituent scan again with a methoxy group, activity increased in the order of ortho>meta>>para. Compound 5e (o-OMe) possesses an $A_{50}$=43.4 µM and $A_{max}$=325%, compound 5g (m-OMe) an $A_{50}$=62 µM and $A_{max}$=477%, and compound 5c (p-OMe) an $A_{50}$=227 µM and $A_{max}$=704%. This pattern highlights a significant and surprising difference from the phenethyl series wherein all positions were largely equipotent. The electron-withdrawing $CF_3$ group afforded greater activity in the phenylethyl series, as such, a substituent scan was conducted with this group in the benzyl series (compounds 5h-5m). Here, activity increased in the order of meta>para>ortho. Compound 5l (m-$CF_3$) possesses an $A_{50}$=8.6 µM and $A_{max}$=312%, compound L-5h (p-$CF_3$) an $A_{50}$=26 µM and $A_{max}$=288%, and compound 5j (o-$CF_3$) an $A_{50}$=49 µM and $A_{max}$=362%. Fluorine substitution at the para position (L-5n) is equipotent, within confidence limits, with $CF_3$ substitution, as is the p-$OCF_3$ derivative L-5p. Introduction of a p-$SCF_3$ to afford L-5r retains similar activity to L-5h however, in this case, the opposite enantiomer (D-5s) shows slightly improved activity with $A_{50}$=16 µM and $A_{max}$=140%.

Further homologation to completely excise the linker afforded arylamide L-6a possessing an $A_{50}$=252 µM and $A_{max}$=467% with an MPO score predictive of BBB penetration (5) and a 'drug-like' LLE of 5.5 (Table 5). Thus, stereochemistry has a larger role to play in activity as D-6b possesses an $A_{50}$=114 µM and $A_{max}$=440%, more than 2-fold more potent than L-6a. Extension of the linker to a propyl chain (7a) had no effect on activity compared with phenethyl (4c) and benzyl (5a) linkers. Introduction of a butyl linker (8a) significantly reduced activity ($A_{50}$=126 µM, $A_{max}$=328%) with the L enantiomer but the opposite enantiomer (D-8b, $A_{50}$=27.4 µM) retained equipotent activity to 4c and 5a. Thus, a linker length of between 1-3 carbons is optimal for activity while 0 and 4 carbons reduce activity, suggesting the compounds occupy a binding pocket within Nln of limited space.

Bicyclic compounds further increase steric hinderance around the amide bond potentially affording greater stability. The hit tryptophan compound (3) possessed equipotent activity with the tyrosine hit (1) but with an enhanced $A_{max}$=440% and an LLE of 7.1. Derivative synthesis (Table 6) confirmed the observations from the monocyclic series; excision of the carboxylic acid moiety (9a) retains and boosts activity ($A_{50}$=4.3 µM), carbamate protection of the free amine (9b) ameliorates activity, as does excision of the free amine (9c), further supporting a pharmacophoric role for the histidine moiety in Nln activation. The carboxylic acid excised compound was initially obtained as a racemic mixture. Enantioselective synthesis resolved the two stereoisomers to afford L-9d ($A_{50}$=6.1 µM, $A_{max}$=259%) and D-9e ($A_{50}$=1.0 µM, $A_{max}$=132%), significantly more potent than the parent hit and possessing 'drug-like' LLE scores and predictive BBB penetration by MPO scores of 4.9.

Based on this data, the inventors next looked to excise the heteroatom in the bicyclic ring and synthesized the 2-ethylnaphthylene derivatives L-9f and D-9g, but this modification resulted in attenuation of activity with $A_{50}$ values of 13.6 and 25.2 µM respectively, suggesting a role in binding the target protein for the indole nitrogen. Following the observation that truncation of the linker chain results in retained activity, 2-methylnaphtalene derivatives L-10a and D-10b were synthesized which possessed $A_{50}$ values of 4.4 and 6.3 µM respectively. A positional switch to the 1-methylnaphtalene derivatives L-10c and D-10d did not appreciably alter activity ($A_{50}$=4.2 and 15.4 µM respectively). Excision of the linker and reintroduction of a nitrogen to afford 8-quinoline derivatives L-11a and D-11b afforded two of the most active derivatives to date ($A_{50}$=4.4 and 3.7 µM respectively). Furthermore, these compounds possess mean $A_{max}$ values of 254% combined with predicted BBB penetration by MPO score, 'drug-like' LLE values above 5 and likely enhanced stability of the amide bond given the steric congestion they afford.

Figure 14:
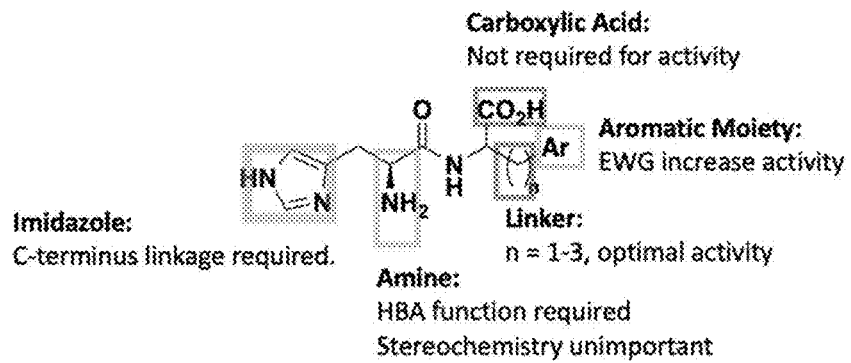
FIG. 14 shows an overview of established SAR for Nln activation.

In summary, a histidine amino acid forming an amide bond with its C-terminus, possessing a free amine, forms part of the pharmacophore of this scaffold. However, stereochemistry at the amine is unimportant. Excision of the carboxylic acid from the hit scaffolds retains activity while enhancing BBB penetration and truncation of the linker chain from the amide to the terminal aromatic moiety improves activity (FIG. 14). Numerous compounds, exemplified by 4o, 4q, 5l, 10c and 11a-b, were identified with low micromolar $A_{50}$ values to activity neurolysin, combined with high $A_{max}$ values, 'drug-like' LLE values and enhanced stability (see below).

In Vitro Metabolic Stability Studies. The hit His-Tyr (1) and His-Trp (4) scaffolds, along with improved derivatives 9d, 10c and 11a were selected to undergo in vitro plasma and brain homogenate stability determination (Table 7). In-vitro half-life ($t_{1/2}$) values, defined as the time needed for 50% degradation of the compound, were calculated by assuming pseudo-first-order degradation.

Dipeptide compound 1 possessed a half-life of 34 minutes in mouse plasma as expected for the labile amide bond. However, the more sterically hindered amide bond within the His-Trp hit compound 4 possessed a half-life of >300 minutes in mouse plasma, validating our SAR strategy to introduce increased steric hinderance around the amide bond through bicyclic aromatic moieties and truncating the linker chain. Surprisingly, the carboxylic acid excised derivative, 9d, and the 1-methylnaphtalene derivative, 10c, show significantly enhanced half-lives in mouse plasma of >1000 minutes. The quinoline derivative, 11a, showed a more moderate mouse plasma half-life of 248 minutes, superior to 1 and similar to 4, perhaps indicating a role for the quinoline nitrogen in intramolecular hydrogen bonding. Both dipeptide hits showed particular instability in mouse brain homogenate with half-lives below 1.6 minutes. Derivatives 9d, 10c and 11a possessed significantly improved stability in mouse brain homogenate by at least 41-fold and, in the case of 11a, up to 117-fold, with half-lives of 66, 80 and 182 minutes respectively.

Plasma And Brain Protein Binding. The rapid equilibrium dialysis (RED) device was used to investigate the extent of plasma and brain protein binding and calculate the fraction unbound of selected Nln activators (Table 8). His-Trp hit compound 4 has the highest unbound fraction in mouse plasma whereas hit compound 1 has more protein binding affinity (less $f_u$) compare with 4. Indole compound 9d showed similar fraction unbound to hit compound 1 in plasma however, derivatives 10c and 11a have lower unbound fractions in plasma.

Due to the metabolic instability of the hit compounds 1 and 4 in brain homogenate (Table 7), brain protein binding

TABLE 7

Half-live of selected Nln activators in mouse blood plasma and brain homogenate.
Data expressed as the mean of n = 3 experiments ±SD.

| Compound | Structure | $A_{50}$ (μM; 95% CI) | $t_{1/2}$ (min) Mouse Plasma | $t_{1/2}$ (min) Mouse Brain |
|---|---|---|---|---|
| 1 (His-Tyr) | 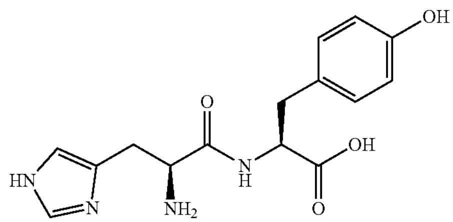 [SMILES: N[C@@H](Cc1c[nH]cn1)C(=O)N[C@@H](Cc1ccc(O)cc1)C(=O)O] | 37.7 (24.5 to 58.6) | 34.19 ± 1.97 | 1.03 ± 0.4 |
| 4 (His-Trp) | 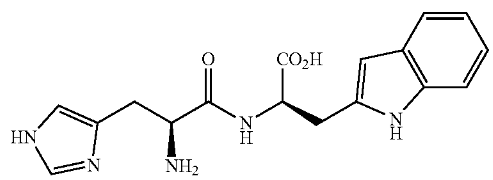 [SMILES: N[C@@H](Cc1c[nH]cn1)C(=O)N[C@H](Cc1cc2ccccc2[nH]1)C(=O)O] | 34 (24 to 48.12) | >300 | 1.55 ± 0.37 |
| 9d | 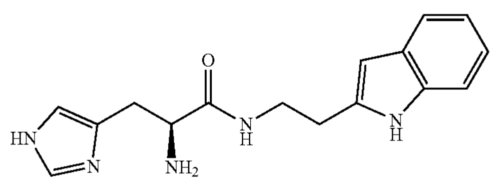 | 6.1 (3.7 to 10.12) | >1000 | 65.5 ± 4.2 |
| 10c | 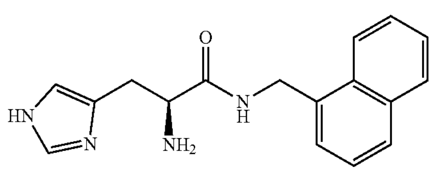 [SMILES: N[C@@H](Cc1c[nH]cn1)C(=O)NCc1cccc2ccccc12] | 4.2 (3.17 to 5.6) | >1000 | 80.3 ± 2 |
| 11a | | 4.4 (2.07 to 9.14) | 248.25 ± 28.1 | 181.55 ± 14.9 | assay was not performed for these compounds. Similar to plasma, derivative 9d showed higher fraction unbound in brain tissue compare with the other two derivatives which have almost the same values for $f_u$ in brain tissue.

co-culture model of the BBB at 37° C. The permeability coefficient (Pe) was calculated from the cleared volume of each compound versus time. Values represent the mean±SD of three measurements.

TABLE 8

Fraction unbound ($f_u$) in mouse plasma and brain homogenate of selected Nln activators. Data expressed as the mean of n = 3 experiments ±SD.

| Compound | Structure | $A_{50}$[1] (uM; 95% CI) | $f_u$ in Plasma | $f_u$ in Brain |
|---|---|---|---|---|
| 1 (His-Tyr) | 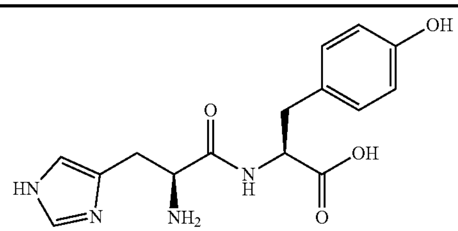 | 37.7 (24.5 to 58.6) | 0.66 ± 0.08 | N.D.[1] |
| 4 (His-Trp) | 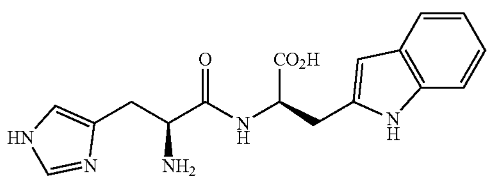 [SMILES: N[C@@H](Cc1c[nH]cn1)C(=O)N[C@H](Cc1cc2ccccc2[nH]1)C(=O)O] | 34 (24 to 48.12) | 0.93 ± 0.13 | N.D. |
| 9d | 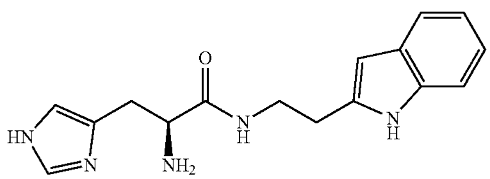 | 6.1 (3.7 to 10.12) | 0.63 ± 0.076 | 0.14 ± 0.012 |
| 10c | 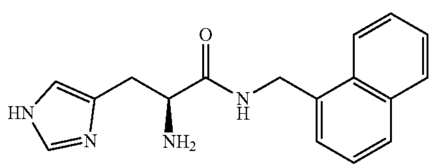 [SMILES: N[C@@H](Cc1c[nH]cn1)C(=O)NCc1cccc2ccccc12] | 4.2 (3.17 to 5.6) | 0.45 ± 0.013 | 0.052 ± 0.003 |
| 11a | 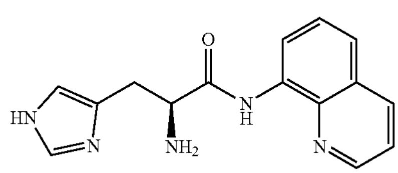 [SMILES: N[C@@H](Cc1c[nH]cn1)C(=O)Nc1cccc2cccnc12] | 4.4 (2.07 to 9.14) | 0.41 ± 0.081 | 0.062 ± 0.011 |

[1]Not determined.

Figure 15:
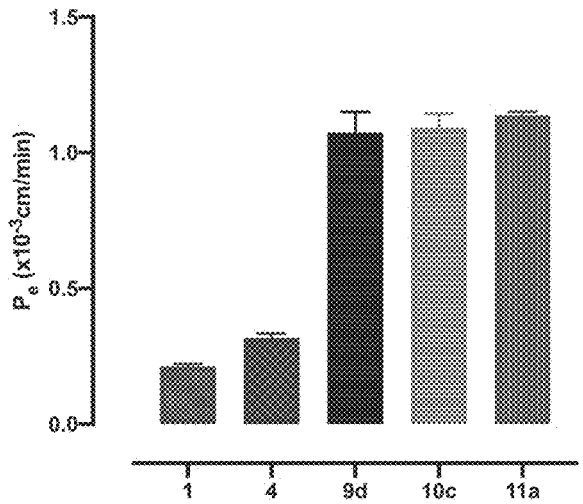
FIG. 15 is a graph that shows apical to basolateral transport of Nln activators at 10 µg/mL across an in vitro co-culture model of the BBB at 37° C. The permeability coefficient (Pe) was calculated from the cleared volume of each compound versus time. Values represent the mean±SD of three measurements.
Figure 16A:
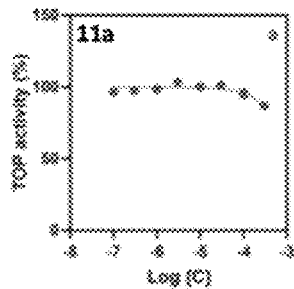
FIGS. 16A to 16L are graphs that show the effect of selected compounds on catalytic activity of human recombinant peptidases. All panels document concentration-dependent effect of the indicated compounds on hydrolysis of a respective quenched fluorescent substrate (n=4, mean±SD): Mca-Pro-Leu-Gly-Pro-D-Lys(DNP)-OH at 25 µM for thimet oligopeptidase (TOP; 16A, 16B, 16C), Mca-Arg-Pro-Pro-Gly-Phe-Ser-Ala-Phe-Lys(Dnp)-OH at 10 µM for neprilysin (NEP; 16D, 16E, 16F), Mca-Ala-Pro-Lys-(Dnp)-OH at 10 µM for angiotensin converting enzyme 2 (ACE2; 16G, 16H, 16I) and angiotensin converting enzyme (ACE; 16J, 16K, 16L). In all panels, the initial velocity of the hydrolysis in the absence of either compound corresponds to 100% on the vertical axis.
Figure 16B:
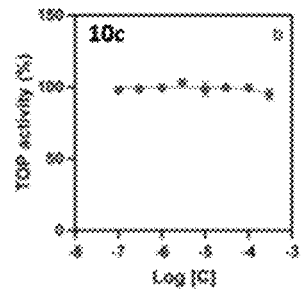
Figure 16C:
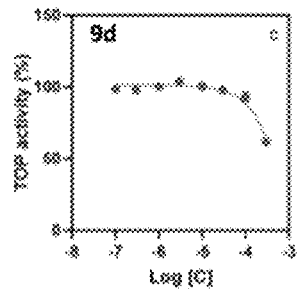
Figure 16D:
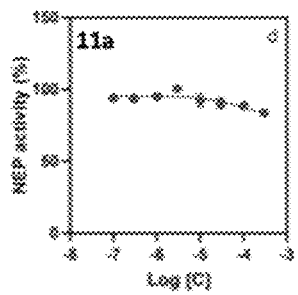
Figure 16E:
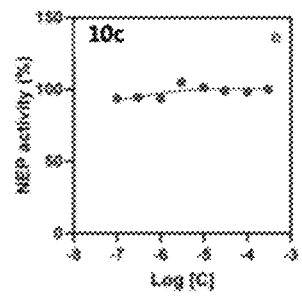
Figure 16F:
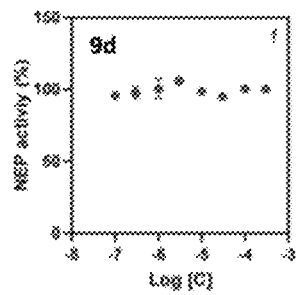
Figure 16G:
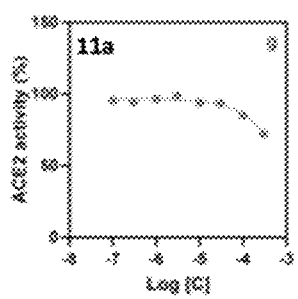
Figure 16H:
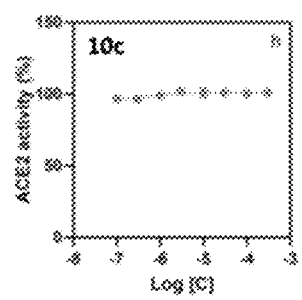
Figure 16I:
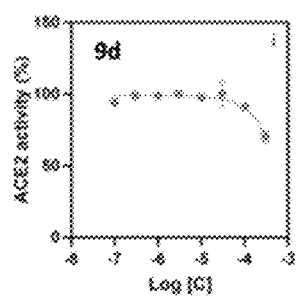
Figure 16J:
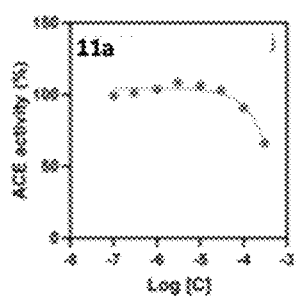
Figure 16K:
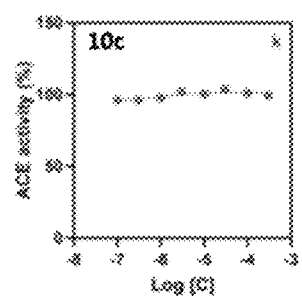
Figure 16L:
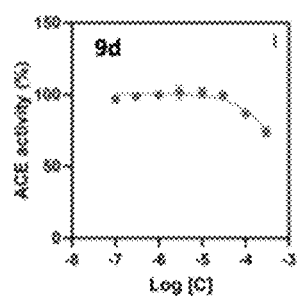

In Vitro Blood-Brain Barrier Permeability. To determine blood-brain barrier permeability, compounds 1, 4, 9d, 10c and 11a were added to the luminal compartment of an established co-culture system and their progressive transfer through the cells was monitored. As seen in FIG. 15, a significant increase in the apical to basolateral transport of peptidomimetic activators of Nln compared to that of the dipeptide hit compounds 1 and 4 was observed (FIG. 15). The Pe values for peptidomimetic derivatives 9d, 10c and 11a (1.07±0.12×10$^{-3}$, 1.09±0.09×10$^{-3}$ and 1.14±0.02×10$^{-3}$ cm/min) were 4-5-fold higher than permeability values of hit compounds 1 and 4 (0.21±0.01×10$^{-3}$, 0.32±0.3×10$^{-3}$ cm/min) indicating substantially increased BBB penetration. FIG. 15 is a graph that shows the apical to basolateral transport of Nln activators at 10 µg/mL across an in vitro PEPTIDASE SELECTIVITY. The effect of selected derivatives 9d, 10c and 11a to inhibit the highly related peptidases thimet oligopeptidase (TOP), neprilysin (NEP), angiotensin converting enzyme 2 (ACE2) and ACE, which together with Nln belong to the same family of enzymes, was determined in an eight-point concentration-response experiment (FIGS. 16A to 16L). No appreciable inhibition of TOP was encountered for 10a and 10c, while 9d only exhibited inhibition at concentrations approaching 300 M (FIGS. 16A-C). None of the three compounds show appreciable inhibition of NEP (FIGS. 16D-F). Compounds 9d and 11a showed inhibition of ACE2 at high concentrations while 10c showed no inhibition up to 300 µM (FIGS. 16G-I). Similarly, 9d and 11a show inhibition of ACE at high concentration while 10c shows no inhibition at the maximum concentration tested (FIGS. 16J-L). These data demonstrate the high selectivity of our developed peptidomimetic neurolysin activators, providing no detectable activation of TOP, NEP, ACE or ACE2 and inhibition activity only at high micromolar.

FIGS. 16A to 16L are graphs that show the effect of selected compounds on catalytic activity of human recombinant peptidases. All panels document concentration-dependent effect of the indicated compounds on hydrolysis of a respective quenched fluorescent substrate (n=4, mean±SD): Mca-Pro-Leu-Gly-Pro-D-Lys(DNP)-OH at 25 µM for thimet oligopeptidase (TOP; 16A, 16B, 16C), Mca-Arg-Pro-Pro-Gly-Phe-Ser-Ala-Phe-Lys(Dnp)-OH at 10 µM for neprilysin (NEP; panels 16D, 16E, 16F), Mca-Ala-Pro-Lys-(Dnp)-OH at 10 µM for angiotensin converting enzyme 2 (ACE2; panels 16G, 16H, 16I) and angiotensin converting enzyme (ACE; panels 16J, 16K, 16L). In all panels, the initial velocity of the hydrolysis in the absence of either compound corresponds to 100% on the vertical axis.

General Synthetic Procedures. Solvents and reagents of commercial grade were purchased from Fisher Scientific, VWR or Sigma-Aldrich and were used without additional purification. All reactions were performed in oven dried flasks under nitrogen atmosphere. Reaction progress was monitored using thin-layer chromatography (TLC) on Aluminium-backed 20 µm silica plates supplied by Silicycle (TLA-R10011B-323) and visualized by UV (254 nm) or staining agent (ninhydrin solution, phosphomolybdic acid or iodine vapor). Flash column chromatography was performed on silica gel (40-63 µm, 60 Å) with the indicated mobile phase. Specific rotations of enantiomers were measured at 589 nm with a LAXCO polarimeter model Pol-301. The volume of the cell was 11 mL, and the path length was 1.0 dm. NMR spectrometric analysis were carried out using the indicated solvent on a Bruker Avance III HD spectrometer at 400 or 500 MHz for proton (H) and 100 or 126 MHz for carbon ($^{13}$C), respectively. Chemical shifts (δ) are recorded in parts per million (ppm) and reported relative to solvents, coupling constants (J) are reported in hertz (Hz). Splitting of signal peaks are indicated by s (singlet), d (doublet), dd (doublet of doublets), t (triplet), q (quartet), m (multiplet), and br (broad). High-resolution mass spectrometry (HRMS) was carried out on an Agilent 1200 time-of-flight mass spectrometer equipped with electrospray ionization source. High-performance liquid chromatography (HPLC) was performed on an Agilent 1220, equipped with a 254 nm UV detector (VWD), employing a Phenomenex C18, Polar-RP column (4 µm, 250×4.6 mm) or RP column (5 µm, 250×4.6 mm). Purifications were performed using methanol:water (0.05% TFA) as mobile phase. Purity of all final compounds was determined as >95%, unless otherwise specified.

General Procedure A (Synthesis of Boc Protected Intermediates): Under an inert atmosphere Boc-L or D-Histidine (1.1 mmol), BOP (1 mmol) and DIPEA (2 mmol) were suspended in DMF (6 mL) and the mixture was heated to 50° C. and stirred for 1 hour. In a separate vessel, the respective amine (1 mmol) was dissolved in DMF (4 mL) by stirring at room temperature for 30 minutes. The amine solution was then added to the Boc-Histidine solution and stirred overnight at 50° C. The reaction mixture was cooled and extracted with ethyl acetate and washed with saturated aqueous sodium bicarbonate and brine. The organic phase was collected, dried over anhydrous $Na_2SO_4$ and concentrated in vacuo. The desired Boc-protected intermediate was then isolated from the crude extract by flash column chromatography (Mobile phase: 0%-20% MeOH in DCM).

General Procedure B (Boc Deprotection): The Boc-protected intermediate was dissolved in 20% TFA in DCM (10 mL) and stirred at room temperature for 3 hours. The solvent was evaporated in vacuo. DCM (20 mL) was added to the residue, perturbed and then evaporated (×3). The residue was dissolved in ethyl acetate (50 mL), basified (NaOH/$NaHCO_3$ aqueous solution) to pH 7, the organic layer separated, dried over anhydrous $Na_2SO_4$, concentrated in vacuo and purified by flash column chromatography using MeOH:DCM as mobile phase.

(S)-2-amino-3-(1H-imidazol-4-yl)-N-phenethylpropanamide (4c): Following general synthetic method B the title compound was synthesized as a colorless oil (71%). $R_f$=0.14 (MeOH:DCM=1:9). $^1$H NMR (400 MHz, MeOH-$d_4$) $δ_H$: 2.74-2.80 (m, 3H), 2.92-2.97 (m, 1H), 3.37-3.47 (m, 2H), 3.55-3.59 (m, 1H), 6.86 (s, 1H), 7.18-7.21 (m, 3H), 7.26-7.30 (m, 2H), 7.62 (s, 1H); $^{13}$C NMR (100 MHz, MeOH-$d_4$) $δ_C$: 32.10, 35.09, 40.43, 54.82, 116.91, 125.99, 128.12, 128.38, 133.55, 134.99, 138.99, 174.53. HRMS (ESI) calc. for $C_{14}H_{19}N_4O$ [M+H]$^+$ 259.1553. found 259.1560.

(R)-2-amino-3-(1H-imidazol-4-yl)-N-phenethylpropanamide (4d): Following general synthetic method B the title compound was synthesized as a colorless oil (62%). $R_f$=0.12 (MeOH:DCM=1:9). 1H NMR (400 MHz, MeOH-$d_4$) $δ_H$: 2.78-2.83 (m, 2H), 3.19-3.30 (m, 2H), 3.41-3.59 (m, 2H), 4.18 (t, J=6.8 Hz, 1H), 7.21-7.31 (m, 6H), 8.79 (s, 1H); $^{13}$C NMR (100 MHz, MeOH-$d_4$) $δ_C$: 26.45, 34.75, 40.66, 52.00, 117.95, 126.13, 127.15, 128.18, 128.34, 134.44, 138.67, 167.16. HRMS (ESI) calc. for $C_{14}H_{19}N_4O$ [M+H]$^+$ 259.1553. found 259.1560.

(S)-2-amino-3-(1H-imidazol-4-yl)-N-(4-methoxyphenethyl)propanamide (4e): Following general synthetic method B the title compound was synthesized as a colorless oil (59%). $R_f$=0.14 (MeOH:DCM=1:9). $^1$H NMR (400 MHz, MeOH-$d_4$) $δ_H$: 2.71-2.76 (m, 2H), 3.19-3.29 (m, 2H), 3.35-3.38 (m, 2H), 3.76 (s, 3H), 4.17 (t, J=6.8 Hz, 1H), 6.85 (d, J=8.8 Hz, 2H), 7.13 (d, J=8.8 Hz, 2H), 7.31 (s, 1H), 8.80 (d, J=1.2 Hz, 1H); $^{13}$C NMR (100 MHz, MeOH-$d_4$) $δ_C$: 26.48, 33.93, 40.90, 51.97, 54.25, 113.58, 117.93, 127.19, 129.29, 130.55, 134.47, 158.45, 167.10. HRMS (ESI) calc. for $C_{15}H_{21}N_4O_2$ [M+H]$^+$ 289.1659. found 289.1665.

(R)-2-amino-3-(1H-imidazol-4-yl)-N-(4-methoxyphenethyl)propanamide (4f): Following general synthetic method B the title compound was synthesized as a colorless oil (60%). $R_f$=0.10 (MeOH:DCM=1:9). $^1$H NMR (400 MHz, MeOH-$d_4$) $δ_H$: 2.74-2.78 (m, 2H), 3.23-3.32 (m, 2H), 3.42-3.54 (m, 2H), 3.79 (s, 3H), 4.17-4.20 (m, 1H), 6.86-6.88 (m, 2H), 7.15 (d, J=8.23 Hz, 2H), 7.36 (s, 1H), 8.89 (d, J=1.28 Hz, 1H); $^{13}$C NMR (100 MHz, MeOH-$d_4$) $δ_C$: 24.65, 32.24, 39.22, 50.23, 52.57, 111.90, 116.40, 125.19, 127.61, 128.87, 132.69, 156.77, 165.37. HRMS (ESI) calc. for $C_{15}H_{21}N_4O_2$ [M+H]$^+$ 289.1659. found 289.1659.

(S)-2-amino-3-(1H-imidazol-4-yl)-N-(2-methoxyphenethyl)propanamide (4g): Following general synthetic method B the title compound was synthesized as a colorless oil (61%). $R_f$=0.10 (MeOH:DCM=1:9). $^1$H NMR (400 MHz, MeOH-$d_4$) $δ_H$: 2.74-2.85 (m, 2H), 3.19-3.31 (m, 2H), 3.38-3.45 (m, 1H), 3.50-3.57 (m, 1H), 3.84 (s, 3H), 4.15 (t, J=6.87 Hz, 1H), 6.84-6.89 (m, 1H), 6.95 (d, J=8.05 Hz, 1H), 7.11 (dd, J=1.65, 7.39 Hz, 1H), 7.21 (td, J=1.50, 7.83 Hz, 1H), 7.31 (d, J=0.90 Hz, 1H), 8.82 (d, J=1.31 Hz, 1H); $^{13}$C NMR (100 MHz, MeOH-$d_4$) $δ_C$: 26.43, 29.81, 39.21, 51.97, 54.39, 110.19, 117.95, 120.12, 126.53, 127.10, 127.71, 129.98, 134.45, 157.68, 166.98. HRMS (ESI) calc. for $C_{15}H_{21}N_4O_2$ [M+H]$^+$ 289.1659. found 289.1655.

(R)-2-amino-3-(1H-imidazol-4-yl)-N-(2-methoxyphenethyl)propanamide (4h): Following general synthetic method B the title compound was synthesized as a colorless oil (63%). $R_f$=0.10 (MeOH:DCM=1:9). $^1$H NMR (400

MHz, MeOH-d$_4$) δ$_H$: 2.74-2.85 (m, 2H), 3.20-3.29 (m, 2H), 3.37-3.45 (m, 1H), 3.50-3.57 (m, 1H), 3.84 (s, 3H), 4.16 (t, J=6.87 Hz, 1H), 6.86 (td, J=0.88, 7.40 Hz, 1H), 6.94 (d, J=8.02 Hz, 1H), 7.11 (dd, J=1.60, 740 Hz, 1H), 7.21 (td, J=1.45, 7.83 Hz, 1H), 7.32 (s, 1H), 8.85 (d, J=1.22 Hz, 1H); $^{13}$C NMR (100 MHz, MeOH-d$_4$) δ$_C$: 26.35, 29.80, 39.20, 51.95, 54.39, 110.19, 118.04, 120.12, 126.55, 126.94, 127.71, 130.00, 134.40, 157.69, 166.99. HRMS (ESI) calc. for C$_{15}$H$_{21}$N$_4$O$_2$ [M+H]$^+$ 289.1659. found 289.1660.

(S)-2-amino-3-(1H-imidazol-4-yl)-N-(3-methoxyphenethyl)propanamide (4i): Following general synthetic method B the title compound was synthesized as a colorless oil (65%). R$_f$=0.10 (MeOH:DCM=1:9). $^1$H NMR (400 MHz, MeOH-d$_4$) δ$_H$: 2.75-2.81 (m, 2H), 3.19-3.28 (m, 2H), 3.41-3.48 (m, 1H), 3.56 (dt, J=7.55, 13.44 Hz, 1H), 3.78 (s, 3H), 4.16 (t, J=6.85 Hz, 1H), 6.77-6.80 (m, 3H), 7.21 (dd, J=7.32, 8.89 Hz, 1H), 7.31 (d, J=0.69 Hz, 1H), 8.81 (d, J=1.28 Hz, 1H); $^{13}$C NMR (100 MHz, MeOH-d$_4$) δ$_C$: 26.48, 34.79, 40.57, 51.96, 54.21, 111.43, 114.12, 117.88, 120.64, 127.18, 129.19, 134.50, 140.17, 159.94, 167.08. HRMS (ESI) calc. for C$_{15}$H$_{21}$N$_4$O$_2$ [M+H]$^+$ 289.1659. found 289.1659.

(R)-2-amino-3-(1H-imidazol-4-yl)-N-(3-methoxyphenethyl)propanamide (4j): Following general synthetic method B the title compound was synthesized as a colorless oil (63%). R$_f$=0.10 (MeOH:DCM=1:9). $^1$H NMR (400 MHz, MeOH-d$_4$) δ$_H$: 2.76-2.81 (m, 2H), 3.19-3.29 (m, 2H), 3.41-3.48 (m, 1H), 3.52-3.57 (m, 1H), 3.78 (s, 3H), 4.16 (t, J=6.85 Hz, 1H), 6.77-6.80 (m, 3H), 7.19-7.23 (m, 1H), 7.31 (d, J=0.68 Hz, 1H), 8.81 (d, J=1.23 Hz, 1H); $^{13}$C NMR (100 MHz, MeOH-d$_4$) δ$_C$: 260.42, 340.79, 40.57, 51.91, 540.19, 111.42, 114.09, 117.94, 120.63, 127.03, 129.19, 134.49, 140.17, 159.93, 167.07. HRMS (ESI) calc. for C$_{15}$H$_{21}$N$_4$O$_2$ [M+H]$^+$ 289.1659. found 289.1661.

(S)-2-amino-3-(1H-imidazol-4-yl)-N-(4-(trifluoromethyl)phenethyl)propenamide (4k): Following general synthetic method B the title compound was synthesized as a colorless oil (49%). R$_f$=0.17 (MeOH:DCM=1:9). $^1$H NMR (400 MHz, MeOH-d$_4$) δ$_H$: 2.91 (t, J=7.2 Hz, 2H), 3.21-3.27 (m, 2H), 3.54 (t, J=7.4 Hz, 2H), 4.18 (t, J=7.0 Hz, 1H), 7.40-7.44 (m, 3H), 7.61 (d, J=8.0 Hz, 2H), 8.88 (d, J=1.2 Hz, 1H); $^{13}$C NMR (100 MHz, MeOH-d$_4$) δ$_C$: 26.34, 34.59, 40.29, 51.88, 118.11, 125.00, 125.04, 126.90, 129.07, 134.51, 143.39, 167.15. HRMS (ESI) calc. for C$_{15}$H$_{15}$F$_3$N$_4$O [M+H]$^+$ 327.1427. found 327.1595.

(R)-2-amino-3-(1H-imidazol-4-yl)-N-(4-(trifluoromethyl)phenethyl)propanamide (4l): Following general synthetic method B the title compound was synthesized as a colorless oil (46%). R$_f$=0.16 (MeOH:DCM=1:9). 1H NMR (400 MHz, DMSO-d$_6$) δ$_H$: 2.77-2.81 (m, 2H), 3.03-3.16 (m, 2H), 3.32-3.39 (m, 1H), 3.40-3.45 (m, 1H), 4.04 (t, J=6.6 Hz, 1H), 7.37 (s, 1H), 7.42 (d, J=8.0 Hz, 2H), 7.65 (d, J=8.0 Hz, 2H), 8.58 (t, J=5.6 Hz, 1H), 8.90 (s, 1H); $^{13}$C NMR (100 MHz, DMSO-d$_6$): δ$_C$: 27.11, 34.92, 51.88, 118.10, 125.60, 125.64, 129.95, 135.01, 144.48, 167.65. HRMS (ESI) calc. for C$_{15}$H$_{18}$F$_3$N$_4$O [M+H]$^+$ 327.1427. found 327.1433.

(S)-2-amino-N-(4-fluorophenethyl)-3-(1H-imidazol-4-yl)propanamide (4m): Following general synthetic method B the title compound was synthesized as a colorless oil (61%). R$_f$=0.14 (MeOH:DCM=1:9). $^1$H NMR (400 MHz, MeOH-d$_4$) δ$_H$: 2.79 (t, J=7.4 Hz, 2H), 3.14-3.25 (m, 2H), 3.41-3.54 (m, 2H), 4.19 (t, J=7.0 Hz, 1H), 7.02 (t, J=8.8 Hz, 2H), 7.22-7.25 (m, 2H), 7.37 (s, 1H), 8.86 (d, J=1.6 Hz, 1H); $^{13}$C NMR (100 MHz, MeOH-d$_4$) δ$_C$: 26.38, 33.97, 40.72, 51.92, 114.70, 118.05, 126.99, 129.99, 130.07, 134.5, 134.62, 161.6, 167.12. HRMS (ESI) calc. for C$_{14}$H$_{18}$FN$_4$O [M+H]$^+$ 277.1459. found 277.1461.

(R)-2-amino-N-(4-fluorophenethyl)-3-(1H-imidazol-4-yl)propanamide (4n): Following general synthetic method B the title compound was synthesized as a colorless oil (58%). R$_f$=0.13 (MeOH:DCM=1:9). $^1$H NMR (400 MHz, MeOH-d$_4$) δ$_H$: 2.69 (t, J=7.0 Hz, 2H), 2.84-3.31 (m, 4H), 4.10 (t, J=6.8 Hz, 1H), 6.90 (t, J=8.8 Hz, 2H), 7.11-7.14 (t, J=5.6 Hz, 2H), 7.29 (s, 1H), 8.76 (d, J=0.8 Hz, 1H); $^{13}$C NMR (100 MHz, MeOH-d$_4$) δ$_C$: 26.53, 33.97, 40.73, 52.01, 114.7, 117.93, 127.32, 130.0, 134.53, 161.08, 167.21. HRMS (ESI) calc. for C$_{14}$H$_{18}$FN$_4$O [M+H]$^+$ 277.1459. found 277.1465.

(S)-2-amino-3-(1H-imidazol-4-yl)-N-(4-nitrophenethyl)propanamide (4o): Following general synthetic method B the title compound was synthesized as a colorless oil (60%). R$_f$=0.06 (MeOH:DCM=1:9). $^1$H NMR (500 MHz, MeOH-d$_4$) δ$_H$: 2.96 (t, J=7.21 Hz, 2H), 3.22-3.36 (m, 2H), 3.57 (t, J=7.17 Hz, 2H), 4.19 (t, J=6.92 Hz, 1H), 7.41 (d, J=1.10 Hz, 1H), 7.49 (d, J=8.72 Hz, 2H), 8.18-8.19 (m, 2H), 8.89 (d, J=1.35 Hz, 1H); $^{13}$C NMR (126 MHz, MeOH-d$_4$) δ$_C$: 26.37, 34.60, 40.04, 51.96, 118.17, 123.21, 126.95, 129.56, 134.44, 146.75, 146.83, 167.29. HRMS (ESI) calc. for C$_{14}$H$_{18}$N$_5$O$_3$ [M+H]$^+$ 304.1404. found 304.1407.

(R)-2-amino-3-(1H-imidazol-4-yl)-N-(4-nitrophenethyl)propanamide (4p): Following general synthetic method B the title compound was synthesized as a colorless oil (61%). R$_f$=0.06 (MeOH:DCM=1:9). $^1$H NMR (500 MHz, MeOH-d$_4$) δ$_H$: 2.96 (t, J=7.22 Hz, 2H), 3.22-3.36 (m, 2H), 3.56 (t, J=7.22 Hz, 2H), 4.20 (t, J=6.93 Hz, 1H), 7.41 (d, J=1.13 Hz, 1H), 7.49 (d, J=8.72 Hz, 2H), 8.17-8.19 (m, 2H), 8.89 (d, J=1.36 Hz, 1H); $^{13}$C NMR (126 MHz, MeOH-d$_4$) δ$_C$: 26.38, 34.59, 40.05, 52.02, 118.21, 123.22, 126.96, 129.55, 134.42, 146.71, 146.86, 167.33. HRMS (ESI) calc. for C$_{14}$H$_{18}$N$_5$O$_3$ [M+H]$^+$ 304.1404. found 304.1414.

(S)—N-(2-([1,1'-biphenyl]-4-yl)ethyl)-2-amino-3-(1H-imidazol-4-yl)propanamide (4q): Following general synthetic method B the title compound was synthesized as a colorless oil (63%). R$_f$=0.14 (MeOH:DCM=1:9). $^1$H NMR (500 MHz, MeOH-d$_4$) δ$_H$: 2.85-2.88 (m, 2H), 3.22-3.31 (m, 2H), 3.48-3.61 (m, 2H), 4.18 (t, J=6.00 Hz, 1H), 7.31-7.35 (m, 4H), 7.43 (t, J=7.69 Hz, 2H), 7.56-7.60 (m, 4H), 8.85 (s, 1H); $^{13}$C NMR (126 MHz, MeOH-d$_4$) δ$_C$: 26.39, 34.44, 40.65, 51.91, 118.04, 126.39, 126.74, 126.90, 128.47, 128.88, 134.48, 137.78, 139.41, 140.65, 167.05. HRMS (ESI) calc. for C$_{20}$H$_{23}$N$_4$O [M+H]$^+$ 335.1866. found 335.1869.

(R)—N-(2-([1,1'-biphenyl]-4-yl)ethyl)-2-amino-3-(1H-imidazol-4-yl)propanamide (4r): Following general synthetic method B the title compound was synthesized as a colorless oil (62%). R$_f$=0.14 (MeOH:DCM=1:9). $^1$H NMR (500 MHz, MeOH-d$_4$) δ$_H$: 2.84-2.88 (m, 2H), 3.22-3.31 (m, 2H), 3.48-3.61 (m, 2H), 4.19 (t, J=6.85 Hz, 1H), 7.31-7.35 (m, 4H), 7.43 (t, J=7.76 Hz, 2H), 7.56-7.60 (m, 4H), 8.85 (s, 1H); $^{13}$C NMR (126 MHz, MeOH-d$_4$) δ$_C$: 26.35, 34.43, 40.65, 51.93, 118.11, 126.40, 126.73, 126.87, 128.46, 128.90, 134.39, 137.80, 139.37, 140.67, 167.12. HRMS (ESI) calc. for C$_{20}$H$_{23}$N$_4$O [M+H]$^+$ 335.1866. found 335.1868.

(S)-2-amino-N-benzyl-3-(1H-imidazol-4-yl)propanamide (5a): Following general synthetic method B the title compound was synthesized as a colorless oil (67%). R$_f$=0.13 (MeOH:DCM=1:9). $^1$H NMR (400 MHz, MeOH-d$_4$) δ$_H$: 3.32-3.33 (m, 2H), 4.19-4.22 (m, 1H), 4.39 (dd, J=14.6, 44.6 Hz, 2H), 7.24-7.36 (m, 6H), 8.80 (s, 1H); $^{13}$C NMR (100 MHz, MeOH-d$_4$) δ$_C$: 26.23, 43.01, 52.00, 118.09, 126.80, 127.26, 127.56, 128.29, 134.32, 137.77, 166.81. HRMS (ESI) calc. for C$_{13}$H$_{17}$N$_4$O [M+H]$^+$ 245.1397. found 245.1570.

(S)-2-amino-3-(1H-3l4-imidazol-4-yl)-N-(4-methoxybenzyl)propanamide (5b): Following general synthetic method B the title compound was synthesized as a colorless oil (65%). $R_f$=0.10 (MeOH:DCM=1:9). $^1$H NMR (400 MHz, MeOH-$d_4$) $\delta_H$: 3.30-3.32 (m, 2H), 3.80 (s, 3H), 4.18 (t, J=7.06 Hz, 1H), 4.27 (d, J=14.46 Hz, 1H), 4.38 (d, J=14.47 Hz, 1H), 6.89 (d, J=8.68 Hz, 2H), 7.17 (d, J=8.64 Hz, 2H), 7.30 (d, J=0.68 Hz, 1H), 8.75 (d, J=1.24 Hz, 1H); $^{13}$C NMR (100 MHz, MeOH-$d_4$) $\delta_C$: 26.44, 42.48, 52.09, 54.30, 113.60, 117.89, 127.22, 128.91, 129.68, 134.41, 159.28, 166.73. HRMS (ESI) calc. for $C_{14}H_{19}N_4O_2$ [M+H]$^+$ 275.1503. found 275.1506.

(R)-2-amino-3-(1H-imidazol-4-yl)-N-(4-methoxybenzyl)propanamide (5c): Following general synthetic method B the title compound was synthesized as colorless oil (68%). $R_f$=0.13 (MeOH:DCM=1:9). 1H NMR (400 MHz, MeOH-$d_4$) $\delta_H$: 2.81-2.86 (m, 1H), 2.96-3.01 (m, 1H), 3.62 (t, J=6.8 Hz, 1H), 3.78 (s, 3H), 4.23-4.35 (m, 2H), 6.85-6.87 (m, 3H), 7.12 (d, J=6.8 Hz, 2H), 7.60 (s, 1H); $^{13}$C NMR (100 MHz, MeOH-$d_4$) $\delta_C$: 32.99, 42.08, 54.29, 54.97, 113.48, 117.02, 128.48, 130.26, 133.52, 134.94, 159.01, 174.56. HRMS (ESI) calc. for $C_{14}H_{19}N_4O_2$ [M+H]$^+$ 275.1503. found 275.1439.

(S)-2-amino-3-(1H-3l4-imidazol-4-yl)-N-(2-methoxybenzyl)propanamide (5d): Following general synthetic method B the title compound was synthesized as a colorless oil (66%). $R_f$=0.10 (MeOH:DCM=1:9). $^1$H NMR (500 MHz, MeOH-$d_4$) $\delta_H$: 3.31 (d, J=7.15 Hz, 2H), 3.85 (s, 3H), 4.24 (t, J=7.10 Hz, 1H), 4.32 (d, J=14.42 Hz, 1H), 4.46 (d, J=14.42 Hz, 1H), 6.91 (t, J=7.44 Hz, 1H), 6.98 (d, J=8.17 Hz, 1H), 7.19 (dd, J=7.43, 1.51 Hz, 1H), 7.25 (s, 1H), 7.30 (td, J=7.85, 1.43 Hz, 1H), 8.76 (d, J=1.28 Hz, 1H); $^{13}$C NMR (126 MHz, MeOH-$d_4$) $\delta_C$: 26.26, 38.55, 51.86, 54.47, 110.20, 117.97, 120.05, 125.23, 126.82, 128.91, 129.17, 134.18, 157.44, 166.81. HRMS (ESI) calc. for $C_{14}H_{19}N_4O_2$ [M+H]$^+$ 275.1503. found 275.1521.

(R)-2-amino-3-(1H-3l4-imidazol-4-yl)-N-(2-methoxybenzyl)propanamide (5e): Following general synthetic method B the title compound was synthesized as a colorless oil (62%). $R_f$=0.10 (MeOH:DCM=1:9). $^1$H NMR (400 MHz, MeOH-$d_4$) $\delta_H$: 3.30 (d, J=7.12 Hz, 2H), 3.85 (s, 3H), 4.22 (t, J=7.08 Hz, 1H), 4.32 (d, J=14.43 Hz, 1H), 4.46 (d, J=14.43 Hz, 1H), 6.92 (t, J=7.45 Hz, 1H), 6.98 (d, J=8.19 Hz, 1H), 7.19 (dd, J=1.56, 7.44 Hz, 1H), 7.23 (d, J=0.60 Hz, 1H), 7.28-7.32 (m, 1H), 8.70 (d, J=1.22 Hz, 1H); $^{13}$C NMR (100 MHz, MeOH-$d_4$) $\delta_C$: 26.39, 38.74, 52.10, 54.91, 110.59, 117.78, 120.34, 124.97, 126.83, 129.29, 129.36, 134.07, 157.32, 167.15. HRMS (ESI) calc. for $C_{14}H_{19}N_4O_2$ [M+H]$^+$ 275.1503. found 275.1507.

(S)-2-amino-3-(1H-3l4-imidazol-4-yl)-N-(3-methoxybenzyl)propanamide (5f): Following general synthetic method B the title compound was synthesized as a colorless oil (60%). $R_f$=0.10 (MeOH:DCM=1:9). $^1$H NMR (500 MHz, MeOH-$d_4$) $\delta_H$: 3.30-3.39 (m, 2H), 3.80 (s, 3H), 4.22 (t, J=7.08 Hz, 1H), 4.31 (d, J=14.67 Hz, 1H), 4.42 (d, J=14.66 Hz, 1H), 6.79-6.82 (m, 2H), 6.86 (dd, J=8.20, 2.32 Hz, 1H), 7.25 (t, J=7.89 Hz, 1H), 7.34 (s, 1H), 8.81 (s, 1H); $^{13}$C NMR (126 MHz, MeOH-$d_4$) $\delta_C$: 26.26, 42.93, 52.02, 54.29, 112.36, 113.35, 118.11, 119.65, 126.81, 129.35, 134.29, 139.24, 159.97, 166.89. HRMS (ESI) calc. for $C_{14}H_{19}N_4O_2$ [M+H]$^+$ 275.1503. found 275.1529.

(R)-2-amino-3-(1H-3l4-imidazol-4-yl)-N-(3-methoxybenzyl)propanamide (5g): Following general synthetic method B the title compound was synthesized as a colorless oil (58%). $R_f$=0.10 (MeOH:DCM=1:9). $^1$H NMR (400 MHz, MeOH-$d_4$) $\delta_H$: 3.34-3.36 (m, 2H), 3.80 (s, 3H), 4.23 (t, J=7.08 Hz, 1H), 4.33 (d, J=14.67 Hz, 1H), 4.43 (d, J=14.67 Hz, 1H), 6.79-6.88 (m, 3H), 7.25 (t, J=7.90 Hz, 1H), 7.34 (s, 1H), 8.81 (d, J=1.2 Hz, 1H); $^{13}$C NMR (100 MHz, MeOH-$d_4$) $\delta_C$: 24.65, 41.32, 50.40, 52.67, 110.73, 111.77, 116.49, 118.04, 125.20, 127.74, 132.71, 137.64, 158.37, 165.24. HRMS (ESI) calc. for $C_{14}H_{19}N_4O_2$ [M+H]$^+$ 275.1503. found 275.1503.

(S)-2-amino-3-(1H-imidazol-4-yl)-N-(4-(trifluoromethyl)benzyl)propanamide (5h): Following general synthetic method B the title compound was synthesized as a colorless oil (55%). $R_f$=0.14 (MeOH:DCM=1:9). $^1$H NMR (400 MHz, MeOH-$d_4$) $\delta_H$: 3.36-3.44 (m, 2H), 4.28 (t, J=7.0 Hz, 1H), 4.50 (q, J=12.9 Hz, 2H), 7.42 (s, 1H), 7.46 (d, J=8.0 Hz, 2H), 7.64 (d, J=8.0 Hz, 2H), 8.86 (d, J=1.2 Hz, 1H); $^{13}$C NMR (100 MHz, MeOH-$d_4$) $\delta_C$: 26.30, 42.49, 52.04, 118.16, 125.09, 125.58, 126.99, 127.15, 127.94, 134.47, 142.39, 167.23. HRMS (ESI) calc. for $C_{14}H_{16}F_3N_4O$ [M+H]$^+$ 313.1271. found 313.1440.

(R)-2-amino-3-(1H-imidazol-4-yl)-N-(4-(trifluoromethyl)benzyl)propanamide (5i): Following general synthetic method B the title compound was synthesized as a colorless oil (59%). $R_f$=0.13 (MeOH:DCM=1:9). 1H NMR (400 MHz, MeOH-$d_4$) $\delta_H$: 3.39-3.45 (m, 2H), 4.29 (t, J=6.8 Hz, 1H), 4.50 (q, J=13.6 Hz, 2H), 7.45 (t, J=8.8 Hz, 3H), 7.63 (d, J=8.0 Hz, 2H), 8.86 (d, J=0.8 Hz, 1H); $^{13}$C NMR (100 MHz, MeOH-$d_4$) $\delta_C$: 26.33, 42.49, 52.06, 118.14, 122.89, 125.07, 125.11, 125.14, 125.58, 127.04, 127.93, 129.15, 129.47, 134.48, 142.39, 167.24. HRMS (ESI) calc. for $C_{14}H_{16}F_3N_4O$ [M+H]$^+$ 313.1271. found 313.1284.

(S)-2-amino-3-(1H-imidazol-4-yl)-N-(2-(trifluoromethyl)benzyl)propanamide (5j): Following general synthetic method B the title compound was synthesized as a white solid (61%). $R_f$=0.13 (MeOH:DCM=1:9). $^1$H NMR (400 MHz, MeOH-$d_4$) $\delta_H$: 3.34-3.43 (m, 2H), 4.29 (t, J=7.05 Hz, 1H), 4.62 (s, 2H), 7.39 (d, J=1.27 Hz, 1H), 7.50 (t, J=7.36 Hz, 2H), 7.63 (t, J=7.56 Hz, 1H), 7.72 (d, J=7.43 Hz, 1H), 8.87 (d, J=1.35 Hz, 1H); $^{13}$C NMR (100 MHz, MeOH-$d_4$) $\delta_C$: 26.27, 39.70, 39.73, 51.92, 118.15, 125.65, 125.71, 125.76, 126.89, 127.69, 127.80, 129.69, 132.22, 134.44, 135.67, 167.22. HRMS (ESI) calc. for $C_{14}H_{16}F_3N_4O$ [M+H]$^+$ 313.1271. found 313.1274.

(R)-2-amino-3-(1H-imidazol-4-yl)-N-(2-(trifluoromethyl)benzyl)propanamide (5k): Following general synthetic method B the title compound was synthesized as a white solid (65%). $R_f$=0.13 (MeOH:DCM=1:9). $^1$H NMR (500 MHz, MeOH-$d_4$) $\delta_H$: 3.35-3.43 (m, 2H), 4.31 (t, J=7.06 Hz, 1H), 4.62 (s, 2H), 7.39 (s, 1H), 7.49 (dd, J=7.43, 4.84 Hz, 2H), 7.62 (t, J=7.50 Hz, 1H), 7.72 (d, J=7.81 Hz, 1H), 8.87 (d, J=1.34 Hz, 1H); $^{13}$C NMR (126 MHz, MeOH-$d_4$) $\delta_C$: 26.27, 39.70, 39.72, 51.92, 118.16, 125.52, 125.66, 125.70, 126.90, 127.52, 127.69, 127.77, 129.68, 132.22, 134.44, 135.68, 167.23. HRMS (ESI) calc. for $C_{14}H_{16}F_3N_4O$ [M+H]$^+$ 313.1271. found 313.1281.

(S)-2-amino-3-(1H-imidazol-4-yl)-N-(3-(trifluoromethyl)benzyl)propanamide (5l): Following general synthetic method B the title compound was synthesized as a colorless oil (53%). $R_f$=0.11 (MeOH:DCM=1:9). $^1$H NMR (400 MHz, MeOH-$d_4$) $\delta_H$: 2.84 (dd, J=7.6, 14.4 Hz, 1H), 3.00 (dd, J=6.0, 14.4 Hz, 1H), 3.65 (t, J=6.6 Hz, 1H), 4.44 (q, J=15.2 Hz, 2H), 6.85 (s, 1H), 7.43-7.62 (m, 5H); $^{13}$C NMR (100 MHz, MeOH-$d_4$) $\delta_C$: 32.37, 42.08, 54.99, 116.78, 123.51, 123.55, 123.85, 123.89, 125.60, 128.90, 130.18, 130.91, 133.66, 134.96, 139.96, 175.09. HRMS (ESI) calc. for $C_{14}H_{16}F_3N_4O$ [M+H]$^+$ 313.1271. found 313.1280.

(R)-2-amino-3-(1H-imidazol-4-yl)-N-(3-(trifluoromethyl)benzyl)propanamide (5m): Following general synthetic method B the title compound was synthesized as a colorless oil (56%). $R_f$=0.15 (MeOH:DCM=1:9). $^1$H NMR (400 MHz, DMSO-d$_6$) δ$_H$: 3.14-3.27 (m, 2H), 4.20 (t, J=6.6 Hz, 1H), 4.36-4.49 (m, 2H), 7.83 (s, 1H), 7.49 (d, J=7.6 Hz, 1H), 7.54-7.64 (m, 3H), 8.92 (s, 1H), 9.13 (t, J=5.6 Hz, 1H); $^{13}$C NMR (100 MHz, DMSO-d$_6$) δ$_C$: 27.03, 42.48, 51.97, 118.15, 124.40, 124.44, 127.81, 129.87, 131.89, 134.99, 140.31, 167.90. HRMS (ESI) calc. for C$_{14}$H$_{16}$F$_3$N$_4$O [M+H]$^+$ 313.1271. found 313.1278.

(S)-2-amino-N-(4-fluorobenzyl)-3-(1H-imidazol-4-yl)propanamide (5n): Following general synthetic method B the title compound was synthesized as a colorless oil (62%). R$_f$=0.12 (MeOH:DCM=1:9). 1H NMR (400 MHz, MeOH-d$_4$) δ$_H$: 2.87 (dd, J=7.2, 14.4 Hz, 1H), 2.99 (dd, J=7.2, 14.4 Hz, 1H), 3.63 (t, J=6.8 Hz, 1H), 4.34 (q, J=16.4 Hz, 2H), 6.85 (s, 1H), 7.00-7.05 (m, 2H), 7.17-7.21 (m, 2H), 7.61 (s, 1H). $^{13}$C NMR (100 MHz, MeOH-d$_4$) δ$_C$: 32.34, 41.80, 55.02, 114.67, 116.96, 129.0, 133.59, 134.40, 134.95, 162.03, 174.84. HRMS (ESI) calc. for C$_{13}$H$_{16}$FN$_4$O [M+H]$^+$ 263.1303. found 263.1305.

(R)-2-amino-N-(4-fluorobenzyl)-3-(1H-imidazol-4-yl)propanamide (5o): Following general synthetic method B the title compound was synthesized as a colorless oil (68%). R$_f$=0.15 (MeOH:DCM=1:9). 1H NMR (400 MHz, MeOH-d$_4$) δ$_H$: 3.28-3.33 (m, 2H), 4.19 (t, J=7.2 Hz, 1H), 4.38 (q, J=12.2 Hz, 2H), 7.06 (t, J=8.8 Hz, 2H), 7.26-7.35 (m, 2H), 8.83 (s, 1H); $^{13}$C NMR (100 MHz, MeOH-d$_4$) δ$_C$: 26.33, 42.25, 52.06, 114.8, 118.06, 127.04, 129.5 133.86, 133.89, 134.41, 162.2, 166.96. HRMS (ESI) calc. for C$_{13}$H$_{16}$FN$_4$O M+H]$^+$263.1303. found 263.1305.

(S)-2-amino-3-(1H-imidazol-4-yl)-N-(4-(trifluoromethoxy)benzyl)propanamide (5p): Following general synthetic method B the title compound was synthesized as a colorless oil (76%). R$_f$=0.14 (MeOH:DCM=1:9). 1H NMR (400 MHz, MeOH-d$_4$) δ$_H$: 3.39-3.43 (m, 2H), 4.24 (t, J=7.0 Hz, 1H), 4.43 (q, J=12.4 Hz, 2H), 7.25 (d, J=8.4 Hz, 2H), 7.38 (t, J=8.6 Hz, 3H), 8.86 (d, J=1.2 Hz, 1H); $^{13}$C NMR (100 MHz, MeOH-d$_4$) δ$_C$: 26.26, 42.24, 52.02, 118.17, 120.81, 126.92, 129.22, 134.43, 137.12, 148.42, 167.05. HRMS (ESI) calc. for C$_{14}$H$_{16}$F$_3$N$_4$O$_2$ [M+H]$^+$ 329.1220. found 329.1386.

(R)-2-amino-3-(1H-imidazol-4-yl)-N-(4-(trifluoromethoxy)benzyl)propanamide (5q): Following general synthetic method B the title compound was synthesized as a colorless oil (78%). R$_f$=0.12 (MeOH:DCM=1:9). $^1$H NMR (400 MHz, MeOH-d$_4$) δ$_H$: 3.36-3.43 (m, 2H), 4.26 (t, J=7.0 Hz, 1H), 4.43 (dd, J=12.6 Hz, 2H), 7.24 (d, J=8.0 Hz, 2H), 7.38 (t, J=8.8 Hz, 3H), 8.85 (d, J=0.8 Hz, 1H); $^{13}$C NMR (100 MHz, MeOH-d$_4$) δ$_C$: 26.27, 42.23, 52.04, 118.18, 120.79, 126.93, 129.19, 134.39, 137.11, 148.39, 167.11. HRMS (ESI) calc. for C$_{14}$H$_{16}$F$_3$N$_4$O$_2$ [M+H]$^+$ 329.1220. found 329.1228.

(S)-2-amino-3-(1H-imidazol-4-yl)-N-(4-((trifluoromethyl)thio)benzyl)propanamide (5r): Following general synthetic method B the title compound was synthesized as a white solid (62%). R$_f$=0.11 (MeOH:DCM=1:9). $^1$H NMR (500 MHz, MeOH-d$_4$) δ$_H$: 3.30-3.41 (m, 2H), 4.24 (t, J=7.02 Hz, 1H), 4.48 (q, J=16.61 Hz, 2H), 7.40 (d, J=8.13 Hz, 3H), 7.68 (d, J=8.14 Hz, 2H), 8.84 (s, 1H); $^{13}$C NMR (126 MHz, MeOH-d$_4$) δ$_C$: 26.29, 42.46, 52.12, 118.26, 122.80, 122.81, 126.94, 128.52, 128.67, 130.96, 134.40, 136.29, 141.51, 167.31. HRMS (ESI) calc. for C$_{14}$H$_{16}$F$_3$N$_4$OS [M+H]$^+$ 345.0991. found 345.0998.

(R)-2-amino-3-(1H-imidazol-4-yl)-N-(4-((trifluoromethyl)thio)benzyl)propanamide (5s): Following general synthetic method B the title compound was synthesized as a white solid (61%). R$_f$=0.11 (MeOH:DCM=1:9). $^1$H NMR (500 MHz, MeOH-d$_4$) δ$_H$: 3.31-3.43 (m, 2H), 4.27 (t, J=7.02 Hz, 1H), 4.48 (q, J=17.89 Hz, 2H), 7.39-7.42 (m, 3H), 7.67 (d, J=8.17 Hz, 2H), 8.86 (d, J=1.29 Hz, 1H); $^{13}$C NMR (126 MHz, MeOH-d$_4$) δ$_C$: 26.28, 42.44, 52.08, 118.23, 122.81, 122.83, 126.93, 128.68, 134.40, 136.30, 141.53, 167.27. HRMS (ESI) calc. for C$_{14}$H$_{16}$F$_3$N$_4$OS [M+H]$^+$ 345.0991. found 345.0995.

(S)-2-amino-3-(1H-imidazol-4-yl)-N-phenylpropanamide (6a): Following general synthetic method B the title compound was synthesized as a white solid (60%). R$_f$=0.11 (MeOH:DCM=1:9). $^1$H NMR (400 MHz, MeOH-d$_4$) δ$_H$: 3.39-3.53 (m, 2H), 4.38 (t, J=6.94 Hz 1H), 7.14-7.18 (m, 1H), 7.33-7.37 (m, 2H), 7.47 (s, 1H), 7.58 (dd, J=1.00, 7.69 Hz, 2H), 8.89 (d, J=1.19 Hz, 1H); $^{13}$C NMR (100 MHz, MeOH-d$_4$) δ$_C$: 26.31, 52.65, 118.26, 119.86, 124.71, 126.91, 128.61, 134.50, 137.33, 165.36. HRMS (ESI) calc. for C$_{12}$H$_{15}$N$_4$O [M+H]$^+$ 231.1240. found 231.1239.

(R)-2-amino-3-(1H-imidazol-4-yl)-N-phenylpropanamide (6b): Following general synthetic method B the title compound was synthesized as a white solid (63%). R$_f$=0.11 (MeOH:DCM=1:9). $^1$H NMR (400 MHz, MeOH-d$_4$) δ$_H$: 3.40-3.54 (m, 2H), 4.39 (t, J=6.94, 1H), 7.15-7.19 (m, 1H), 7.33-7.37 (m, 2H), 7.48 (s, 1H), 7.58-7.60 (m, 2H), 8.89 (d, J=1.23 Hz, 1H); $^{13}$C NMR (100 MHz, MeOH-d$_4$) δ$_C$: 26.31, 52.66, 118.27, 119.87, 124.70, 126.92, 128.61, 134.49, 137.33, 165.38. HRMS (ESI) calc. for C$_{12}$H$_{15}$N$_4$O [M+H]$^+$ 231.1240. found 231.1240.

(S)-2-amino-3-(1H-imidazol-4-yl)-N-(3-phenylpropyl)propanamide (7a): Following general synthetic method B the title compound was synthesized as a colorless oil (52%). R$_f$=0.16 (MeOH:DCM=1:9). $^1$H NMR (500 MHz, MeOH-d$_4$) δ$_H$: 1.79-1.82 (m, 2H), 2.61 (t, J=7.69 Hz, 2H), 3.24-3.28 (m, 2H), 3.30-3.38 (m, 2H), 4.19 (t, J=7.04 Hz, 1H), 7.16-7.20 (m, 3H), 7.26-7.29 (m, 2H), 7.44 (d, J=1.23 Hz, 1H), 8.85 (d, J=1.34 Hz, 1H); $^{13}$C NMR (126 MHz, MeOH-d$_4$) δ$_C$: 26.40, 30.50, 32.63, 38.96, 52.13, 118.17, 125.60, 127.17, 128.01, 128.06, 134.42, 141.28, 167.17. HRMS (ESI) calc. for C$_{15}$H$_{21}$N$_4$O [M+H]$^+$ 273.1710. found 273.1713.

(R)-2-amino-3-(1H-imidazol-4-yl)-N-(3-phenylpropyl)propanamide (7b): Following general synthetic method B the title compound was synthesized as a colorless oil (51%). R$_f$=0.16 (MeOH:DCM=1:9). $^1$H NMR (500 MHz, MeOH-d$_4$) δ$_H$: 1.78-1.84 (m, 2H), 2.61 (t, J=7.69 Hz, 2H), 3.24-3.26 (m, 2H), 3.28-3.40 (m, 2H), 4.22 (t, J=7.03 Hz, 1H), 7.18 (dd, J=13.84, 7.18 Hz, 3H), 7.27 (t, J=7.57 Hz, 2H), 7.46 (s, 1H), 8.88 (s, 1H); $^{13}$C NMR (126 MHz, MeOH-d$_4$) δ$_C$: 26.36, 30.48, 32.63, 38.97, 52.13, 118.22, 125.60, 127.09, 128.01, 128.05, 134.38, 141.27, 167.18. HRMS (ESI) calc. for C$_{15}$H$_{21}$N$_4$O [M+H]$^+$ 273.1710. found 273.1715.

(S)-2-amino-3-(1H-imidazol-4-yl)-N-(4-phenylbutyl)propanamide (8a): Following general synthetic method B the title compound was synthesized as a colorless oil (42%). R$_f$=0.17 (MeOH:DCM=1:9). $^1$H NMR (500 MHz, MeOH-d$_4$) δ$_H$: 1.48-1.54 (m, 2H), 1.58-1.64 (m, 2H), 2.63 (t, J=7.49 Hz, 2H), 3.23-3.29 (m, 2H), 3.31-3.37 (m, 2H), 4.18 (t, J=7.02 Hz, 1H), 7.17 (dd, J=13.89, 7.08 Hz, 3H), 7.26 (t, J=7.53 Hz, 2H), 7.43 (s, 1H), 8.83 (d, J=1.22 Hz, 1H); $^{13}$C NMR (126 MHz, MeOH-d$_4$) δ$_C$: 26.36, 28.31, 28.40, 34.94, 39.14, 52.01, 118.10, 125.44, 127.08, 127.95, 128.03, 134.41, 141.96, 166.96. HRMS (ESI) calc. for C$_{16}$H$_{23}$N$_4$O [M+H]$^+$ 287.1866. found 287.1868.

(R)-2-amino-3-(1H-imidazol-4-yl)-N-(4-phenylbutyl)propanamide (8b): Following general synthetic method B the title compound was synthesized as a colorless oil (43%). R$_f$=0.17 (MeOH:DCM=1:9). $^1$H NMR (500 MHz, MeOH-d$_4$) δ$_H$: 1.48-1.54 (m, 2H), 1.58-1.64 (m, 2H), 2.63 (t, J=7.49 Hz, 2H), 3.24-3.29 (m, 2H), 3.31-3.37 (m, 2H), 4.17 (t, J=7.01 Hz, 1H), 7.17 (dd, J=13.51, 7.14 Hz, 3H), 7.26 (t, J=7.53 Hz, 2H), 7.44 (s, 1H), 8.84 (d, J=1.13 Hz, 1H); $^{13}$C NMR (126 MHz, MeOH-d$_4$) δ$_C$: 26.32, 28.31, 28.39, 34.94, 39.14, 51.99, 118.12, 125.45, 127.02, 127.95, 128.03, 134.41, 141.95, 166.93. HRMS (ESI) calc. for C$_{16}$H$_{23}$N$_4$O [M+H]$^+$ 287.1866. found 287.1868.

(rac)-N-(2-(1H-indol-3-yl)ethyl)-2-amino-3-(1H-imidazol-4-yl)propenamide (9a): To a solution of Boc-protected intermediate 9b in DCM (5 mL) was added TFA (5 mL) and the reaction solution was stirred at room temperature overnight. The solvent was evaporated in vacuo. DCM (20 mL) was added to the residue, which was washed with an aqueous solution of NaHCO$_3$, the organic layer was basified to pH 7 (NaOH) separated, dried over anhydrous Na$_2$SO$_4$ and concentrated in vacuo to afford the title compound as a colorless solid (24%). $^1$H NMR (400 MHz, MeOH-d$_4$) δ$_H$: (Major) 1.30-1.39 (2H, m, CH$_2$), 1.50-1.52 (1H, m, CHH'), 1.71-1.73 (1H, m, CHH'), 2.60-3.16 (2H, m, CH), 3.41-3.58 (1H, m, CH), 6.67-6.88 (1H, m, ArH), 6.97-7.35 (3H, m, ArH), 7.50-7.69 (2H, m, ArH); $^{13}$C NMR (100 MHz, MeOH-d$_4$) δ$_C$: (Major) 28.67, 31.13, 39.69, 54.93, 111.67, 113.01, 117.93, 118.43, 120.30, 120.94, 123.10, 129.54, 132.69, 135.37, 136.77, 174.82.

(S)-tert-butyl (1-((2-(1H-indol-3-yl)ethyl)amino)-3-(1H-imidazol-4-yl)-1-oxopropan-2-yl)carbamate (9b): Following general synthetic method A the title compound was synthesized as a white solid (80%). R$_f$: 0.40 (9:1 DCM:MeOH). $^1$H NMR (400 MHz, MeOH-d$_4$) δ$_H$: 1.41 (9H, s, $^t$Bu), 2.83 (1H, dd, J=5.2 Hz, CHH'CH$_2$), 2.91 (2H, t, J=7.2 Hz, CH$_2$), 3.02 (1H, dd, J=5.2 Hz, CHH'CH$_2$), 3.43-3.56 (2H, m, CH$_2$), 4.27 (1H, q, J=5.6 Hz, CH), 6.86 (1H, s, ArH), 7.00-7.12 (3H, m, ArH), 7.34 (1H, d, J=8.0 Hz, ArH), 7.57 (1H, d, J=7.8 Hz, ArH), 7.68 (1H, s, ArH); $^{13}$C NMR (100 MHz, MeOH-d$_4$) δ$_C$: 24.76, 27.22, 29.25, 39.83, 48.23, 54.79, 79.30, 110.83, 111.61, 117.09, 117.85, 118.23, 120.94, 122.07, 127.29, 132.94, 134.63, 136.79, 156.16, 172.61.

N-(2-(1H-indol-3-yl)ethyl)-3-(1H-imidazol-4-yl)propenamide (9c): To a solution of tryptamine (229 mg, 1.43 mmol) in DCM (10 mL) at 0° C. was added DMAP (0.1 mmol) and EDAC (273 mg, 1.43 mmol) and the solution was stirred for 15 minutes. To the reaction vessel was added a solution of deaminohistidine (200 mg, 1.43 mmol) in DCM (2 mL) and the mixture stirred at 0° C. for 15 minutes and allowed to warm to room temperature with stirring continued overnight. The cream ppt was filtered and washed with water (50 mL), Et$_2$O (25 mL) and allowed to air dry to afford the title compound as a cream solid (52%). $^1$H NMR (400 MHz, MeOH-d$_4$) δ$_H$: 2.61 (2H, t, J=7.36 Hz, CH$_2$), 2.94 (2H, t, J=7.22 Hz), 3.13-3.16 (2H, m, CH$_2$), 3.24-3.27 (2H, m, CH$_2$), 7.05-7.09 (2H, m, ArH), 7.13-7.17 (1H, m, ArH), 7.20 (1H, s, ArH), 7.39 (1H, dt, J=8.12 and 0.86 Hz, ArH), 7.59 (1H, dt, J=7.85 and 0.86 Hz, ArH), 8.16 (1H, d, J=1.12 Hz, ArH); $^{13}$C NMR (100 MHz, MeOH-d$_4$) δ$_C$: 21.23, 23.15, 34.29, 39.85, 108.85, 111.16, 115.85, 117.48, 118.65, 121.36, 122.90, 126.78, 133.66, 134.99, 136.98, 176.48.

(S)—N-(2-(JH-indol-3-yl)ethyl)-2-amino-3-(1H-imidazol-4-yl)propanamide (9d): Following general synthetic method B the title compound was synthesized as a white solid (72%). R$_f$=0.14 (MeOH:DCM=1:9). [α]$^{24}$$_D$ 21 (c 0.1, MeOH). $^1$H NMR (400 MHz, MeOH-d$_4$) δ$_H$: 2.93-2.98 (m, 2H), 3.16-3.28 (m, 2H), 3.51-3.56 (m, 1H), 3.61-3.66 (m, 1H), 4.16 (t, J=6.82 Hz, 1H), 7.02 (t, J=7.35 Hz, 1H), 7.08-7.13 (m, 2H), 7.24 (s, 1H), 7.35 (d, J=8.09 Hz, 1H), 7.57 (d, J=7.85 Hz, 1H), 8.72 (d, J=1.18 Hz, 1H); $^{13}$C NMR (100 MHz, MeOH-d$_4$) δ$_C$: 24.59, 26.38, 40.04, 51.94, 110.96, 111.32, 117.82, 117.88, 118.31, 121.06, 122.20, 127.25, 134.29, 136.74, 167.09. HRMS (ESI) calc. for C$_{16}$H$_{20}$N$_5$O [M+H]$^+$ 298.1668. found 298.1659.

(R)—N-(2-(1H-indol-3-yl)ethyl)-2-amino-3-(1H-imidazol-4-yl)propanamide (9e): Following general synthetic method B the title compound was synthesized as a white solid (70%). R$_f$=0.14 (MeOH:DCM=1:9). [α]$^{24}$$_D$ −21 (c 0.1, MeOH). $^1$H NMR (400 MHz, MeOH-d$_4$) δ$_H$: 2.95 (t, J=7.26 Hz, 2H), 3.01-3.15 (m, 2H), 3.47-3.54 (m, 1H), 3.59-3.64 (m, 1H), 4.06 (t, J=6.89 Hz, 1H), 7.02 (q, J=4.90 Hz, 2H), 7.07-7.12 (m, 2H), 7.35 (d, J=8.12 Hz, 1H), 7.57 (d, J=7.84 Hz, 1H), 8.05 (s, 1H); $^{13}$C NMR (100 MHz, MeOH-d$_4$) δ$_C$: 24.66, 28.15, 40.04, 52.84, 110.92, 111.38, 117.80, 118.27, 121.03, 122.15, 127.27, 135.13, 136.80, 167.83. HRMS (ESI) calc. for C$_{16}$H$_{20}$N$_5$O [M+H]$^+$ 298.1668. found 298.1663.

(S)-2-amino-3-(1H-imidazol-4-yl)-N-(2-(naphthalen-2-yl)ethyl)propanamide (9f): Following general synthetic method B the title compound was synthesized as a colorless oil (57%). R$_f$=0.17 (MeOH:DCM=1:9). $^1$H NMR (400 MHz, MeOH-d$_4$) δ$_H$: 2.95-3.02 (m, 2H), 3.18-3.25 (m, 2H), 3.56-3.70 (m, 2H), 4.15 (t, J=6.80 Hz, 1H), 7.24 (s, 1H), 7.40-7.46 (m, 3H), 7.69 (s, 1H), 7.80-7.82 (m, 3H), 8.70 (s, 1H); $^{13}$C NMR (100 MHz, MeOH-d$_4$) δ$_C$: 26.41, 34.91, 40.49, 51.80, 117.83, 125.16, 125.75, 126.75, 126.77, 126.87, 127.05, 127.22, 127.79, 132.34, 133.60, 134.31, 136.16, 167.12. HRMS (ESI) calc. for C$_{18}$H$_{21}$N$_4$O [M+H]$^+$ 309.1710. found 309.1710.

(R)-2-amino-3-(1H-imidazol-4-yl)-N-(2-(naphthalen-2-yl)ethyl)propanamide (9g): Following general synthetic method B the title compound was synthesized as a colorless oil (58%). R$_f$=0.17 (MeOH:DCM=1:9). $^1$H NMR (400 MHz, MeOH-d$_4$) δ$_H$: 2.95-3.02 (m, 2H), 3.15-3.26 (m, 2H), 3.53-3.60 (m, 1H), 3.64-3.69 (m, 1H), 4.17 (t, J=6.78 Hz, 1H), 7.25 (d, J=1.19 Hz, 1H), 7.38-7.48 (m, 3H), 7.69 (s, 1H), 7.78-7.83 (m, 3H), 8.73 (d, J=1.37 Hz, 1H); $^{13}$C NMR (100 MHz, MeOH-d$_4$) δ$_C$: 26.33, 34.90, 40.49, 51.76, 117.91, 125.16, 125.74, 126.68, 126.75, 126.77, 127.05, 127.22, 127.79, 132.33, 133.60, 134.26, 136.16, 167.08. HRMS (ESI) calc. for C$_{18}$H$_{21}$N$_4$O [M+H]$^+$, 309.1710. found 309.1708.

(S)-2-amino-3-(1H-imidazol-4-yl)-N-(naphthalen-2-ylmethyl)propanamide (10a): Following general synthetic method B the title compound was synthesized as a colorless oil (68%). R$_f$=0.16 (MeOH:DCM=1:9). $^1$H NMR (500 MHz, MeOH-d$_4$) δ$_H$: 3.35-3.42 (m, 2H), 4.28 (t, J=7.04 Hz, 1H), 4.58 (q, J=11.94 Hz, 2H), 7.36-7.38 (m, 2H), 7.48-7.50 (m, 2H), 7.75 (s, 1H), 7.82-7.86 (m, 3H), 8.76 (d, J=1.24 Hz, 1H); $^{13}$C NMR (126 MHz, MeOH-d$_4$) δ$_C$: 26.30, 43.19, 52.07, 118.12, 125.48, 125.68, 126.00, 126.16, 126.90, 127.31, 127.35, 128.07, 132.84, 133.41, 134.28, 135.15, 167.02. HRMS (ESI) calc. for C$_{17}$H$_{19}$N$_4$O [M+H]$^+$ 295.1553. found 295.1560.

(R)-2-amino-3-(1H-imidazol-4-yl)-N-(naphthalen-2-ylmethyl)propanamide (10b): Following general synthetic method B the title compound was synthesized as a colorless oil (65%). R$_f$=0.16 (MeOH:DCM=1:9). $^1$H NMR (500 MHz, MeOH-d$_4$) δ$_H$: 3.26-3.33 (m, 2H), 4.20 (t, J=7.04 Hz, 1H), 4.49 (q, J=11.53 Hz, 2H), 7.27-7.29 (m, 2H), 7.38-7.41 (m, 2H), 7.65 (s, 1H), 7.73-7.77 (m, 3H), 8.66 (s, 1H); $^{13}$C NMR (126 MHz, MeOH-d$_4$) δ$_C$: 26.29, 43.19, 52.09, 118.14, 125.47, 125.68, 125.99, 126.15, 126.88, 127.31, 127.35, 128.07, 132.83, 133.40, 134.26, 135.15, 167.06. HRMS (ESI) calc. for C$_{17}$H$_{19}$N$_4$O [M+H]$^+$ 295.1553. found 295.1560.

(S)-2-amino-3-(1H-imidazol-4-yl)-N-(naphthalen-1-ylmethyl)propanamide (10c): Following general synthetic method B the title compound was synthesized as a yellowish oil (72%). $R_f$=0.16 (MeOH:DCM=1:9). $[\alpha]^{24}_D$ 26 (c 0.1, MeOH). $^1$H NMR (400 MHz, MeOH-d$_4$) $\delta_H$: 3.29-3.32 (m, 2H), 4.22 (t, J=7.11 Hz, 1H), 4.78 (d, J=14.87 Hz, 1H), 4.97 (d, J=14.81 Hz, 1H), 7.20 (s, 1H), 7.45-7.46 (m, 2H), 7.54-7.56 (m, 2H), 7.85 (t, J=4.77 Hz, 1H), 7.91-7.93 (m, 1H), 8.00 (d, J=9.20 Hz, 1H), 8.61 (d, J=1.22 Hz, 1H); $^{13}$C NMR (100 MHz, MeOH-d$_4$) $\delta_C$: 26.26, 40.99, 51.92, 117.91, 122.92, 125.05, 125.63, 126.17, 126.58, 126.71, 128.27, 128.50, 131.14, 132.86, 133.96, 134.05, 166.75. HRMS (ESI) calc. for $C_{17}H_{19}N_4O$ [M+H]$^+$ 295.1553. found 295.1549.

(R)-2-amino-3-(1H-imidazol-4-yl)-N-(naphthalen-1-ylmethyl)propanamide (10d): Following general synthetic method B the title compound was synthesized as a yellowish oil (70%). $R_f$=0.16 (MeOH:DCM=1:9). $[\alpha]^{24}_D$ −26 (c 0.1, MeOH). $^1$H NMR (400 MHz, MeOH-d$_4$) $\delta_H$: 3.29-3.31 (m, 2H), 4.21 (t, J=7.12 Hz, 1H), 4.78 (d, J=14.64 Hz, 1H), 4.97 (d, J=14.63 Hz, 1H), 7.19 (d, J=1.03 Hz, 1H), 7.45-7.46 (m, 2H), 7.54-7.56 (m, 2H), 7.86 (t, J=4.76 Hz, 1H), 7.92-7.94 (m, 1H), 8.00-8.02 (m, 1H), 8.61 (d, J=1.35 Hz, 1H); $^{13}$C NMR (100 MHz, MeOH-d$_4$) $\delta_C$: 26.32, 40.98, 51.93, 117.83, 122.92, 125.05, 125.63, 126.17, 126.59, 126.83, 128.27, 128.49, 131.13, 132.86, 133.95, 134.10, 166.76. HRMS (ESI) calc. for $C_{17}H_{19}N_4O$ [M+H]$^+$ 295.1553. found 295.1554.

(S)-2-amino-3-(1H-imidazol-4-yl)-N-(quinolin-8-yl)propanamide (11a): Following general synthetic method B the title compound was synthesized as a yellowish oil (53%). $R_f$=0.14 (MeOH:DCM=1:9). $[\alpha]^{24}_D$ 10 (c 0.4, MeOH). $^1$H NMR (500 MHz, MeOH-d$_4$) $\delta_H$: 3.54 (dd, J=6.87, 4.72 Hz, 2H), 4.76 (t, J=7.05 Hz, 1H), 7.56 (s, 1H), 7.61-7.64 (m, 2H), 7.77 (dd, J=8.30, 1.11 Hz, 1H), 8.39 (dd, J=8.33, 1.61 Hz, 1H), 8.57 (dd, J=7.64, 1.01 Hz, 1H), 8.91-8.92 (m, 2H); $^{13}$C NMR (126 MHz, MeOH-d$_4$) $\delta_C$: 26.41, 52.81, 118.52, 119.84, 121.93, 124.11, 126.72, 126.89, 128.48, 132.57, 134.66, 137.31, 138.72, 148.76, 165.92. HRMS (ESI) calc. for $C_{15}H_{16}N_5O$ [M+H]$^+$ 282.1349. found 282.1355.

(R)-2-amino-3-(1H-imidazol-4-yl)-N-(quinolin-8-yl)propanamide (Jib): Following general synthetic method B the title compound was synthesized as a yellowish oil (51%). $R_f$=0.14 (MeOH:DCM=1:9). $[\alpha]^{24}_D$ −10 (c 0.1, MeOH). $^1$H NMR (500 MHz, MeOH-d$_4$) $\delta_H$: 3.54 (dd, J=6.80, 5.20 Hz, 2H), 4.76 (t, J=7.04, Hz, 1H), 7.55 (s, 1H), 7.60-7.64 (m, 2H), 7.77 (dd, J=8.31, 1.08 Hz, 1H), 8.39 (dd, J=8.33, 1.60 Hz, 1H), 8.57-8.58 (m, 1H), 8.90-8.92 (m, 2H); $^{13}$C NMR (126 MHz, MeOH-d$_4$) $\delta_C$: 26.44, 52.80, 118.49, 119.18, 121.94, 123.90, 126.58, 126.90, 128.42, 132.83, 134.70, 136.80, 138.97, 148.93, 165.78. HRMS (ESI) calc. for $C_{15}H_{16}N_5O$ [M+H]$^+$ 282.1349. found 282.1355.

Biology. All studies were approved by the Institutional Animal Care and Use Committee (IACUC) of Texas Tech University Health Sciences Center, Lubbock, Texas (IACUC protocol #09007).

In Vitro Metabolic Stability: Metabolic stability was determined using mouse plasma and freshly made 10% mouse brain homogenate according to literature methods.[33,34] Briefly, stock solutions of the compounds were prepared at 10 µg/mL in LC-MS/MS grade water. Each biological matrix was spiked with compounds to afford a final concentration of 500 ng/mL. The tubes were placed on a water bath shaker at 37° C. for an incubation period of up to 4 hours. Sample aliquots (50 µL) of compound-containing matrices were removed at 0, 2, 5, 15, 30, 60, 120, 180 and 240 minutes. The samples were analyzed using an LC-MS/MS method developed by the present inventors.

Plasma and Brain Protein Binding: The rapid equilibrium dialysis (RED) plate and single-use inserts with a membrane MWCO of 8 kDa and sealing tapes for 96-well plates were purchased from (Pierce Biotechnology, Thermo Fisher Scientific, Waltham, MA). Test compounds were dissolved in dimethyl sulfoxide and then diluted to 10 g/mL with water for binding studies. The stock solutions (10 g/mL) were added to mouse brain homogenates or plasma. The final concentration of the compounds for the equilibrium dialysis experiment was 500 ng/mL. The RED device was assembled according to the manufacturer's instructions. A 200 µL aliquot of plasma or brain homogenate spiked with 500 ng/mL of selected compound was added to the sample chamber of insert (donor) and 400 µL of DPBS was added to the buffer chamber of the dialysis membrane (receiver). Then, the base plate was covered with a sealing tape and was incubated at 37° C. on an orbital shaker at 250 rpm for 4 hours to achieve equilibrium. Compounds were evaluated in triplicate for each experiment. At the end of incubation, equal volumes from both donor and receiver chambers were taken and placed in separate microcentrifuge for content analysis using LC-MS/MS.

Calculation of $f_u$: Fraction unbound ($f_u$) was calculated using equations 1 and 2 as described previously.[35] For calculation of brain protein binding, the dilution factor (D=5), that was used to prepare brain homogenate, should be considered whereas for plasma protein binding, no dilution was applied and only equation 1 was used to calculate fu.

$$\text{Diluted } fu, d = \frac{\text{Receiver concentration}}{\text{Donor concentration}} \qquad 1)$$

$$\text{Undiluted } fu = \frac{1/D}{\left((1/fu, d) - 1\right) + 1/D} \qquad 2)$$

In Vitro BBB Permeability: The BBB model was a co-culture of primary mouse astrocytes and immortalized mouse endothelial cells (bEnd3). bEnd3 cells were cultured in Dulbecco's modified Eagle's medium (DMEM) (Sigma, St. Louis, MO) with addition of 10% fetal bovine serum (FBS) (Atlanta biologicals, Minneapolis, MN) and 1% nonessential amino acid and 1% penicillin-streptomycin (PS) (Sigma, St. Louis, MO). Cells (passage 26-30) were maintained in a humidified cell culture incubator at 37° C. and with 5% CO$_2$/95% air. Mouse primary astrocytes were isolated from the cerebral cortices of one day old pups (CD-1 mice, Charles Rivers Laboratory) following a literature method.[36] After extracting the brain, cortices were separated, minced and placed in Hank's balanced salt solution (HBSS) without calcium and magnesium, supplemented with gentamycin (10 µg/m). Then cortices were incubated and digested with 0.25% trypsin for 15 minutes at 37° C. following by neutralizing with astrocyte media containing DMEM plus 10% FBS and 1% PS. The cell suspensions were seeded into a T75 flask and the medium was changed every 3 days for 10-14 days or until reaching confluency.

For bEnd3 and astrocyte co-culture, the Transwell filters (0.4-lm pore size, 12-well; Corning, Lowell, MA) were used. First, the Transwell filter was inverted and astrocytes at a density of 150,000 cells/filter were seeded onto the abluminal side of the filter and allowed to adhere for 4 hours. Then the Transwell filter was inverted back and the cells were grown for 2 days in astrocyte medium. At the end of 48 hours, bEnd3 cells at a density of 50,000 cells/filter were seeded onto the upper/luminal side of the filter and the co-culture of astrocytes and bEnd3 cells were grown for an additional 8 days. The medium for both compartments were changed every other day according to literature procedures.[37]

The apparent permeability coefficient ($P_e$, in cm/min) was calculated according to the cleared volume of each time point, as previously described.[38,39]

Permeability measurement for each compound was run for 120 minutes. The media was removed and transwells were rinsed and incubated with HBSS buffer at 37° C. for 30 minutes. Then, 10 µg/mL of each activator in HBSS was introduced to the apical/donor chamber. At different time points (0, 30, 60, 120 minutes) following addition of the compounds, 100 µL assay buffer was collected from the receiver compartment of the wells in duplicate for concentration determination and the removed volume was replaced with fresh buffer to avoid the back diffusion of the tested After precipitation, the samples were vortexed thoroughly for 1 min and centrifuged at 14000 rpm for 10 min at 4° C. The supernatants were collected in the vials and analyzed using LC-MS/MS.

The samples were analyzed using an AB SCIEX QTRAP® 5500 triple quadrupole mass spectrometer attached to a Nexera UPLC system (Shimadzu Corporation). The UPLC system contained an auto-sampler (Sil-30AC), pumps (LC-30AD), a controller (CBM-20A), a de-gasser (DGA-20A5), and a column oven (CTO-30A). Analyst software was used for data acquisition and quantification. For chromatographic separation, gradient elution using specific mobile phases for each compound was used with different chromatographic columns. Detailed information for the chromatographic separation of each compound is summarized in Table 9.

TABLE 9

Chromatographic separation of each compound

| Compound | Column | Mobile Phases | Flow rate (mL/min) | Gradient |
|---|---|---|---|---|
| Histidine-Tryptophan | BEH-C18 (2.1 mm × 50 mm, 1.7 µm; Waters, Milford, MA, USA) | A: Water + 0.1% FA B: Methanol + 0.1% FA | 0.25 | 0-0:50 min; 0-5% B, 0:50-2 min; to 30% B, 2-3:50 min; to 90% B, 3:50-5 min; to 5% B |
| Histidine-Tyrosine | RFP (2.1 mm × 100 mm, 2.7 µm; Raptor FluoroPhenyl, RESTEK, USA) | A: Water + 0.1% FA B: ACN + 0.1% FA | 0.4 | 0-0:10 min; 0-95% B, 0:10-3 min; to 50% B, 3-5 min; to 95% B |
| 9d 10c 11a | RFP (2.1 mm × 100 mm, 2.7 µm; Raptor FluoroPhenyl, RESTEK, USA) | A: Water + 0.1% FA B: ACN + 0.1% FA | 0.4 | 0-0:10 min; 0-10% B, 0:10-4 min; to 90% B, 4-5 min; to 10% B | compound. Concentration of compounds was determined by LC-MS/MS. Since the blank Transwell insert itself (without cells) provides resistance to the passage of buffer and compound from the donor to receiver chamber, the permeability of each compound was also measured in a blank insert and the final permeability coefficient results were calculated by considering the permeability of each compound in a blank insert.

LC-MS/MS Sample Preparation and Analysis: To prepare plasma, brain and buffer standard curves for each compound, these matrices were spiked with stock solutions of each compound to achieve final concentrations within the range of 7.8-1000 ng/mL and then these concentrations were subjected to sample preparation procedure similar to unknown samples. Also, blank control solutions were prepared accordingly without adding the compounds.

To prepare a sample for LC-MS/MS analysis, aliquoted matrix samples were precipitated using an organic solvent specific for each peptide.

Sample aliquots of Histidine-tryptophan were precipitated using cold trifluoroacetic acid solution (1% v/v) in methanol:water (1:1) at 1:3 ratio.

Sample aliquots of Histidine-tyrosine were precipitated using cold formic acid (FA) solution (0.1% v/v) in acetonitrile at 1:3 ratio followed by thoroughly vortexing and then adding 1:1 ratio water.

Sample aliquots of 9d, 10c and 11a were precipitated using cold FA solution (0.1% v/v) in acetonitrile:water (80:20 mixture) at 1:3 ratio.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES—EXAMPLE 1

Burbach, J. P. (2010) Neuropeptides from concept to online database www.neuropeptides.nl. European journal of pharmacology 626, 27-48

Hokfelt, T., Bartfai, T., and Bloom, F. (2003) Neuropeptides: opportunities for drug discovery. The Lancet. Neurology 2, 463-472

Burbach, J. P. (2011) What are neuropeptides?Methods in molecular biology 789, 1-36

Lopez-Otin, C., and Bond, J. S. (2008) Proteases: multifunctional enzymes in life and disease. The Journal of biological chemistry 283, 30433-30437

Shrimpton, C. N., Smith, A. I., and Lew, R. A. (2002) Soluble metalloendopeptidases and neuroendocrine signaling. Endocrine reviews 23, 647-664

Karamyan, V. T., and Speth, R. C. (2007) Enzymatic pathways of the brain renin-angiotensin system: unsolved problems and continuing challenges. Regul Pept 143, 15-27

Davis, T. P., and Konings, P. N. (1993) Peptidases in the CNS: formation of biologically active, receptor-specific peptide fragments. Crit Rev Neurobiol 7, 163-174

Kim, M., Hersh, L. B., Leissring, M. A., Ingelsson, M., Matsui, T., Farris, W., Lu, A., Hyman, B. T., Selkoe, D. J., Bertram, L., and Tanzi, R. E. (2007) Decreased catalytic activity of the insulin-degrading enzyme in chromosome 10-linked Alzheimer disease families. The Journal of biological chemistry 282, 7825-7832

Huang, S. M., Mouri, A., Kokubo, H., Nakajima, R., Suemoto, T., Higuchi, M., Staufenbiel, M., Noda, Y., Yamaguchi, H., Nabeshima, T., Saido, T. C., and Iwata, N. (2006) Neprilysin-sensitive synapse-associated amyloid-beta peptide oligomers impair neuronal plasticity and cognitive function. The Journal of biological chemistry 281, 17941-17951

Savolainen, M. H., Yan, X., Myohanen, T. T., and Huttunen, H. J. (2015) Prolyl oligopeptidase enhances alpha-synuclein dimerization via direct protein-protein interaction. The Journal of biological chemistry 290, 5117-5126

Basurto-Islas, G., Grundke-Iqbal, I., Tung, Y. C., Liu, F., and Iqbal, K. (2013) Activation of asparaginyl endopeptidase leads to Tau hyperphosphorylation in Alzheimer disease. The Journal of biological chemistry 288, 17495-17507

Rohnert, P., Schmidt, W., Emmerlich, P., Goihl, A., Wrenger, S., Bank, U., Nordhoff, K., Tager, M., Ansorge, S., Reinhold, D., and Striggow, F. (2012) Dipeptidyl peptidase IV, aminopeptidase N and DPIV/APN-like proteases in cerebral ischemia. J Neuroinflammation 9, 44

Simoes, P. S., Visniauskas, B., Perosa, S. R., Yacubian, E. M., Centeno, R., Canzian, M., Lopes-Cendes, I., Maurer Morelli, C. V., Carrete, H., Jr., Cavalheiro, E. A., Tufik, S., Chagas, J. R., and Mazzacoratti Mda, G. (2014) Expression and activity of thimet oligopeptidase (TOP) are modified in the hippocampus of subjects with temporal lobe epilepsy (TLE). Epilepsia 55, 754-762

Drag, M., and Salvesen, G. S. (2010) Emerging principles in protease-based drug discovery. Nat Rev Drug Discov 9, 690-701

Deu, E., Verdoes, M., and Bogyo, M. (2012) New approaches for dissecting protease functions to improve probe development and drug discovery. Nat Struct Mol Biol 19, 9-16

Shen, A. (2010) Allosteric regulation of protease activity by small molecules. Mol Biosyst 6, 1431-1443

Novinec, M., Korenc, M., Caflisch, A., Ranganathan, R., Lenarcic, B., and Baici, A. (2014) A novel allosteric mechanism in the cysteine peptidase cathepsin K discovered by computational methods. Nat Commun 5, 3287

Hines, C. S., Ray, K., Schmidt, J. J., Xiong, F., Feenstra, R. W., Pras-Raves, M., de Moes, J. P., Lange, J. H., Melikishvili, M., Fried, M. G., Mortenson, P., Charlton, M., Patel, Y., Courtney, S. M., Kruse, C. G., and Rodgers, D. W. (2014) Allosteric inhibition of the neuropeptidase neurolysin. The Journal of biological chemistry 289, 35605-35619

Spencer, B., Verma, I., Desplats, P., Morvinski, D., Rockenstein, E., Adame, A., and Masliah, E. (2014) A neuroprotective brain-penetrating endopeptidase fusion protein ameliorates Alzheimer disease pathology and restores neurogenesis. The Journal of biological chemistry 289, 17917-17931

Eckman, E. A., Reed, D. K., and Eckman, C. B. (2001) Degradation of the Alzheimer's amyloid beta peptide by endothelin-converting enzyme. The Journal of biological chemistry 276, 24540-24548

Qiu, W. Q., Walsh, D. M., Ye, Z., Vekrellis, K., Zhang, J., Podlisny, M. B., Rosner, M. R., Safavi, A., Hersh, L. B., and Selkoe, D. J. (1998) Insulin-degrading enzyme regulates extracellular levels of amyloid beta-protein by degradation. The Journal of biological chemistry 273, 32730-32738

Leissring, M. A. (2008) The AbetaCs of Abeta-cleaving proteases. The Journal of biological chemistry 283, 29645-29649

Chen, J., Zhao, Y., Chen, S., Wang, J., Xiao, X., Ma, X., Penchikala, M., Xia, H., Lazartigues, E., Zhao, B., and Chen, Y. (2014) Neuronal over-expression of ACE2 protects brain from ischemia-induced damage. Neuropharmacology 79, 550-558

Bennion, D. M., Haltigan, E. A., Irwin, A. J., Donnangelo, L. L., Regenhardt, R. W., Pioquinto, D. J., Purich, D. L., and Sumners, C. (2015) Activation of the Neuroprotective Angiotensin-Converting Enzyme 2 in Rat Ischemic Stroke. Hypertension 66, 141-148

Rashid, M., Wangler, N. J., Yang, L., Shah, K., Arumugam, T. V., Abbruscato, T. J., and Karamyan, V. T. (2014) Functional upregulation of endopeptidase neurolysin during post-acute and early recovery phases of experimental stroke in mouse brain. Journal of neurochemistry 129, 179-189

Dauch, P., Vincent, J. P., and Checler, F. (1995) Molecular cloning and expression of rat brain endopeptidase 3.4.24.16. J Biol Chem 270, 27266-27271

Hernandez Prada, J. A., Ferreira, A. J., Katovich, M. J., Shenoy, V., Qi, Y., Santos, R. A., Castellano, R. K., Lampkins, A. J., Gubala, V., Ostrov, D. A., and Raizada, M. K. (2008) Structure-based identification of small-molecule angiotensin-converting enzyme 2 activators as novel antihypertensive agents. Hypertension 51, 1312-1317

Kulemina, L. V., and Ostrov, D. A. (2011) Prediction of off-target effects on angiotensin-converting enzyme 2. J Biomol Screen 16, 878-885

Kabsch, W., and Sander, C. (1983) Dictionary of protein secondary structure: pattern recognition of hydrogen-bonded and geometrical features. Biopolymers 22, 2577-2637

Dundas, J., Ouyang, Z., Tseng, J., Binkowski, A., Turpaz, Y., and Liang, J. (2006) CASTp: computed atlas of surface topography of proteins with structural and topographical mapping of functionally annotated residues. Nucleic acids research 34, W116-118

Lipinski, C. A., Lombardo, F., Dominy, B. W., and Feeney, P. J. (2001) Experimental and computational approaches to estimate solubility and permeability in drug discovery and development settings. Adv Drug Deliv Rev 46, 3-26

Lian, W., Chen, G., Wu, D., Brown, C. K., Madauss, K., Hersh, L. B., and Rodgers, D. W. (2000) Crystallization and preliminary analysis of neurolysin. Acta Crystallogr D Biol Crystallogr 56, 1644-1646

Brown, C. K., Madauss, K., Lian, W., Beck, M. R., Tolbert, W. D., and Rodgers, D. W. (2001) Structure of neurolysin reveals a deep channel that limits substrate access. Proc Natl Acad Sci USA 98, 3127-3132

Wangler, N. J., Santos, K. L., Schadock, I., Hagen, F. K., Escher, E., Bader, M., Speth, R. C., and Karamyan, V. T. (2012) Identification of Membrane-bound Variant of Metalloendopeptidase Neurolysin (EC 3.4.24.16) as the Non-angiotensin Type 1 (Non-AT1), Non-AT2 Angiotensin Binding Site. J Biol Chem 287, 114-122

Rashid, M., Arumugam, T. V., and Karamyan, V. T. (2010) Association of the novel non-AT1, non-AT2 angiotensin binding site with neuronal cell death. J Pharmacol Exp Ther 335, 754-761

Dauch, P., Barelli, H., Vincent, J. P., and Checler, F. (1991) Fluorimetric assay of the neurotensin-degrading metalloendopeptidase, endopeptidase 24.16. The Biochemical journal 280 (Pt 2), 421-426

Shrimpton, C. N., Glucksman, M. J., Lew, R. A., Tullai, J. W., Margulies, E. H., Roberts, J. L., and Smith, A. I. (1997) Thiol activation of endopeptidase EC 3.4.24.15. A novel mechanism for the regulation of catalytic activity. J Biol Chem 272, 17395-17399

Miners, J. S., Verbeek, M. M., Rikkert, M. O., Kehoe, P. G., and Love, S. (2008) Immunocapture-based fluorometric assay for the measurement of neprilysin-specific enzyme activity in brain tissue homogenates and cerebrospinal fluid. Journal of neuroscience methods 167, 229-236

Joyner, J. C., Hocharoen, L., and Cowan, J. A. (2012) Targeted catalytic inactivation of angiotensin converting enzyme by lisinopril-coupled transition-metal chelates. J Am Chem Soc 134, 3396-3410

Vickers, C., Hales, P., Kaushik, V., Dick, L., Gavin, J., Tang, J., Godbout, K., Parsons, T., Baronas, E., Hsieh, F., Acton, S., Patane, M., Nichols, A., and Tummino, P. (2002) Hydrolysis of biological peptides by human angiotensin-converting enzyme-related carboxypeptidase. J Biol Chem 277, 14838-14843

Towler, P., Staker, B., Prasad, S. G., Menon, S., Tang, J., Parsons, T., Ryan, D., Fisher, M., Williams, D., Dales, N. A., Patane, M. A., and Pantoliano, M. W. (2004) ACE2 X-ray structures reveal a large hinge-bending motion important for inhibitor binding and catalysis. The Journal of biological chemistry 279, 17996-18007

Ray, K., Hines, C. S., Coll-Rodriguez, J., and Rodgers, D. W. (2004) Crystal structure of human thimet oligopeptidase provides insight into substrate recognition, regulation, and localization. J Biol Chem 279, 20480-20489

Oliveira, V., Gatti, R., Rioli, V., Ferro, E. S., Spisni, A., Camargo, A. C., Juliano, M. A., and Juliano, L. (2002) Temperature and salts effects on the peptidase activities of the recombinant metallooligopeptidases neurolysin and thimet oligopeptidase. European journal of biochemistry/FEBS 269, 4326-4334

Feng, B. Y., Shelat, A., Doman, T. N., Guy, R. K., and Shoichet, B. K. (2005) High-throughput assays for promiscuous inhibitors. Nat Chem Biol 1, 146-148

Feng, B. Y., Simeonov, A., Jadhav, A., Babaoglu, K., Inglese, J., Shoichet, B. K., and Austin, C. P. (2007) A high-throughput screen for aggregation-based inhibition in a large compound library. J Med Chem 50, 2385-2390

Goode, D. R., Totten, R. K., Heeres, J. T., and Hergenrother, P. J. (2008) Identification of promiscuous small molecule activators in high-throughput enzyme activation screens. J Med Chem 51, 2346-2349

Rioli, V., Gozzo, F. C., Heimann, A. S., Linardi, A., Krieger, J. E., Shida, C. S., Almeida, P. C., Hyslop, S., Eberlin, M. N., and Ferro, E. S. (2003) Novel natural peptide substrates for endopeptidase 24.15, neurolysin, and angiotensin-converting enzyme. J Biol Chem 278, 8547-8555

Fontes, R., Ribeiro, J. M., and Sillero, A. (2000) Inhibition and activation of enzymes. The effect of a modifier on the reaction rate and on kinetic parameters. Acta Biochim Pol 47, 233-257

Monod, J., Wyman, J., and Changeux, J. P. (1965) On the Nature of Allosteric Transitions: A Plausible Model. Journal of molecular biology 12, 88-118

Lim, E. J., Sampath, S., Coll-Rodriguez, J., Schmidt, J., Ray, K., and Rodgers, D. W. (2007) Swapping the substrate specificities of the neuropeptidases neurolysin and thimet oligopeptidase. The Journal of biological chemistry 282, 9722-9732

Pacholec, M., Bleasdale, J. E., Chrunyk, B., Cunningham, D., Flynn, D., Garofalo, R. S., Griffith, D., Griffor, M., Loulakis, P., Pabst, B., Qiu, X., Stockman, B., Thanabal, V., Varghese, A., Ward, J., Withka, J., and Ahn, K. (2010) SRT1720, SRT2183, SRT1460, and resveratrol are not direct activators of SIRT1. The Journal of biological chemistry 285, 8340-8351

Song, E. S., Juliano, M. A., Juliano, L., Fried, M. G., Wagner, S. L., and Hersh, L. B. (2004) ATP effects on insulin-degrading enzyme are mediated primarily through its triphosphate moiety. The Journal of biological chemistry 279, 54216-54220

Dahms, P., and Mentlein, R. (1992) Purification of the main somatostatin-degrading proteases from rat and pig brains, their action on other neuropeptides, and their identification as endopeptidases 24.15 and 24.16. Eur J Biochem 208, 145-154

Vincent, B., Jiracek, J., Noble, F., Loog, M., Roques, B., Dive, V., Vincent, J. P., and Checler, F. (1997) Contribution of endopeptidase 3.4.24.15 to central neurotensin inactivation. Eur J Pharmacol 334, 49-53

Rioli, V., Kato, A., Portaro, F. C., Cury, G. K., te Kaat, K., Vincent, B., Checler, F., Camargo, A. C., Glucksman, M. J., Roberts, J. L., Hirose, S., and Ferro, E. S. (1998) Neuropeptide specificity and inhibition of recombinant isoforms of the endopeptidase 3.4.24.16 family: comparison with the related recombinant endopeptidase 3.4.24.15. Biochem Biophys Res Commun 250, 5-11

Walker, K., Perkins, M., and Dray, A. (1995) Kinins and kinin receptors in the nervous system. Neurochemistry international 26, 1-16

Tyler-McMahon, B. M., Boules, M., and Richelson, E. (2000) Neurotensin: peptide for the next millennium. Regulatory peptides 93, 125-136

Olias, G., Viollet, C., Kusserow, H., Epelbaum, J., and Meyerhof, W. (2004) Regulation and function of somatostatin receptors. Journal of neurochemistry 89, 1057-1091

Heimann, A. S., Gomes, I., Dale, C. S., Pagano, R. L., Gupta, A., de Souza, L. L., Luchessi, A. D., Castro, L. M., Giorgi, R., Rioli, V., Ferro, E. S., and Devi, L. A. (2007) Hemopressin is an inverse agonist of CB1 cannabinoid receptors. Proceedings of the National Academy of Sciences of the United States of America 104, 20588-20593

Sargeant, T. J., Miller, J. H., and Day, D. J. (2008) Opioidergic regulation of astroglial/neuronal proliferation: where are we now? Journal of neurochemistry 107, 883-897

Xia, H., and Lazartigues, E. (2008) Angiotensin-converting enzyme 2 in the brain: properties and future directions. Journal of neurochemistry 107, 1482-1494

Albert-Weissenberger, C., Siren, A. L., and Kleinschnitz, C. (2013) Ischemic stroke and traumatic brain injury: the role of the kallikrein-kinin system. Progress in neurobiology 101-102, 65-82

Turner, R., and Vink, R. (2007) Inhibition of neurogenic inflammation as a novel treatment for ischemic stroke. Drug News Perspect 20, 221-226

Caceda, R., Kinkead, B., and Nemeroff, C. B. (2006) Neurotensin: role in psychiatric and neurological diseases. Peptides 27, 2385-2404

Sumners, C., Horiuchi, M., Widdop, R. E., McCarthy, C., Unger, T., and Steckelings, U. M. (2013) Protective arms of the renin-angiotensin-system in neurological disease. Clin Exp Pharmacol Physiol 40, 580-588

Bisogno, T., and Di Marzo, V. (2010) Cannabinoid receptors and endocannabinoids: role in neuroinflammatory and neurodegenerative disorders. CNS Neurol Disord Drug Targets 9, 564-573

Feng, Y., He, X., Yang, Y., Chao, D., Lazarus, L. H., and Xia, Y. (2012) Current research on opioid receptor function. Curr Drug Targets 13, 230-246

Dauch, P., Vincent, J. P., and Checler, F. (1991) Specific inhibition of endopeptidase 24.16 by dipeptides. Eur J Biochem 202, 269-276

Cushman, D. W., and Ondetti, M. A. (1991) History of the design of captopril and related inhibitors of angiotensin converting enzyme. Hypertension 17, 589-592

Timmermans, P. B., Duncia, J. V., Carini, D. J., Chiu, A. T., Wong, P. C., Wexler, R. R., and Smith, R. D. (1995) Discovery of losartan, the first angiotensin II receptor antagonist. Journal of human hypertension 9 Suppl 5, S3-18.

REFERENCES—EXAMPLE 2

1. Writing Group, M.; Mozaffarian, D.; Benjamin, E. J.; Go, A. S.; Arnett, D. K.; Blaha, M. J.; Cushman, M.; Das, S. R.; de Ferranti, S.; Despres, J. P.; Fullerton, H. J.; Howard, V. J.; Huffman, M. D.; Isasi, C. R.; Jimenez, M. C.; Judd, S. E.; Kissela, B. M.; Lichtman, J. H.; Lisabeth, L. D.; Liu, S.; Mackey, R. H.; Magid, D. J.; McGuire, D. K.; Mohler, E. R., 3rd; Moy, C. S.; Muntner, P.; Mussolino, M. E.; Nasir, K.; Neumar, R. W.; Nichol, G.; Palaniappan, L.; Pandey, D. K.; Reeves, M. J.; Rodriguez, C. J.; Rosamond, W.; Sorlie, P. D.; Stein, J.; Towfighi, A.; Turan, T. N.; Virani, S. S.; Woo, D.; Yeh, R. W.; Turner, M. B.; American Heart Association Statistics, C.; Stroke Statistics, S., Executive Summary: Heart Disease and Stroke Statistics—2016 Update: A Report From the American Heart Association. Circulation 2016, 133 (4), 447-54.

2. Virani, S. S.; Alonso, A.; Benjamin, E. J.; Bittencourt, M. S.; Callaway, C. W.; Carson, A. P.; Chamberlain, A. M.; Chang, A. R.; Cheng, S.; Delling, F. N.; Djousse, L.; Elkind, M. S. V.; Ferguson, J. F.; Fornage, M.; Khan, S. S.; Kissela, B. M.; Knutson, K. L.; Kwan, T. W.; Lackland, D. T.; Lewis, T. T.; Lichtman, J. H.; Longenecker, C. T.; Loop, M. S.; Lutsey, P. L.; Martin, S. S.; Matsushita, K.; Moran, A. E.; Mussolino, M. E.; Perak, A. M.; Rosamond, W. D.; Roth, G. A.; Sampson, U. K. A.; Satou, G. M.; Schroeder, E. B.; Shah, S. H.; Shay, C. M.; Spartano, N. L.; Stokes, A.; Tirschwell, D. L.; VanWagner, L. B.; Tsao, C. W.; American Heart Association Council on, E.; Prevention Statistics, C.; Stroke Statistics, S., Heart Disease and Stroke Statistics—2020 Update: A Report From the American Heart Association. Circulation 2020, 141 (9), e139-e596.
3. Donkor, E. S., Stroke in the 21(st) Century: A Snapshot of the Burden, Epidemiology, and Quality of Life. Stroke Res Treat 2018, 2018, 3238165.
4. Collaborators, G. B. D. S., Global, regional, and national burden of stroke, 1990-2016: a systematic analysis for the Global Burden of Disease Study 2016. Lancet Neurol 2019, 18 (5), 439-458.
5. Hacke, W.; Donnan, G.; Fieschi, C.; Kaste, M.; von Kummer, R.; Broderick, J. P.; Brott, T.; Frankel, M.; Grotta, J. C.; Haley, E. C., Jr.; Kwiatkowski, T.; Levine, S. R.; Lewandowski, C.; Lu, M.; Lyden, P.; Marler, J. R.; Patel, S.; Tilley, B. C.; Albers, G.; Bluhmki, E.; Wilhelm, M.; Hamilton, S.; Investigators, A. T.; Investigators, E. T.; Investigators, N. r.-P. S. G., Association of outcome with early stroke treatment: pooled analysis of ATLANTIS, ECASS, and NINDS rt-PA stroke trials. Lancet 2004, 363 (9411), 768-74.
6. Sena, E.; van der Worp, H. B.; Howells, D.; Macleod, M., How can we improve the pre-clinical development of drugs for stroke?Trends Neurosci 2007, 30 (9), 433-9.
7. Macrae, I. M.; Allan, S. M., Stroke: The past, present and future. Brain Neurosci Adv 2018, 2, 2398212818810689.
8. Iadecola, C.; Anrather, J., Stroke research at a crossroad: asking the brain for directions. Nat Neurosci 2011, 14 (11), 1363-8.
9. Karamyan, V. T., The role of peptidase neurolysin in neuroprotection and neural repair after stroke. Neural Regen Res 2021, 16 (1), 21-25.
10. Karamyan, V. T., Peptidase neurolysin is an endogenous cerebroprotective mechanism in acute neurodegenerative disorders. Med Hypotheses 2019, 131, 109309.
11. Rashid, M.; Arumugam, T. V.; Karamyan, V. T., Association of the novel non-AT1, non-AT2 angiotensin binding site with neuronal cell death. J Pharmacol Exp Ther 2010, 335 (3), 754-61.
12. Rashid, M.; Wangler, N. J.; Yang, L.; Shah, K.; Arumugam, T. V.; Abbruscato, T. J.; Karamyan, V. T., Functional up-regulation of endopeptidase neurolysin during post-acute and early recovery phases of experimental stroke in mouse brain. J Neurochem 2014, 129 (1), 179-89.
13. Jayaraman, S.; Al Shoyaib, A.; Kocot, J.; Villalba, H.; Alamri, F. F.; Rashid, M.; Wangler, N. J.; Chowdhury, E. A.; German, N.; Arumugam, T. V.; Abbruscato, T. J.; Karamyan, V. T., Peptidase neurolysin functions to preserve the brain after ischemic stroke in male mice. J Neurochem 2020, 153 (1), 120-137.
14. Al-Ahmad, A. J.; Pervaiz, I.; Karamyan, V. T., Neurolysin substrates bradykinin, neurotensin and substance P enhance brain microvascular permeability in a human in vitro model. J Neuroendocrinol 2021, e12931.
15. Kinarivala, N.; Patel, R.; Boustany, R. M.; Al-Ahmad, A.; Trippier, P. C., Discovery of Aromatic Carbamates that Confer Neuroprotective Activity by Enhancing Autophagy and Inducing the Anti-Apoptotic Protein B-Cell Lymphoma 2 (Bcl-2). J Med Chem 2017, 60 (23), 9739-9756.
16. Kinarivala, N.; Suh, J. H.; Botros, M.; Webb, P.; Trippier, P. C., Pharmacophore elucidation of phosphoiodyn A—Potent and selective peroxisome proliferator-activated receptor beta/delta agonists with neuroprotective activity. Bioorg Med Chem Lett 2016, 26 (8), 1889-93.
17. Kinarivala, N.; Morsy, A.; Patel, R.; Carmona, A. V.; Sajib, M. S.; Raut, S.; Mikelis, C. M.; Al-Ahmad, A.; Trippier, P. C., An iPSC-Derived Neuron Model of CLN3 Disease Facilitates Small Molecule Phenotypic Screening. ACS Pharmacol Transl Sci 2020, 3 (5), 931-947.
18. Teixeira, P. F.; Masuyer, G.; Pinho, C. M.; Branca, R. M. M.; Kmiec, B.; Wallin, C.; Warmlander, S.; Berntsson, R. P.; Ankarcrona, M.; Graslund, A.; Lehtio, J.; Stenmark, P.; Glaser, E., Mechanism of Peptide Binding and Cleavage by the Human Mitochondrial Peptidase Neurolysin. J Mol Biol 2018, 430 (3), 348-362.
19. El-Faham, A.; Albericio, F., Peptide coupling reagents, more than a letter soup. Chem Rev 2011, 111 (11), 6557-602.
20. Ramu, V. G.; Bardaji, E.; Heras, M., DEPBT as coupling reagent to avoid racemization in a solution-phase synthesis of a Kyotorphin derivative. Synthesis 2014, 46 (11), 1481-1486.
21. Cherkupally, P.; Ramesh, S.; de la Torre, B. G.; Govender, T.; Kruger, H. G.; Albericio, F., Immobilized coupling reagents: synthesis of amides/peptides. ACS Comb Sci 2014, 16 (11), 579-601.
22. Castro, B.; Dormoy, J. R.; Dourtoglou, B.; Evin, G.; Selve, C.; J. C., Z., Peptide coupling reagents. VI. A novel, cheaper preparation of benzotriazolyloxytris[dimethylamine]phosphoniumhexafluorophisphate (BOP reagent). Synthesis 1976, 1976, 751-752.
23. Ribeiro, M. M.; Pinto, A.; Pinto, M.; Heras, M.; Martins, I.; Correia, A.; Bardaji, E.; Tavares, I.; Castanho, M., Inhibition of nociceptive responses after systemic administration of amidated kyotorphin. Br J Pharmacol 2011, 163 (5), 964-73.
24. Yao, J. F.; Yang, H.; Zhao, Y. Z.; Xue, M., Metabolism of Peptide Drugs and Strategies to Improve their Metabolic Stability. Curr Drug Metab 2018, 19 (11), 892-901.
25. Kumari, S.; Carmona, A. V.; Tiwari, A. K.; Trippier, P. C., Amide Bond Bioisosteres: Strategies, Synthesis, and Successes. J Med Chem 2020, 63 (21), 12290-12358.
26. Muttenthaler, M.; King, G. F.; Adams, D. J.; Alewood, P. F., Trends in peptide drug discovery. Nat Rev Drug Discov 2021.
27. Wager, T. T.; Hou, X.; Verhoest, P. R.; Villalobos, A., Moving beyond rules: the development of a central nervous system multiparameter optimization (CNS MPO) approach to enable alignment of druglike properties. ACS Chem Neurosci 2010, 1 (6), 435-49.
28. Johnson, T. W.; Gallego, R. A.; Edwards, M. P., Lipophilic Efficiency as an Important Metric in Drug Design. J Med Chem 2018, 61 (15), 6401-6420.
29. Trippier, P. C., Selecting Good 'Drug-Like' Properties to Optimize Small Molecule Blood-Brain Barrier Penetration. Curr Med Chem 2016, 23 (14), 1392-407.
30. Wang, H.; Huwaimel, B.; Verma, K.; Miller, J.; Germain, T. M.; Kinarivala, N.; Pappas, D.; Brookes, P. S.; Trippier, P. C., Synthesis and Antineoplastic Evaluation of Mitochondrial Complex II (Succinate Dehydrogenase) Inhibitors Derived from Atpenin A5. ChemMedChem 2017, 12 (13), 1033-1044.
31. Hopkins, A. L.; Keseru, G. M.; Leeson, P. D.; Rees, D. C.; Reynolds, C. H., The role of ligand efficiency metrics in drug discovery. Nat Rev Drug Discov 2014, 13 (2), 105-21.
32. Leeson, P. D.; Springthorpe, B., The influence of drug-like concepts on decision-making in medicinal chemistry. Nat Rev Drug Discov 2007, 6 (11), 881-90.

33. Li, N.; Han, Z. L.; Wang, Z. L.; Xing, Y. H.; Sun, Y. L.; Li, X. H.; Song, J. J.; Zhang, T.; Zhang, R.; Zhang, M. N.; Xu, B.; Fang, Q.; Wang, R., BN-9, a chimeric peptide with mixed opioid and neuropeptide FF receptor agonistic properties, produces nontolerance-forming antinociception in mice. Br J Pharmacol 2016, 173 (11), 1864-80.
34. Nan, D. D.; Gan, C. S.; Wang, C. W.; Qiao, J. P.; Wang, X. M.; Zhou, J. N., 6-Methoxy-indanone derivatives as potential probes for beta-amyloid plaques in Alzheimer's disease. Eur J Med Chem 2016, 124, 117-128.
35. Kalvass, J. C.; Maurer, T. S., Influence of nonspecific brain and plasma binding on CNS exposure: implications for rational drug discovery. Biopharm Drug Dispos 2002, 23 (8), 327-38.
36. Du, F.; Qian, Z. M.; Zhu, L.; Wu, X. M.; Qian, C.; Chan, R.; Ke, Y., Purity, cell viability, expression of GFAP and bystin in astrocytes cultured by different procedures. J Cell Biochem 2010, 109 (1), 30-7.
37. Li, G.; Simon, M. J.; Cancel, L. M.; Shi, Z. D.; Ji, X.; Tarbell, J. M.; Morrison, B., 3rd; Fu, B. M., Permeability of endothelial and astrocyte cocultures: in vitro blood-brain barrier models for drug delivery studies. Ann Biomed Eng 2010, 38 (8), 2499-511.
38. Nozohouri, S.; Noorani, B.; Al-Ahmad, A.; Abbruscato, T. J., Estimating Brain Permeability Using In Vitro Blood-Brain Barrier Models. Methods Mol Biol 2020.
39. Gaillard, P. J.; Voorwinden, L. H.; Nielsen, J. L.; Ivanov, A.; Atsumi, R.; Engman, H.; Ringbom, C.; de Boer, A. G.; Breimer, D. D., Establishment and functional characterization of an in vitro model of the blood-brain barrier, comprising a co-culture of brain capillary endothelial cells and astrocytes. Eur J Pharm Sci 2001, 12 (3), 215-22.

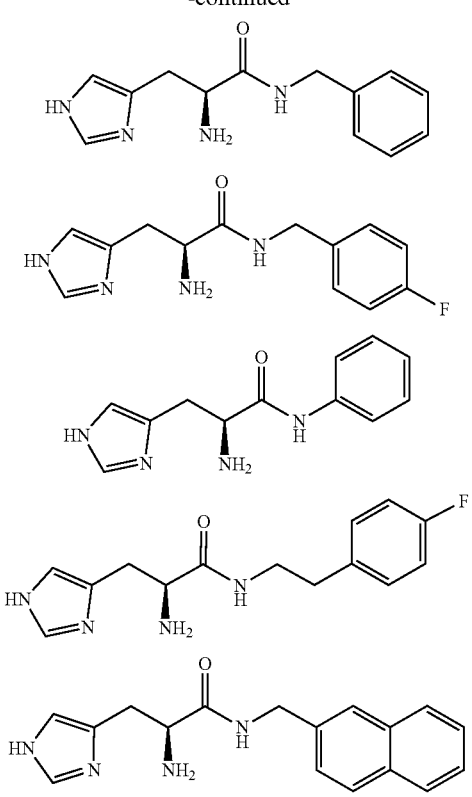

What is claimed is:

1. An allosteric activator of neurolysin selected from at least one of:

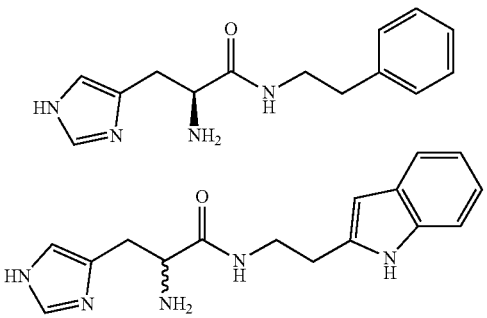

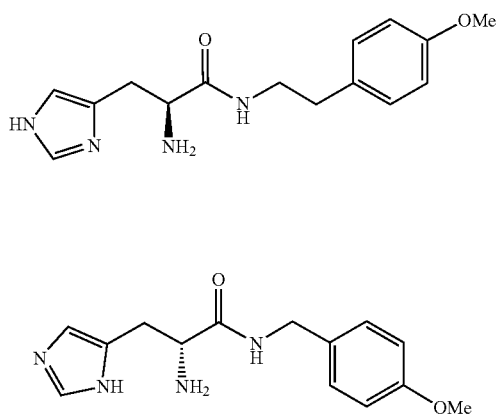

93 -continued
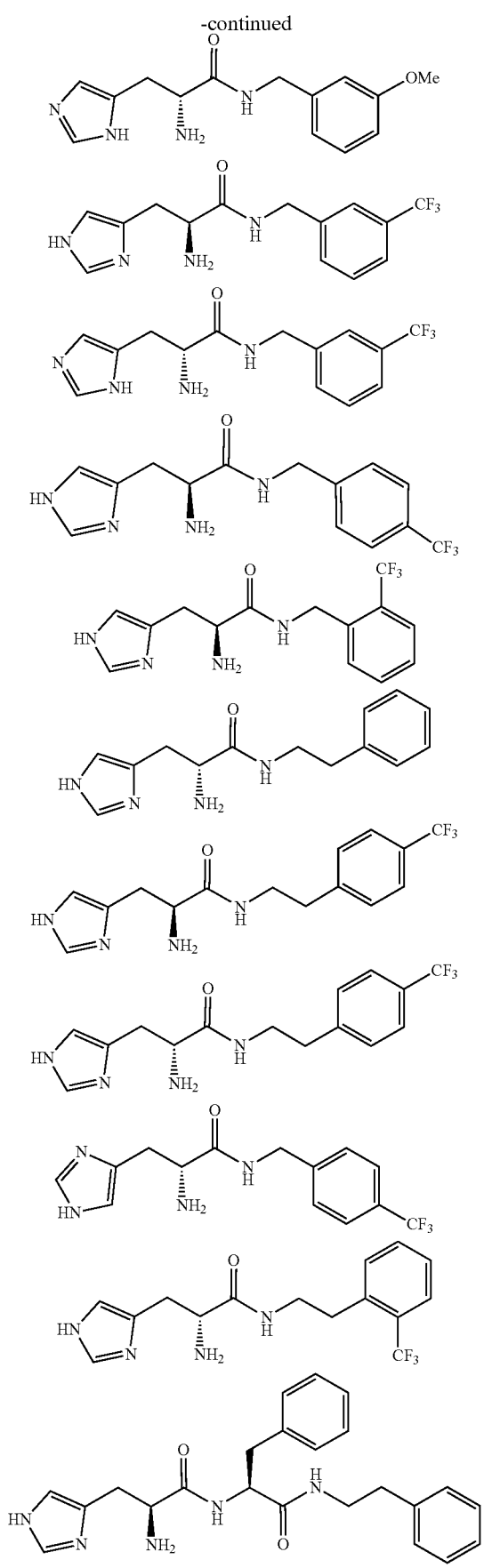
94 -continued
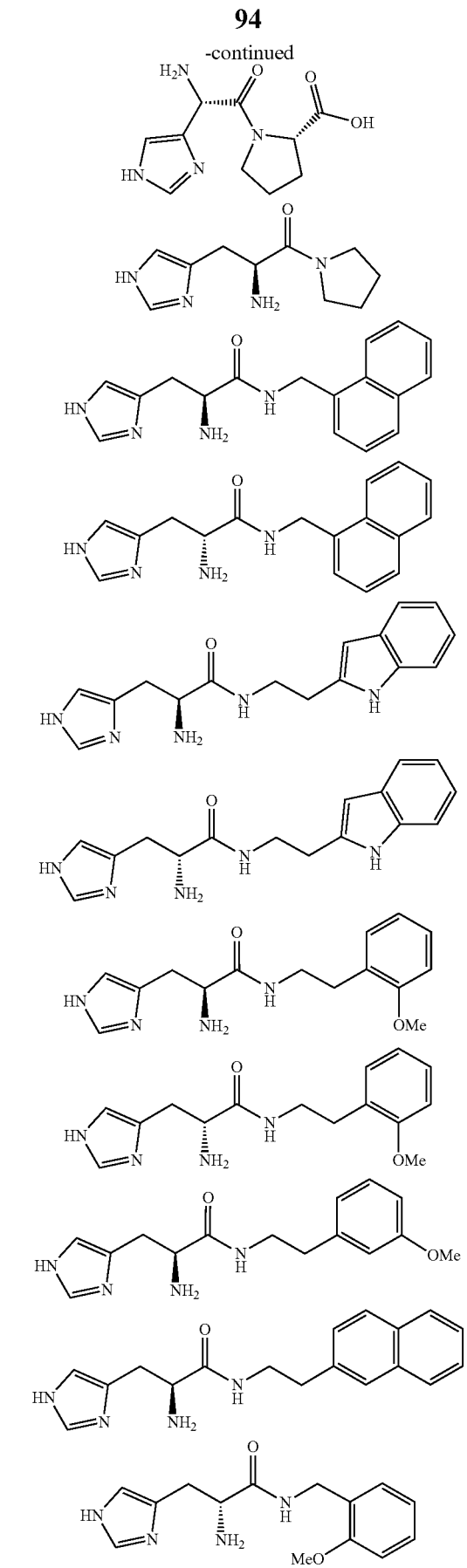

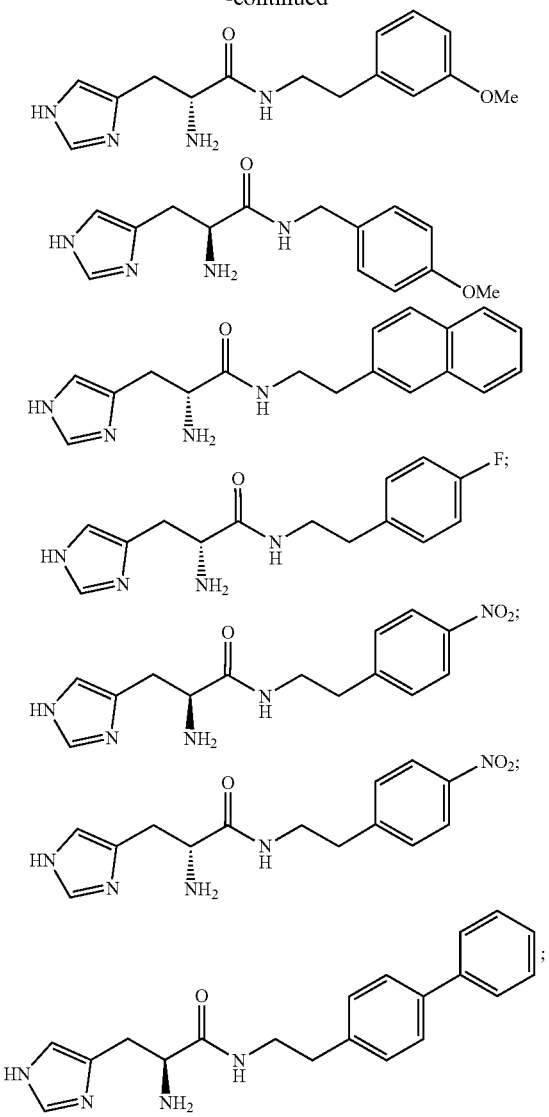

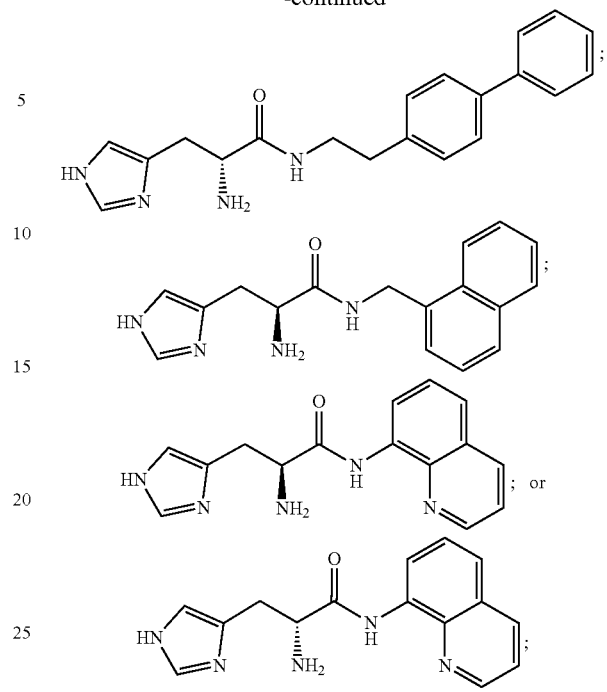

salts, or enantiomers thereof.

2. The activator of claim 1, wherein the inhibitor is adapted for oral, intraperitoneal, intradermal, subcutaneous, intravenous, enteral, parental, or pulmonary administration.

3. The activator of claim 1, wherein the inhibitor is combined with one or more excipients, buffers, fillers, or detergents.

4. The activator of claim 1, wherein the inhibitor is adapted for at least one of immediate release, delayed release, or prolonged release.

5. The activator of claim 1, wherein the activator comprises a single enantiomer.

* * * * *

SEQUENCE LISTING

<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: Synthetic peptide

<400> SEQUENCE: 1

Arg Pro Pro Gly Phe Ser Ala Phe Glu
1               5